United States Patent
O'Driscoll et al.

(10) Patent No.: US 10,753,836 B2
(45) Date of Patent: Aug. 25, 2020

(54) MULTI-AXIS SPECIMEN IMAGING DEVICE WITH EMBEDDED ORIENTATION MARKERS

(71) Applicant: Faxitron Bioptics, LLC, Tucson, AZ (US)

(72) Inventors: Donogh O'Driscoll, Tucson, AZ (US); Ciaran Purdy, Belfast (GB); Kimberly A. Fitzpatrick, Tucson, AZ (US); Marisa H. Borders, Tucson, AZ (US)

(73) Assignee: Faxitron Bioptics, LLC, Tucson, AZ (US)

( * ) Notice: Subject to any disclaimer, the term of this patent is extended or adjusted under 35 U.S.C. 154(b) by 0 days.

(21) Appl. No.: 15/904,567

(22) Filed: Feb. 26, 2018

(65) Prior Publication Data
US 2019/0072463 A1 Mar. 7, 2019

Related U.S. Application Data

(63) Continuation of application No. PCT/US2016/050169, filed on Sep. 2, 2016.

(60) Provisional application No. 62/214,520, filed on Sep. 4, 2015, provisional application No. 62/215,064, filed on Sep. 7, 2015.

(51) Int. Cl.
| | |
|---|---|
| G06K 9/00 | (2006.01) |
| G01N 1/36 | (2006.01) |
| B01L 3/00 | (2006.01) |
| G01N 23/04 | (2018.01) |
| C12M 1/00 | (2006.01) |
| A61B 10/00 | (2006.01) |
| A61B 10/02 | (2006.01) |

(52) U.S. Cl.
CPC ......... *G01N 1/36* (2013.01); *A61B 10/0041* (2013.01); *B01L 3/508* (2013.01); *C12M 45/22* (2013.01); *G01N 23/04* (2013.01); *A61B 10/0233* (2013.01); *B01L 2300/0609* (2013.01); *G01N 2223/307* (2013.01); *G01N 2223/6126* (2013.01)

(58) Field of Classification Search
None
See application file for complete search history.

(56) References Cited

U.S. PATENT DOCUMENTS

| | | | |
|---|---|---|---|
| 5,427,742 A | 6/1995 | Holland | |
| 8,162,140 B2 | 4/2012 | Hansen | |
| 2005/0112034 A1* | 5/2005 | McCormick | G01N 1/31 422/536 |
| 2007/0116612 A1 | 5/2007 | Williamson, IV | |
| 2013/0231585 A1 | 9/2013 | Flagle | |
| 2014/0065656 A1* | 3/2014 | Baysal | G01N 1/31 435/29 |

(Continued)

FOREIGN PATENT DOCUMENTS

WO 2013166497 11/2013

*Primary Examiner* — Wei Wen Yang

(57) ABSTRACT

A specimen holding and positioning apparatus operable to substantially non-movably maintain a specimen (e.g., an excised tissue specimen) in a fixed or stable orientation with respect to the apparatus during imaging operations (e.g., x-ray imaging), transport (e.g., from a surgery room to a pathologist's laboratory), and the like for use in facilitating accurate detection and diagnosis of cancers and/or other abnormalities of the specimen.

20 Claims, 55 Drawing Sheets

(56) References Cited

U.S. PATENT DOCUMENTS

2015/0083893 A1\* 3/2015 Wismueller .......... G01N 23/04
 250/208.1
2019/0285558 A1 9/2019 Defreitas et al.

\* cited by examiner

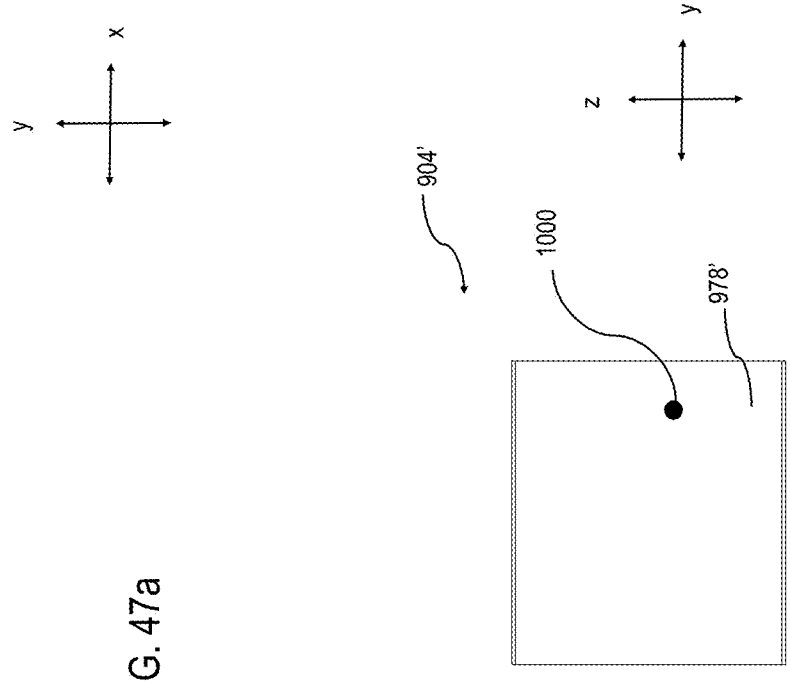
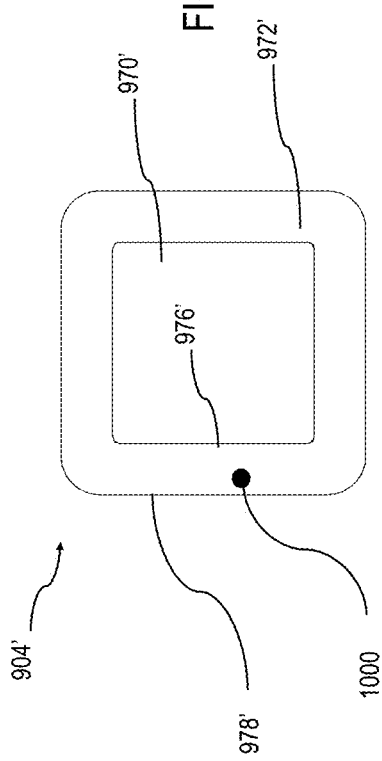
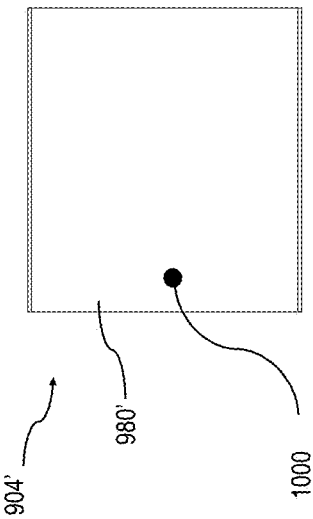
FIG. 47a
FIG. 47b
FIG. 47c

MULTI-AXIS SPECIMEN IMAGING DEVICE WITH EMBEDDED ORIENTATION MARKERS

CROSS REFERENCE TO RELATED APPLICATIONS

This application is a continuation of International Patent App. No. US/PCT2016/050169, entitled "MULTI-AXIS SPECIMEN IMAGING DEVICE WITH EMBEDDED ORIENTATION MARKERS," and filed on Sep. 2, 2016, which claims priority to U.S. Provisional Patent Application No. 62/215,064, entitled "MULTI-AXIS SPECIMEN IMAGING DEVICE WITH EMBEDDED ORIENTATION MARKERS," and filed on Sep. 7, 2015, and U.S. Provisional Patent Application No. 62/214,520, entitled "MULTI-AXIS SPECIMEN IMAGING DEVICE WITH EMBEDDED ORIENTATION MARKERS," and filed on Sep. 4, 2015. All the contents of the aforementioned applications are incorporated herein by reference in their entirety as if set forth in full.

FIELD OF THE INVENTION

This invention generally relates to tissue specimen analysis and, more particularly, to devices and methods for maintaining an excised tissue specimen in a fixed or stable orientation during imaging and transport to facilitate accurate detection of tissue margins, diagnosis of tissue abnormalities, and the like.

BACKGROUND

Definitive diagnosis of cancers such as breast cancer is typically accomplished through the surgical removal (e.g., biopsy) of the suspicious tissue (e.g., lesion) by a surgeon for further examination by a radiologist and/or pathologist. After a surgeon has appropriately identified a location of a possible lesion, the surgeon proceeds to excise tissue that includes the lesion and then verify that the entirety of the suspicious area is within the margins of the excised tissue. In this regard, a radiologist or the like will often x-ray or otherwise image the excised tissue specimen from multiple views (e.g., orthogonal views) to confirm appropriate tissue margins. In the event that the area of interest is too close or even contacts the tissue margins, the surgeon may need to excise additional tissue.

Once the tissue margins have been confirmed, the surgeon may then appropriately mark or otherwise indicate where on the excised tissue specimen a pathologist should focus during subsequent analysis and diagnosis. For instance, the excised tissue specimen may be positioned flat relative to a location identification member such as a grid or coordinate system (including any appropriate radiopaque lines, indicia, or the like) and then imaged (e.g., x-rayed) so that the grid lines/indicia appear in the resulting image. The surgeon may then appropriately inform the pathologist the location(s) of the most suspicious areas in the resulting image (e.g., by providing coordinates, marking directly on the image, etc.). The resulting image and excised tissue specimen may then be sent to the pathologist for performing a diagnostic procedure and providing a diagnostic opinion.

During all or most of the period between tissue specimen excision up to and including pathologist diagnosis, it is important for the tissue specimen to remain in a substantially constant shape and/or a substantially undisturbed position with respect to some particular reference point or device (e.g., relative to a tray or carrier used to transport the specimen). For instance, reshaping of the tissue specimen (e.g., compressing, folding, etc.) between the taking of first and second orthogonal images (e.g., for use in tissue margin detection) can make accurate tissue margin analysis difficult or even impossible. As another example, the pathologist may have difficulty reconciling the locations on the resulting image identified by the surgeon or radiologist and corresponding locations on the actual excised tissue specimen and possibly leading to an inaccurate diagnosis in the event that the tissue specimen is moved relative to the grid or coordinate system during transport from the surgeon or radiologist to the pathologist.

SUMMARY

The present disclosure is directed to devices, methods and systems (i.e., utilities) for maintaining an excised tissue specimen in a fixed or stable orientation during imaging and transport to facilitate accurate detection of tissue margins, diagnosis of tissue abnormalities, and the like. In one regard, the disclosed utilities may be used to facilitate accurate and efficient multi-axis imaging (e.g., orthogonal imaging) of a tissue specimen. In another regard, the disclosed utilities may be additionally used to facilitate substantially horizontal or flat imaging of the tissue specimen and a corresponding at least partially radiopaque grid or coordinate system to allow a surgeon or radiologist to accurately identify suspicious locations or areas in the excised tissue specimen to be subsequently analyzed by a pathologist or the like. In a further regard, the disclosed utilities may be additionally used to facilitate transport of the excised tissue specimen between two or more locations in a manner at least substantially free of changes in position or orientation of the tissue specimen relative to a reference location or device. Still further, the disclosed utilities may be used to substantially limit deformation and/or changes in shape of the specimen during imaging, transport, and the like.

In one aspect, an apparatus for positionably retaining a tissue specimen for imaging is disclosed including first and second positioning members that are broadly configured to retain a tissue specimen therebetween for use in specimen imaging, transport, diagnosis, and the like. More particularly, each of the first and second positioning members includes a portion thereof that is at least partially elastically deformable (e.g., made of a radiolucent material, such as a film or layer of material, polymeric foam, etc. so that fixable positioning of the first and second positioning members allows the portions to retain a tissue specimen therebetween within a specimen support volume of the apparatus. First and second orthogonal axes of the apparatus extend through the specimen support volume and a reference plane extends between the portions of the first and second positioning members when the first and second positioning members are fixably positioned relative to each other.

The apparatus also includes a first volume extending about and along the first axis from a first external side of the apparatus to a second external side of the apparatus and encompassing the specimen support volume and a second volume extending about and along the second axis from a third external side of the apparatus to a fourth external side of the apparatus and encompassing the specimen support volume. Each of the first and second volumes is free of any portion having a density greater than either a density of the portion of the first positioning member or a density of the portion of the second positioning member. Imaging of the specimen along the orthogonal first and second axes to obtain respective first and second images of the specimen (e.g., for use in verifying tissue margins, etc.) results in reduced levels of signal attenuation and thus increased quality (e.g., contrast, resolution, etc.) of the first and second specimen images.

In one arrangement, the apparatus may include or be usable with a grid member (e.g., sheet, board, etc.) having a series of grid lines (e.g., at least partially radiopaque grid lines) across at least one surface thereof for use in imparting the grid lines into resulting images of the tissue specimen (e.g., horizontal or flat images of the that may be used by a surgeon or radiologist to accurately indicate areas of interest on the specimen). In one embodiment, the grid member may be in the form of a rigid board (e.g., low attenuating or radiolucent material such as foam) that may be placed inside of the apparatus over one of the elastically deformable portions. Upon placing a tissue specimen onto the grid board, the first and second positioning members may be fixably positioned relative to each other (i.e., the apparatus may be closed) so as to at least partially deform the first and second sheet members about the tissue specimen and the grid board and thereby suspend the tissue specimen and grid board within the first and second openings of the first and second positioning members.

Various refinements may exist of the features noted in relation to the various aspects. Further features may also be incorporated in the various aspects. These refinements and additional features may exist individually or in any combination, and various features of the aspects may be combined. In addition to the exemplary aspects and embodiments described above, further aspects and embodiments will become apparent by reference to the drawings and by study of the following descriptions.

BRIEF DESCRIPTION OF THE DRAWINGS

For a more complete understanding of the present invention and further advantages thereof, reference is now made to the following Detailed Description, taken in conjunction with the drawings, in which:

FIGS. 47a-47c are top, front and side view of the first positioning member of FIG. 46.

DETAILED DESCRIPTION

Figure 1:
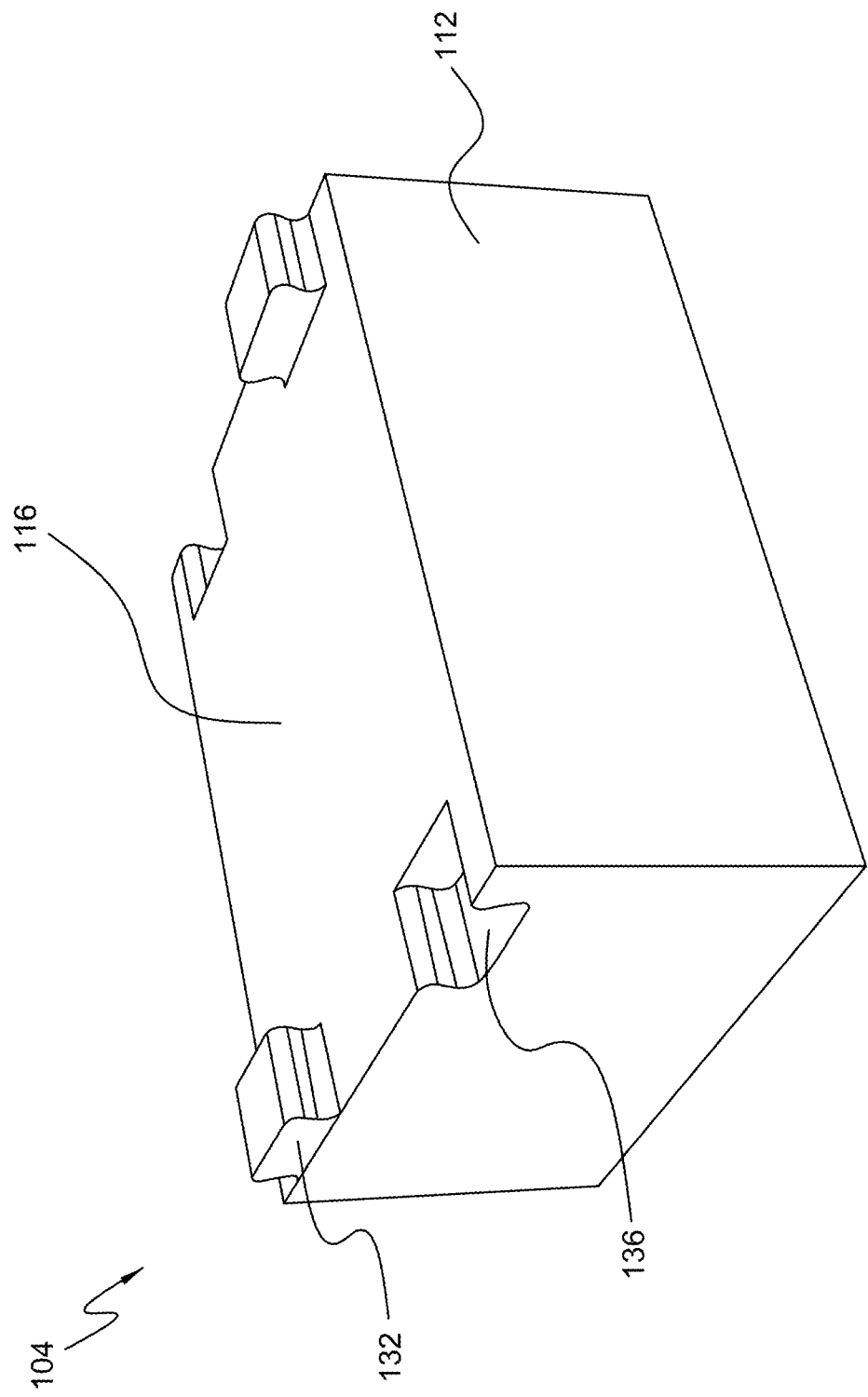
FIG. 1 is a perspective view of a first or lower positioning member of a specimen holding apparatus according to one embodiment.

Reference will now be made to the accompanying drawings, which assist in illustrating the various pertinent features of the various novel aspects of the present disclosure. In this regard, the following description is presented for purposes of illustration and description. Furthermore, the description is not intended to limit the inventive aspects to the forms disclosed herein. Consequently, variations and modifications commensurate with the following teachings, and skill and knowledge of the relevant art, are within the scope of the present inventive aspects.

With initial respect to FIGS. 1-5, a specimen holding and positioning apparatus 100 is disclosed that is operable to maintain a specimen 300 (e.g., an excised tissue specimen) in a fixed or stable orientation with respect to the apparatus 100 during imaging operations (e.g., x-ray imaging), transport (e.g., from a surgery room to a pathologist's laboratory), and the like to facilitate the accurate detection and diagnosis of cancers and/or other abnormalities of the specimen 300. Broadly, the apparatus 100 includes a first or lower positioning member 104 having a body 112 and an at least partially elastically deformable portion 116 (e.g., a "retention" portion or member), and a second or upper positioning member 108 having a body 120 and an at least partially elastically deformable portion 124 (e.g., a "retention" portion or member). Upon placement of at least one specimen 300 over the elastically deformable portion 116 of the first positioning member 104 and then securement of the second positioning member 108 to the first positioning member 104, the elastically deformable portions 116, 124 of the first and second positioning members are respectively configured to elastically deform about opposite portions of the specimen 300 to thereby retain the specimen 300 therebetween within a specimen support volume 128 of the apparatus 100 (see FIG. 5) for use in accurate imaging of the specimen, transport of the specimen and the like.

The apparatus 100 includes one or more features that allow for fixable positioning of the first and second positioning members 104, 180 to allow for substantial non-movable retaining of the specimen 300 between the first and second elastically deformable portions 116, 124 within the specimen support volume 128 of the apparatus 100. In one arrangement, the first and second positioning members 104, 108 may each include at least one respective connection member such as first and second connection members 132, 136 that are respectively configured to engage with the second and first connection members 136, 132 of the other of the first and second positioning members 104, 108. More particularly, each first connection member 132 of one of the first and second positioning members 104, 108 may be complimentary and removably connectable to a respective second connection member 136 of the other of the first and second positioning members 104, 108 to fixedly position the first and second positioning members 104, 108 relative to each other. In one embodiment, each of the first and second positioning members 104, 108 may include at least one first connection member 132 and at least one second connection member 136 adjacent respective first and second external sides of the apparatus 100.

For instance, each first connection member 132 may be in the form of a protrusion (e.g., tab, post, detent, etc.) and each second connection member 136 may be in the form of a complimentary-shaped and sized recess (e.g., opening, hole, etc.). In one embodiment, the first connection members 132 may be press fit into the second connection members 136. In another embodiment, the first connection members 132 may be snapped past and/or deformed into the second connection members 136. For instance, the various pairs of first and second connection members 132, 136 may be configured so that upon application of a particular separation force to the apparatus (i.e., a force tending to separate the first and second positioning members 104, 108 such as via a user grasping one of the first and second positioning members 104, 108 and pulling on the other of the first and second positioning members 104, 108), the first and second positioning members 104, 108 may be at least partially separated and the apparatus 100 opened (or moved into an open position or configuration) to allow for access to or placement of the tissue specimen 300 between the first and second elastically deformable portions 116, 124.

Each of the elastically deformable portions 116, 124 of the first and second positioning members 104, 108 is configured to at least partially transmit an imaging signal (e.g., electromagnetic radiation signal, such as an x-ray) therethrough to allow for imaging of the specimen 300 along first and second orthogonal axes 140, 144 through the apparatus 100 (e.g., including through the specimen support volume 128) to obtain respective first and second images of the specimen (e.g., for use in specimen margin verification and the like). In one arrangement, each of the first and second positioning members 104, 108 (e.g., and thus the elastically deformable portions 116, 124) may be substantially or fully constructed of any appropriate radiolucent solid (e.g., polymeric) foam(s) (e.g., such as respective blocks of solid foam). The low density and substantially uniform, homogeneous material properties solid foams substantially eliminates or at least reduces attenuation of an imaging signal passing through the apparatus 100 and thus substantially eliminates or at least reduces the likelihood of the apparatus appearing in an image of the specimen and correspondingly increases the quality (e.g., contrast, resolution, etc.) of the image (e.g., for use in verifying tissue margins, identifying suspicious locations or areas in the excised tissue specimen to be subsequently analyzed by a pathologist, and/or the like).

Furthermore, constructing the first and second positioning members 104, 108 of one or more solid foams allows the first and second positioning members 104, 108 to be fixably positioned relative to each other (e.g., via first and second connection members 132, 136 or the like, each of which may be integral or one-piece with its respective positioning member) free of additional (e.g., external) devices, supports, containers, etc. for fixedly positioning the first and second positioning members 104, 108 relative to each other. More particularly, the materials (e.g., rigid plastics) of such additional devices, supports, containers, etc. may have a radiodensity greater than that of the solid foam which would otherwise increase attenuation of imaging signals imaging of the specimen 300 and thus reduce the quality of resultant images of the specimen (e.g., via undesired artifacts in the images). For instance, each of the first and second positioning members 104, 108 may be substantially or fully constructed of at least one closed-cell, air filled foam. In one arrangement, the apparatus 100 (the first and second positioning members 104, 108) may be vacuum packed in a sealed pouch to render the package flat for shipping (e.g., due to constructing the apparatus entirely of foam).

The material properties (e.g., compression resistance, modulus of elasticity, etc.) and/or dimensions (e.g., thickness) of the elastically deformable portions 116, 124 of the first and second positioning members 104, 108 may be selected to retain the specimen 300 within the specimen support volume 128 of the apparatus 100 against movement relative to the apparatus 100. In one arrangement, the material properties and/or dimensions of the elastically deformable portions 116, 124 may be selected or configured to substantially inhibit deformation of the specimen 300 from its natural shape and dimensions while still retaining the specimen 300 against movement relative to the apparatus 100. As just one example, the thickness of one or both of the elastically deformable portions 116, 124 may be greater than about 0.1", such as greater than about 1", or greater than about 2".

Figure 2:
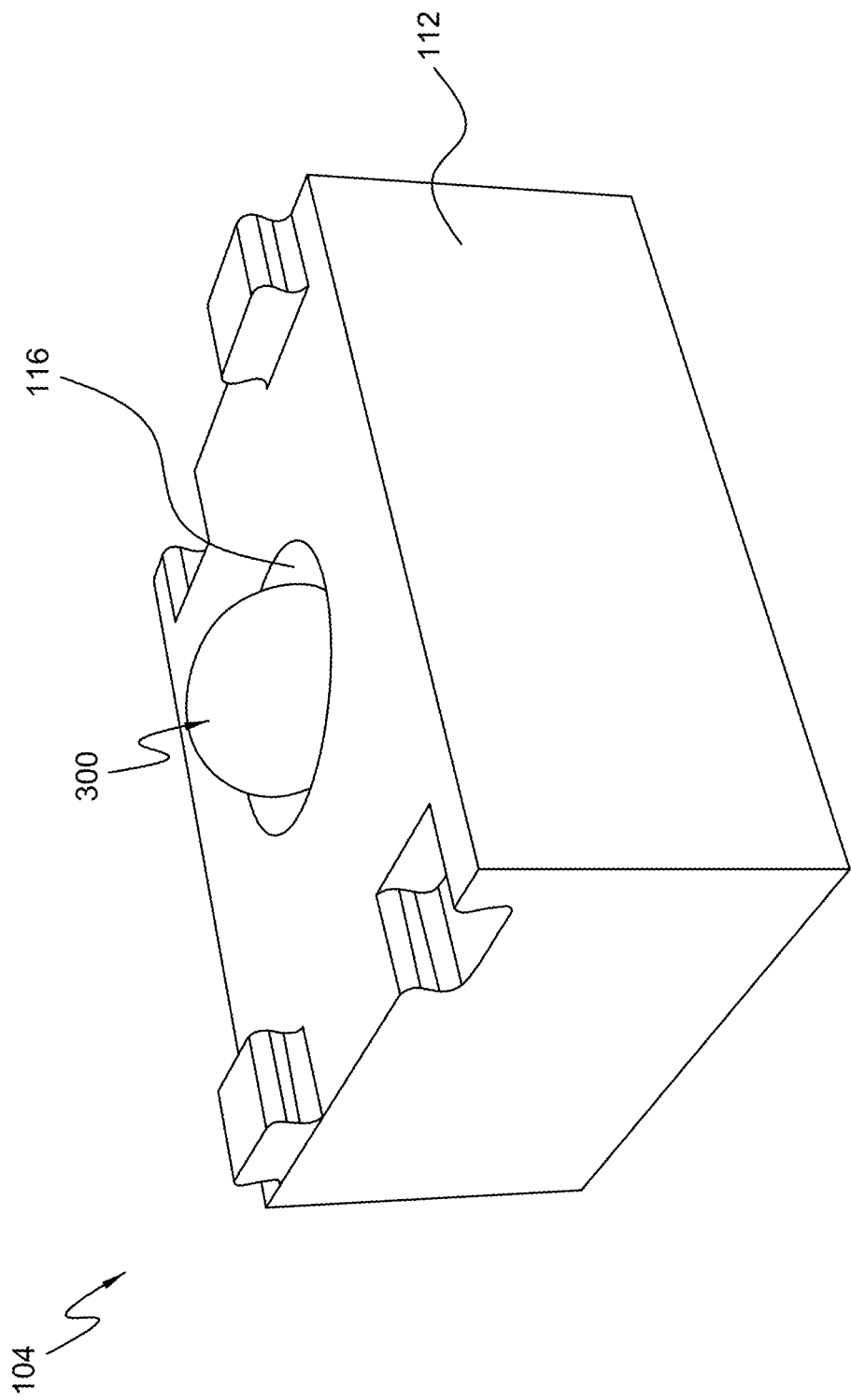
FIG. 2 is a perspective view of the lower positioning member of FIG. 1 but with a tissue specimen disposed over an at least partially elastically deformable portion thereof.
Figure 3:
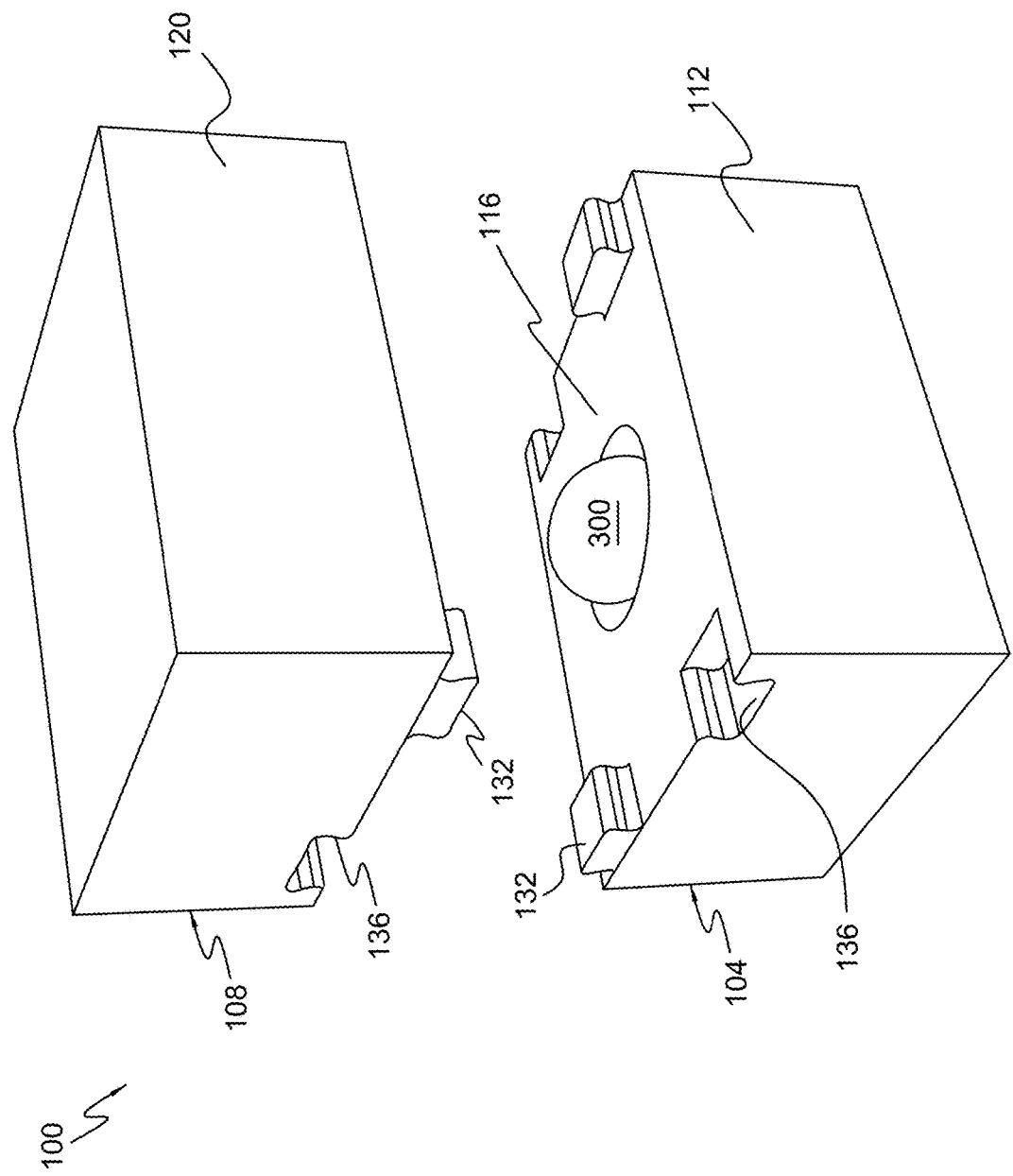
FIG. 3 illustrates the perspective view of the lower positioning member of FIG. 2 and with a second or upper positioning member disposed above the lower positioning member.

To further understand the various features and functionality of the apparatus 100, additional reference will now be made to FIG. 35 which illustrates a flow diagram of a method 800 for use in tissue abnormality diagnosis that may incorporate use of the apparatus 100. At 804, a surgeon may excise a particular tissue specimen from a patient (e.g., tissue specimen 300 shown in FIG. 2) that is believed to at least partially include cancer and/or one or more other abnormalities. The surgeon, other medical personnel, or machine may then non-movably retain and fix 808 the excised tissue specimen within the positioning apparatus 100. For instance, the surgeon may place the specimen 300 onto the elastically deformable portion 116 of the first positioning member 104 (e.g., such as generally over a central portion of the elastically deformable portion 116 as shown in FIG. 2), align the first and second connection members 132, 136 of the second positioning member 108 with the second and first connection members 136, 132 of the first positioning member 104 (see FIG. 3), elastically deform elastically deformable portions 116, 124 of the first and second positioning members 104, 108 about opposite portions of the specimen 300, and engage the respective pairs of first and second connection members 132, 136 to non-movably retain and fix 808 the excised tissue specimen within the specimen support volume of the positioning apparatus 100 (see FIGS. 4-5).

Figure 5:
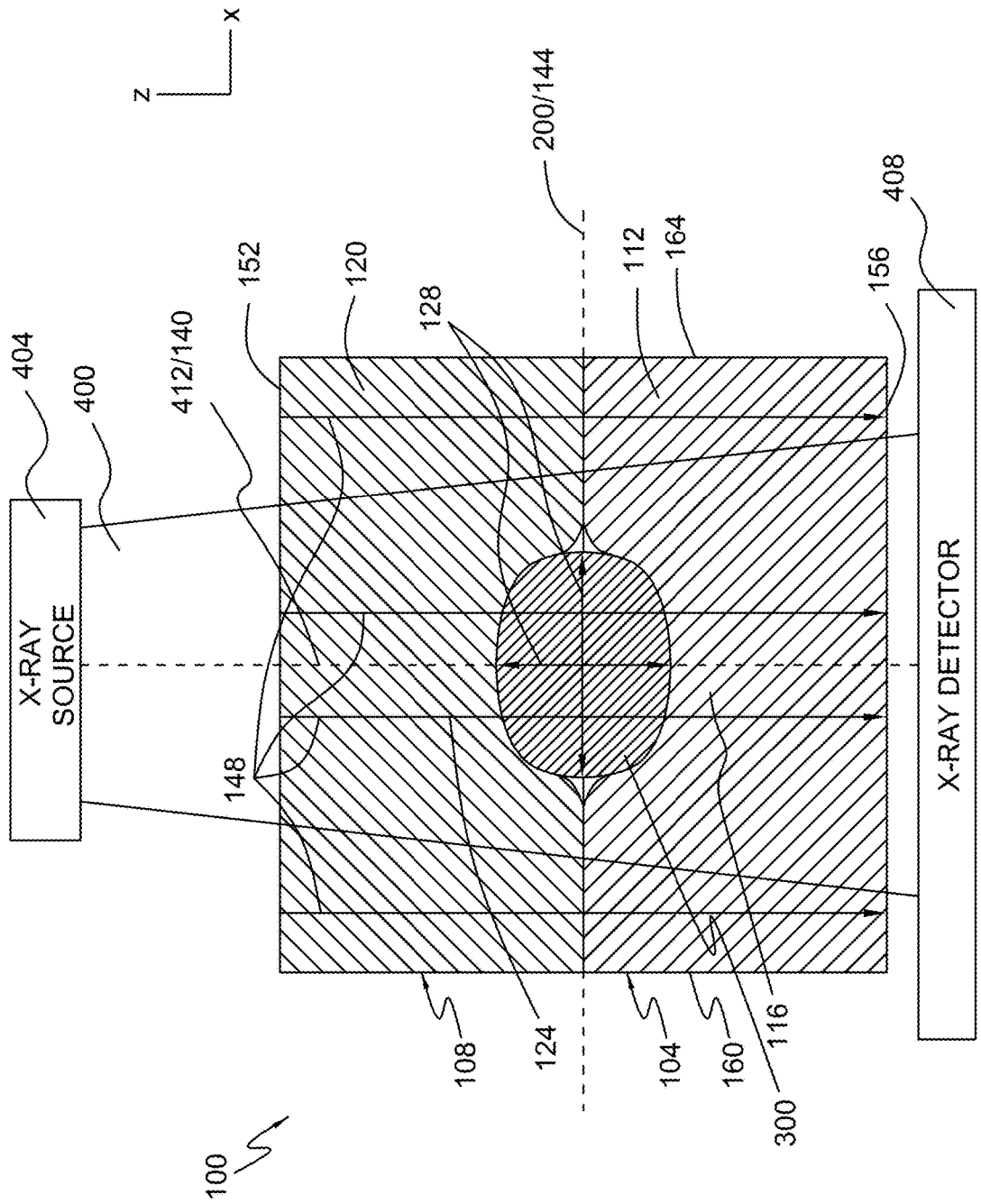
FIG. 5 is a sectional view through the apparatus and tissue specimen of FIG. 4 along the line 5-5 and illustrating an electromagnetic radiation signal being transmitted along a first axis through the apparatus and the tissue specimen to obtain a first image of the tissue specimen.

The method 800 may also include orienting 812 the positioning apparatus 100 at a first orientation relative to a support surface (e.g., horizontal surface, not shown) and then imaging 816 the specimen 300 along the first axis 140 through the apparatus 100 to obtain a first image of the specimen 300. With reference to FIG. 5, the apparatus 100 may be disposed along and/or about an imaging axis 412 of an imaging beam 400 between an x-ray (e.g., or other electromagnetic radiation) source 404 and an x-ray (e.g., or other electromagnetic radiation) detector 408 (e.g., sensor(s), film). For instance, the apparatus 100 may be positioned so that the imaging axis 412 is coincident with and/or substantially parallel to the first axis 140 through the apparatus, where the first axis 140 is substantially perpendicular to a reference plane 200 defined between the elastically deformable portions 116, 124 of the first and second positioning members 104, 108. Stated differently, the apparatus 100 may be positioned so that the imaging axis 412 is substantially perpendicular to the reference plane 200. In any event, the source 404 may generate and transmit an imaging signal 400 along imaging axis 412 and the first axis 140 through the apparatus 100, specimen 300 and specimen support volume 128 for receipt at detector 408 to generate a first image of the specimen 300.

Figure 4:
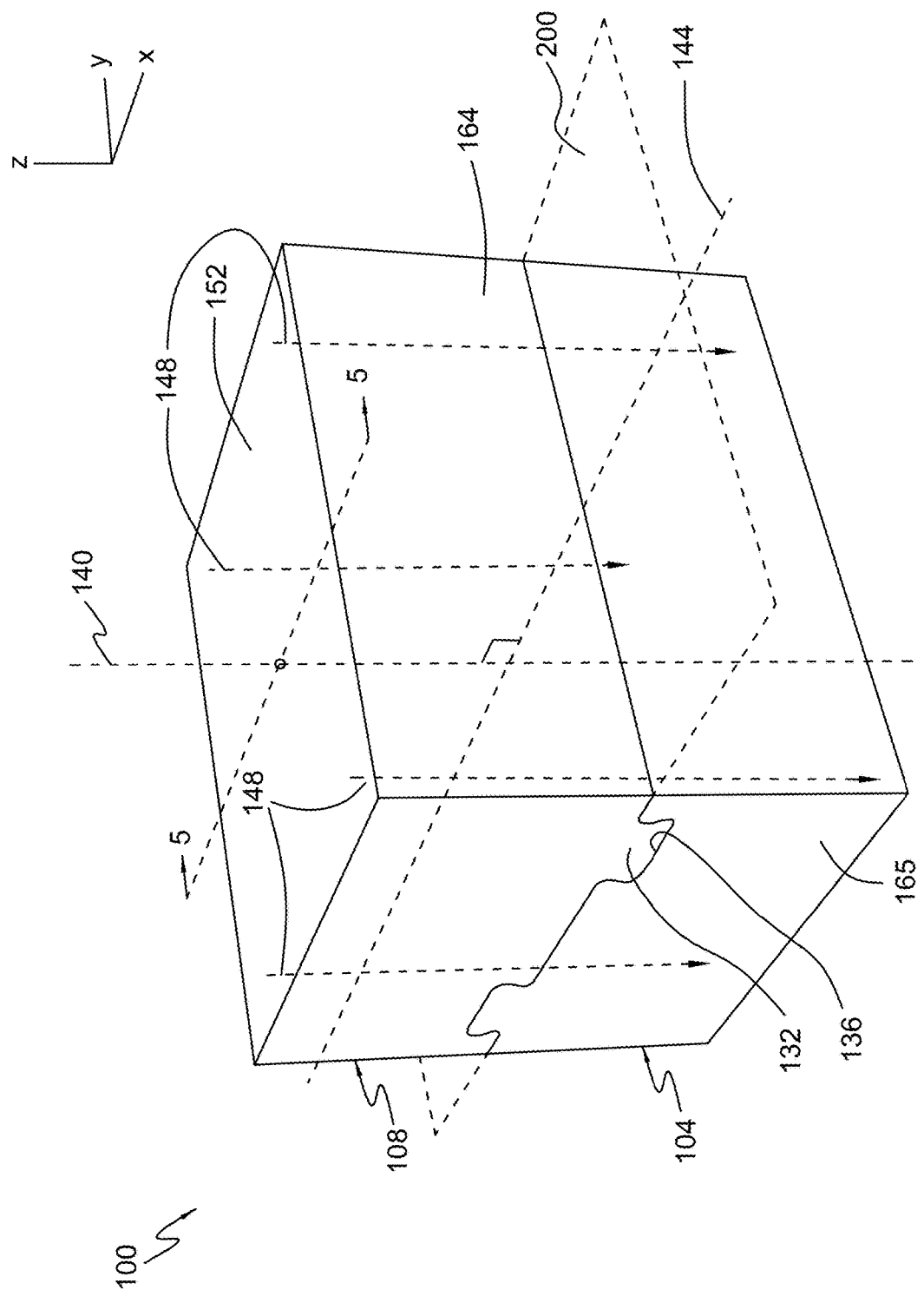
FIG. 4 shows the lower and upper positioning members being fixably positioned relative to each to retain the tissue specimen between the at least partially elastically deformable portions thereof, where the apparatus is in a first orientation relative to a support surface.

With reference to FIGS. 4-5, it is noted how the imaging signal 400 passes or propagates through a first volume 148 (e.g., first imaging zone or region) of the apparatus 100 that extends from a first external side 152 of the apparatus 100 to a second external side 156 of the apparatus 100 that is opposite to the first external side 152. More specifically, the first volume 148 extends along the first axis 140 (e.g., in a z dimension) and about the first axis 140 (e.g., in the x and y dimensions) and encompasses the specimen support volume 128. Furthermore, the first volume 148 is free of any portion having a density (e.g., radiodensity) greater than either a density (e.g., radiodensity) of the elastically deformable portion 116 of first positioning member 104 or a density (e.g., radiodensity) of the elastically deformable portion 124 of the second positioning member 108. In other words, an entire footprint of the imaging signal 400 is configured to pass through a volume (e.g., the first volume 148) of the apparatus 100 that has a density no greater than the densities of the elastically deformable portions 116, 124 of the first or second positioning members 104, 108 that coincide with the first volume 148 (e.g., whereby the first and second positioning members 104, 108 are constructed of a low-radiodensity solid foam or the like). In some arrangements, markings or other features may be provided on the support surface (not shown) that may be used to automatically orient the apparatus 100 so that an entirety or substantial entirety of the imaging signal 400 passes through the first volume 148.

In the embodiment of FIG. 5, an entirety of each of the first and second positioning members 104, 108 is constructed from a piece (e.g., block) of solid foam. In this regard, the first volume 148 extends between first and second opposite external sides 152, 156 of the apparatus 100 along an entirety of the distance between the third and fourth external sides 160, 164, and fifth external side 166 and sixth external side (not labeled, but opposite fifth external side 166). Stated differently, the first volume 148 encompasses the entirety of the apparatus 100 as an entirety of each of the first and second positioning members 104, 108 is constructed from a piece (e.g., block) of solid foam. However, the first volume 148 need not necessarily extend all of the way to the third and fourth external sides 160, 164 and/or all of the way to the fifth and sixth external sides 166 (sixth external side not labeled) so long as the first volume 148 extends entirely from the first external side 152 to the second external side 156 and at least partially towards the third and fourth external sides 160, 164 (e.g., in the x dimension) and the fifth and sixth external sides 166 (sixth external side not labeled) (in the y dimension) all along the second axis 144 so as to encompass the specimen support volume 128. As just one example, the first volume 148 may include at least 20% of a total volume occupied by the apparatus 100, such as at least 40%, or at least 60%.

In any event, an entirety (or substantial entirety) of the specimen 300 may advantageously be imaged along and about the first axis 140 substantially free of signal attenuation that may otherwise produce artifacts in the resultant image, other reductions in quality of the resultant image, and/or the like. This arrangement is in contrast to prior or existing specimen holding/positioning apparatuses or systems whereby the imaging signal 400 would pass through relatively higher radiodensity materials disposed along the reference plane 200 and/or imaging axis 412 during imaging of the specimen 300 (e.g., such as a plastic container within which the specimen is disposed; other objects, structures, supports, etc. within the path of the imaging signal 400, etc.) that can cause such undesired artifacts and image quality losses.

Figure 35:
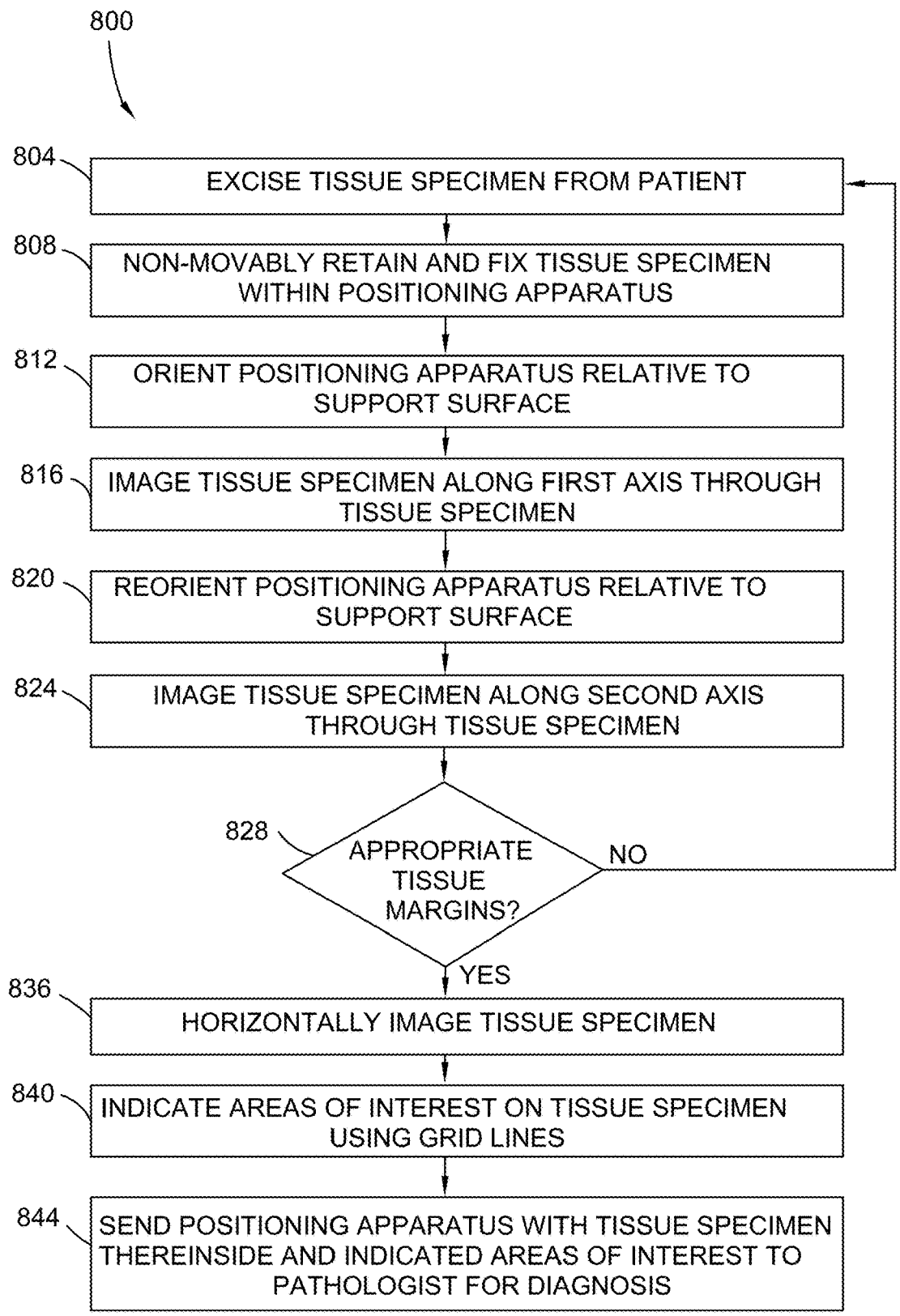
FIG. 35 is a flow diagram illustrating one method for use in tissue abnormality diagnosis.

With brief reference back to FIG. 35, the method 800 may include reorienting 820 the positioning apparatus 100 into a second orientation relative to the support surface (e.g., and the imaging axis 412) and then imaging 824 the specimen 300 along the second axis 144 through the apparatus 100 to obtain a second image of the specimen 300. For instance, the entire apparatus 100 may be pivoted or rotated by 90° (clockwise in this example about the y dimension) so that the third external side 160 of the apparatus 100 rests on the support surface (e.g., which may in one embodiment include aligning the third external side 160 with any markings or the like on the support surface). Advantageously, the specimen 300 may remain substantially fixed or non-movable within the apparatus 100 during the reorienting 820 (e.g., due at least in part to the first and second elastically deformable portions 116, 124) to increase the accuracy of subsequent imaging operations and analysis. In one arrangement, the specimen 300 may also be substantially non-deformably retained within the apparatus 100 (e.g., retained in a manner substantially free of experiencing changes to its natural shape and dimensions) to further increase the accuracy of subsequent imaging operations and analysis.

In the second orientation, the imaging axis 412 may be coincident with and/or substantially parallel to the second axis 144, where the second axis 144 is coincident with and/or substantially parallel to the reference plane 200 defined between the elastically deformable portions 116, 124 of the first and second positioning members 104, 108. Stated differently, the apparatus 100 may be positioned so that the imaging axis 412 is substantially coincident with or parallel to the reference plane 200. In any event, the source 404 may generate and transmit an imaging signal 400 along imaging axis 412, the second axis 140, and the reference plane 200 through the apparatus 100 and specimen 300 for receipt at detector 408 to generate a second image of the specimen 300 that is orthogonal to the first image.

Similar to imaging of the specimen 300 along the first axis 140 through the apparatus 100 and specimen 300, imaging of the specimen 300 along the second axis 144 through the apparatus 100 and specimen 300 passes or propagates through a second volume 168 (e.g., second imaging zone or region) of the apparatus 100 that extends from the third external side 160 of the apparatus 100 to the fourth external side 164 (e.g. along x dimension) of the apparatus 100, where the second volume 168 is free of any portion having a density (e.g., radiodensity) greater than either a density (e.g., radiodensity) of the elastically deformable portion 116 of the first positioning member 104 or a density (e.g., radiodensity) of the elastically deformable portion 124 of the second positioning member 108. See FIGS. 6-7.

More specifically, the second volume 168 extends along and about the second axis 144 (e.g., in the x dimension) and encompasses the specimen support volume 128. That is, an entire footprint of the imaging signal 400 is configured to pass through a volume (e.g., the second volume 168) of the apparatus 100 that has a density no greater than the densities of the elastically deformable portions 116, 124 of the first or second positioning members 104, 108 that coincide with the second volume 168 (e.g., whereby the first and second positioning members 104, 108 are constructed of a low-radiodensity solid foam or the like). As discussed above, markings or other features may be provided on the support surface (not shown) that may be used to automatically orient the apparatus 100 so that an entirety or substantial entirety of the imaging signal 400 passes through the second volume 168.

While the second volume 168 extends between third and fourth external sides 160, 164 of the apparatus (e.g., the x dimension) along an entirety of the distance between the first and second external sides 152, 156 (e.g., the z dimension) and fifth and sixth external sides 166 (sixth external side not labeled) (e.g., they dimension) due to the first and second positioning members being constructed entirely of solid foam in this embodiment, the second volume 168 need not necessarily extend all of the way to the first and second external sides 152, 156 and/or all of the way to the fifth and sixth external sides 166 (sixth external side not labeled) so long as the second volume 168 extends from the third external side 160 to the fourth external side 164 and at least partially towards the first and second external sides 152, 156 and the fifth and sixth external sides 166 (sixth external side not labeled) all along the second axis 144 so as to encompass the specimen support volume 128. As just one example, the second volume 168 may include at least 20% of a total volume occupied by the apparatus 100, such as at least 40%, or at least 60%.

The specimen 300 may thus be imaged along the reference plane 200 (e.g., where the imaging axis 412 is substantially coincident with or parallel to the second axis 144 and reference plane 200) substantially free of signal attenuation caused by components/supports/etc. having a radiodensity greater than that of the elastically deformable portions 116, 124 of the first and second positioning members 104, 108 that may otherwise be present along the imaging axis 412. The apparatus 100 advantageously allows a surgeon, other personnel, and/or the like to rapidly and easily place an excised specimen 300 onto a horizontally disposed surface (e.g., elastically deformable portion 116 of FIG. 3), retain and image the specimen 300 within the apparatus 100 along one axis (e.g., the first axis 140) to obtain a first image of the specimen 300 (see FIGS. 4-5), rotate the entire apparatus 100 by 90° (see FIG. 6), and then image the specimen 300 within the apparatus 100 along an orthogonal axis (e.g., the second axis 144) to obtain a second image of the specimen 300 (see FIG. 7).

Returning to FIG. 35, the method 800 may query 828 whether appropriate tissue margins have been detected in the specimen 300. For instance, a surgeon or radiologist may examine both of the first and second images to confirm that any appropriate tissue margins have been satisfied (e.g., whether any appropriate tissue margins surround the area(s) of interest within the specimen 300). In response to a negative answer to the query at 828, the method 800 may flow back to 804 to excise another tissue specimen, retain and fix 808 the specimen within a positioning apparatus (e.g., apparatus 100), and the like. While the method 800 has been discussed in the context of first imaging along the first axis 140 and then imaging along the second axis 144, it is also envisioned that the specimen 300 could first be imaged along the second axis 144 and then imaged along the first axis 140.

Figure 8:
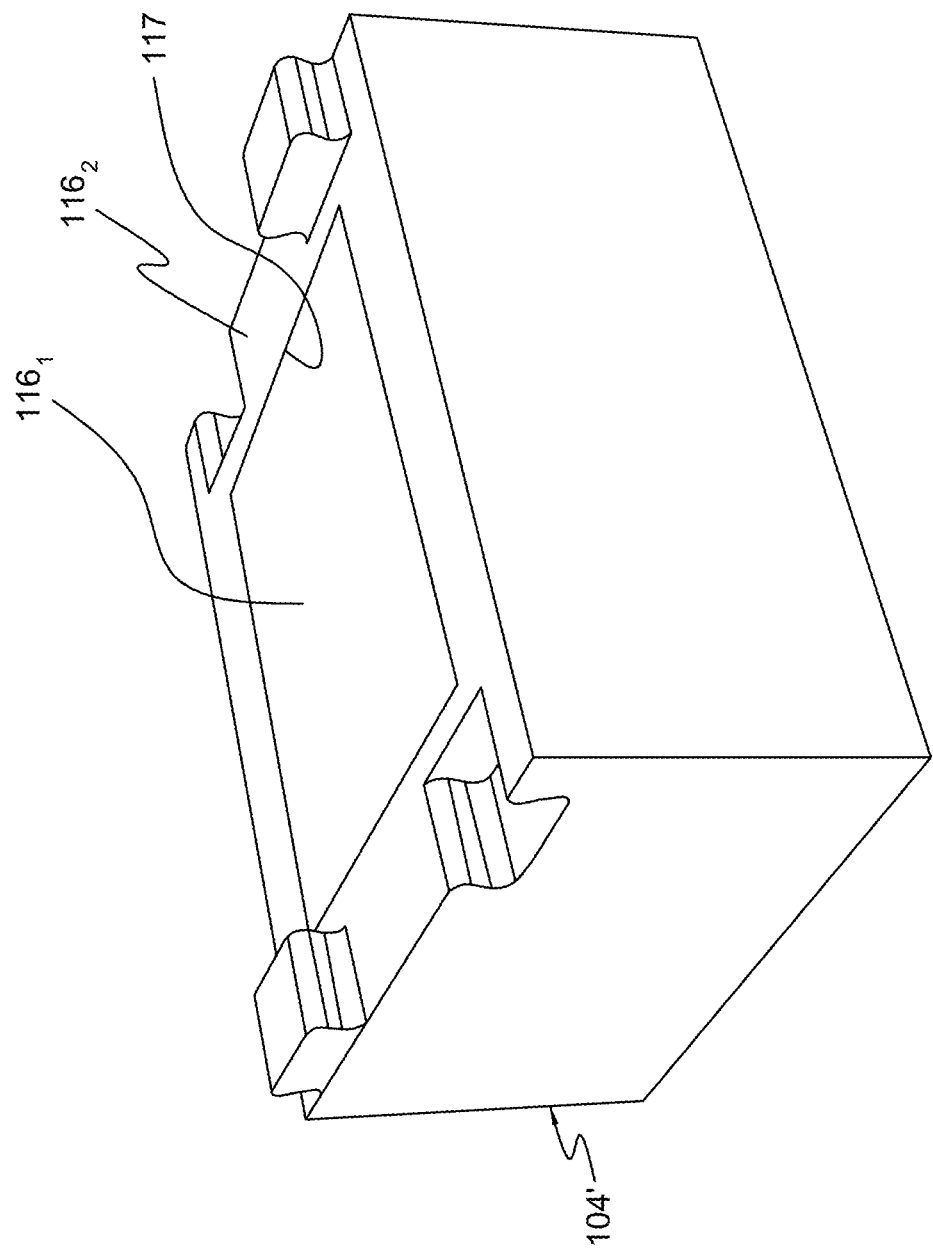
FIG. 8 is a perspective view of the lower positioning member of FIG. 1 according to another embodiment.

Before discussing further steps of the method 800, additional embodiments of the apparatus 100 will now be discussed. In FIG. 8, another embodiment of the first positioning member 104' is illustrated whereby the elastically deformable portion 116 is in the form of first and second at least partially elastically deformable portions $116_1$, $116_2$, where the second elastically deformable portion $116_2$ partially or fully surrounds the first elastically deformable portion $116_1$ and has a compression resistance greater than that of the first elastically deformable portion $116_1$. For instance, the first elastically deformable portion $116_1$ may be constructed of a relatively lighter and softer solid foam to reduce compression of a specimen 300 placed thereon while the second elastically deformable portion $116_2$ may be constructed of a relatively heavier and/or denser solid foam to maintain the structural integrity of the apparatus. As another example, the first elastically deformable portion $116_1$ may be constructed of a sheet or film (e.g., nonporous polyurethane film).

In one arrangement, the second elastically deformable portion $116_2$ may include an opening 117 (e.g., recess, depression, etc) in a surface thereof across, over, and/or within which the first elastically deformable portion $116_1$ may be disposed, positioned and/or inserted (e.g., removably or non-removably). Some variations disclosed herein envision that the first elastically deformable portion $116_1$ may be selected based on the type of specimen to disposed thereon or thereover for retainment within the apparatus 100. For instance, first elastically deformable portions $116_1$ of increasing compression resistance may be selected for specimens 300 of increasing compression resistance and vice versa. While not shown, the second positioning member 108 may also be similarly configured with first and second elastically deformable portions $116_1$, $116_2$ such that the specimen 300 may be elastically retained between the first elastically deformable portions $116_1$ of the first and second positioning members 104',108' for imaging along the first and second axes 140, 144 (e.g., as in FIGS. 4-7).

Figure 9:
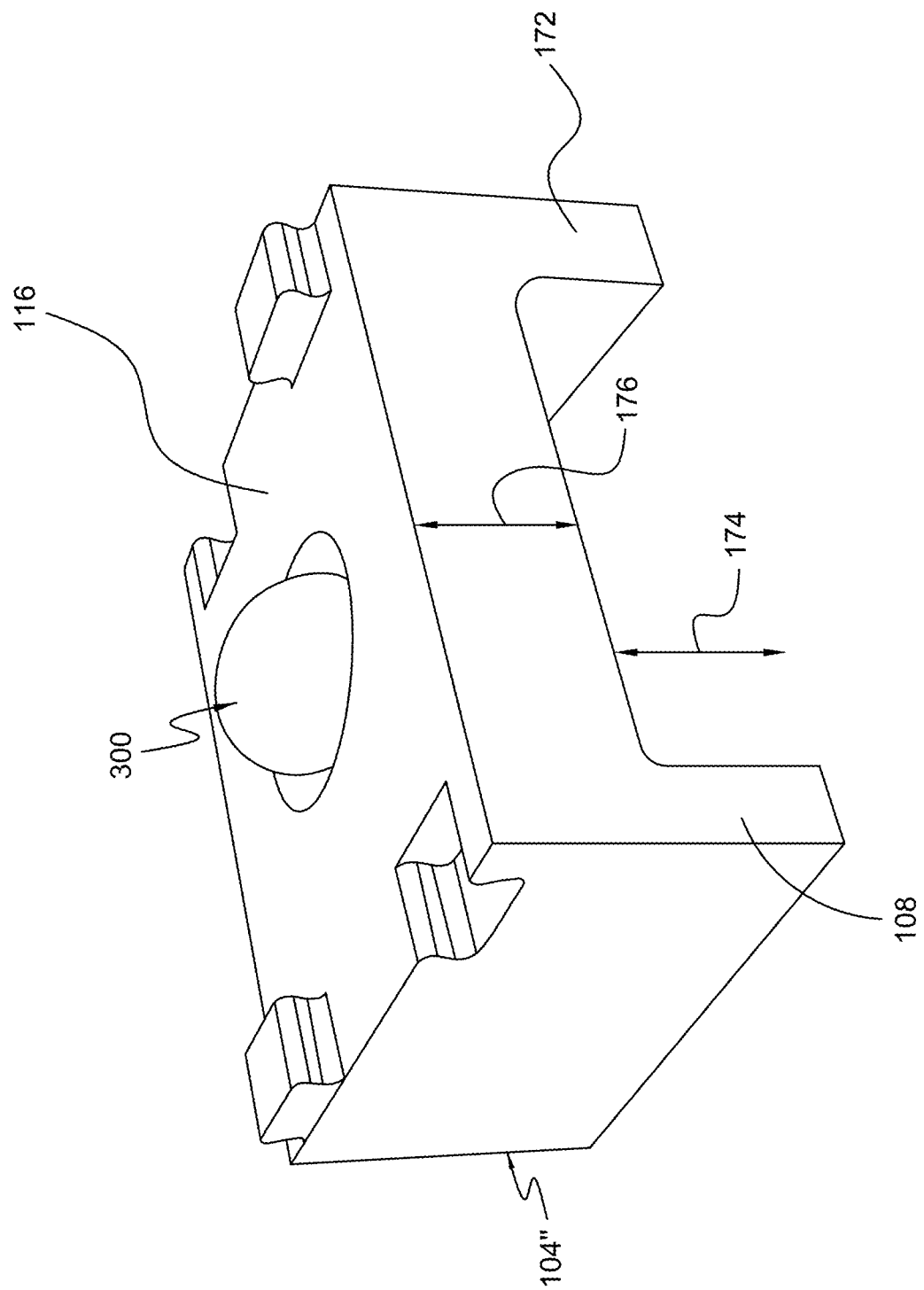
FIG. 9 is a perspective view of the lower and upper positioning members of FIG. 3 according to another embodiment.
Figure 10:
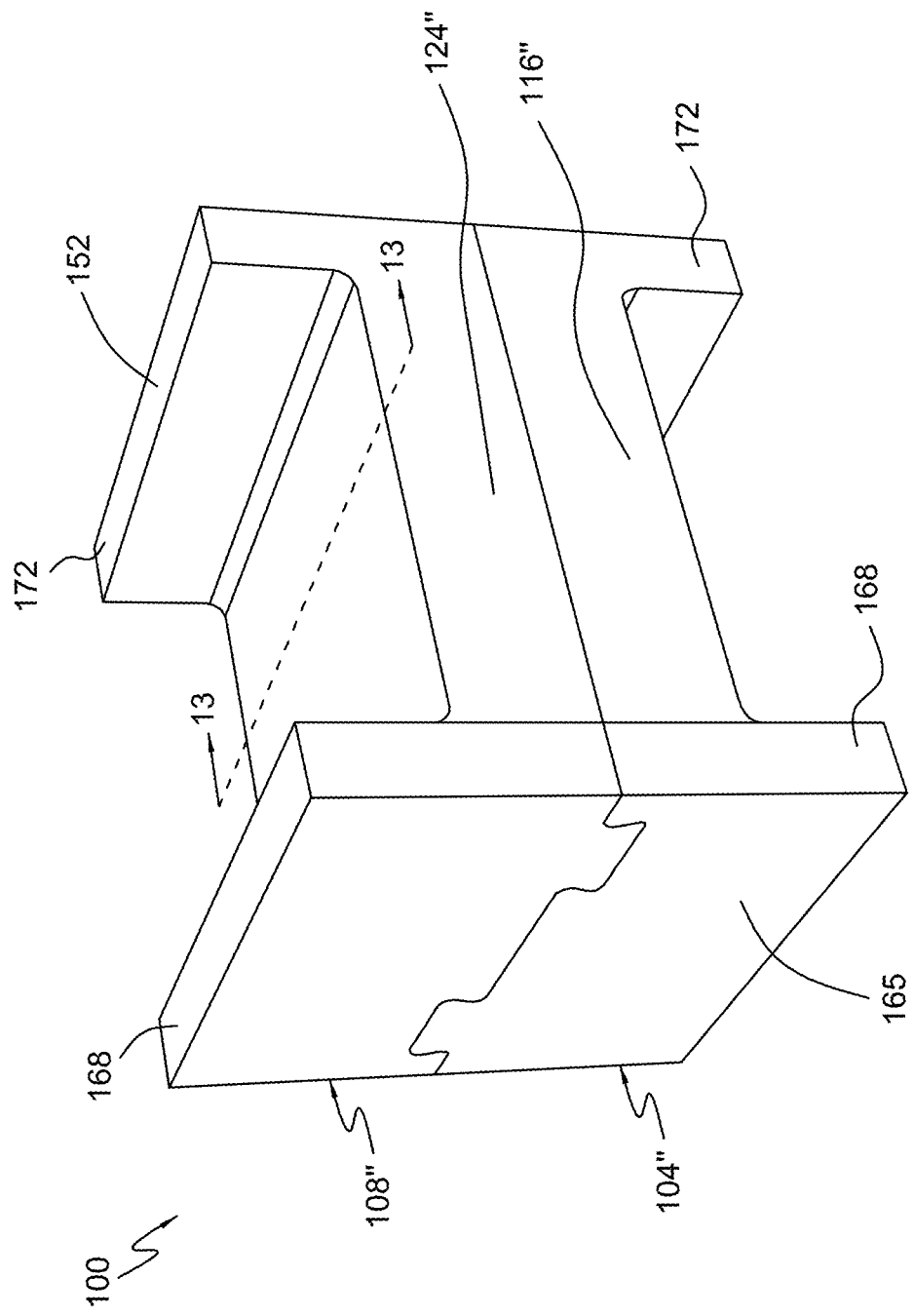
FIG. 10 is a perspective view similar to FIG. 9 but showing the lower and upper positioning members being fixably positioned relative to each other to retain a tissue specimen between at least partially elastically deformable portions thereof.
Figure 11:
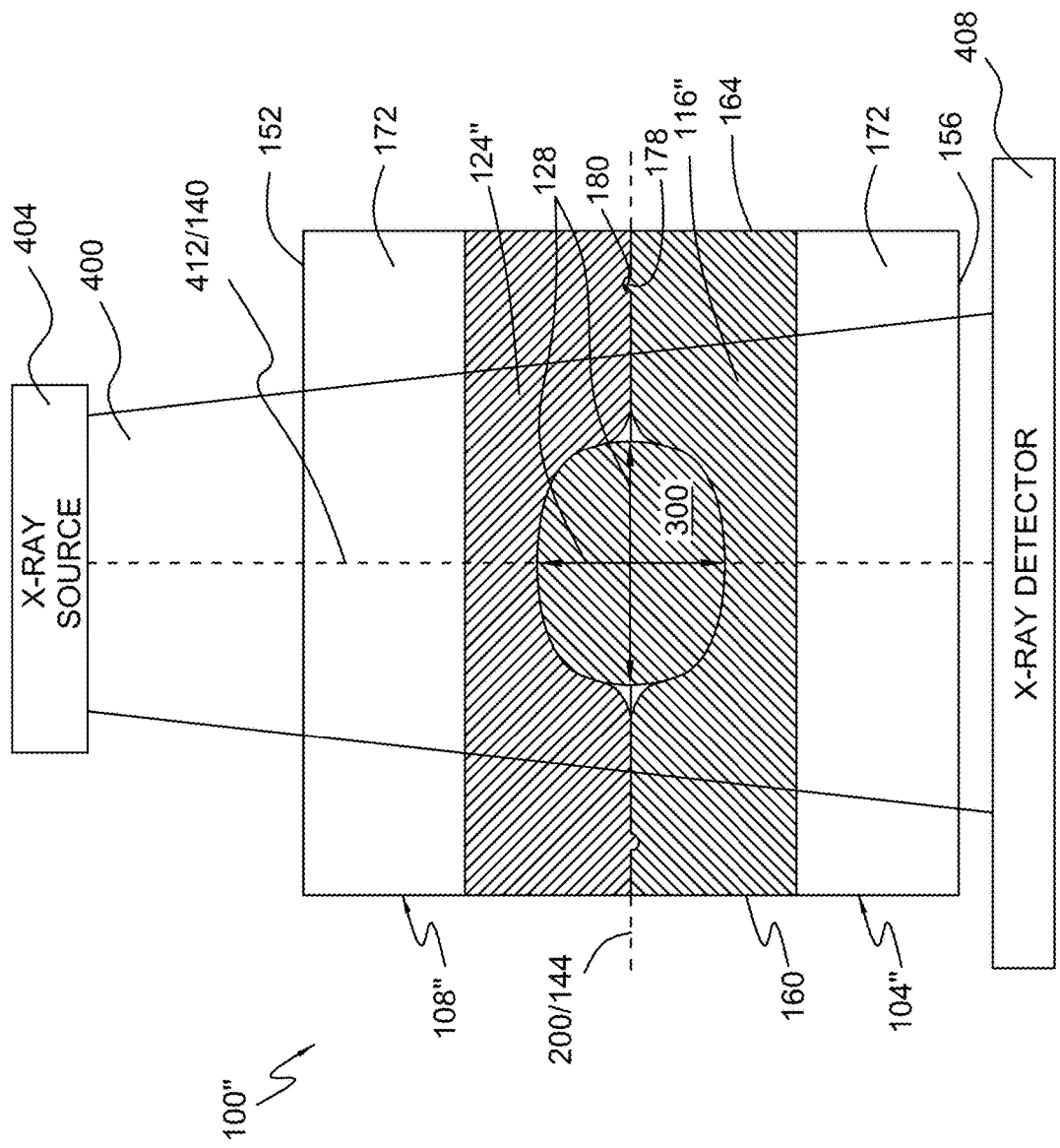
FIG. 11 is a perspective view of the lower positioning member of FIG. 1 according to another embodiment.

FIGS. 9-11 illustrate another embodiment of the apparatus 100" in which the first and/or second positioning members 104",108" include at least first and second support members 168, 172 extending relative to the elastically deformable portions 116, 124 (e.g., perpendicularly relative to a surface thereof that is configured to receive the specimen 300) for purposes of spacing the specimen 300 and the elastically deformable portions 116, 124 from the detector 408 (e.g., by distance 174) and reducing the quantity of material that the imaging signal must pass through between the source 404 and the detector 408. For instance, the In one arrangement, a thickness 176 of the elastically deformable portions 116, 124 may be selected or adjusted to control the firmness with which the elastically deformable portions 116, 124 hold and retain the specimen 300 when the first and second positioning members 104",108" are fixably positioned (e.g., where an increased thickness 176 would lead to greater firmness and vice versa). In another arrangement, the apparatus 100" (or, as with other features disclosed herein, with other apparatuses disclosed herein) may include at least one seal arrangement configured to limit leakage of fluids from the specimen support volume 128 out of the apparatus 100 and to limit entry of foreign objects and fluids into the specimen support volume 128. For instance, at least one of the elastically deformable portions 116, 124 may include a first seal member 178 (e.g., rib, rim, protrusion, etc.) and at least one of the other of the elastically deformable portions 116, 124 may include a second seal member 180 that is complimentary to the first seal member 178 (e.g., such as a recess, channel, etc. that is configured to matingly receive the rib, rim, protrusion, etc.).

Returning now to FIG. 35, the method 800 may, in the event that the tissue margins have been verified at 828, include horizontally (e.g., so that the reference plane 200 is substantially parallel to a support surface) imaging 836 the specimen 300 through any appropriate grid member including any appropriate radiopaque lines, indicia, or the like so that the grid lines/indicia appear in the resulting image. The surgeon may then appropriately indicate 840 the areas of interest on the tissue specimen using the grid lines to inform the pathologist the location(s) of the most suspicious areas in the resulting image (e.g., by providing coordinates, marking directly on the image, etc.). The resulting image and excised tissue specimen may then be sent 844 to the pathologist for performing a diagnostic procedure and providing a diagnostic opinion.

Figure 6:
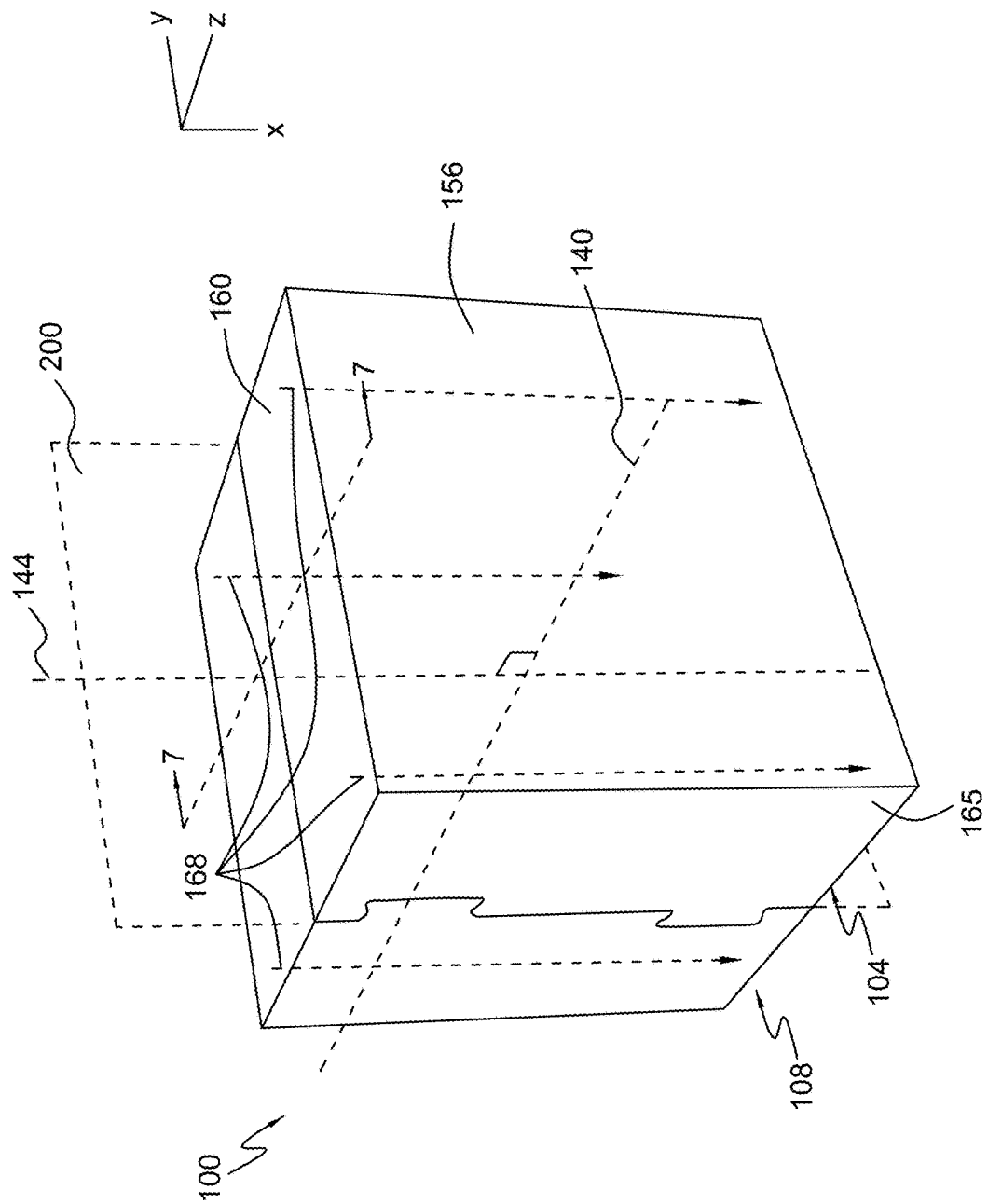
FIG. 6 shows the lower and upper positioning members being fixably positioned relative to each to retain the tissue specimen between the at least partially elastically deformable portions thereof, where the apparatus is in a second orientation relative to the support surface that is 90° relative to the first orientation.
Figure 7:
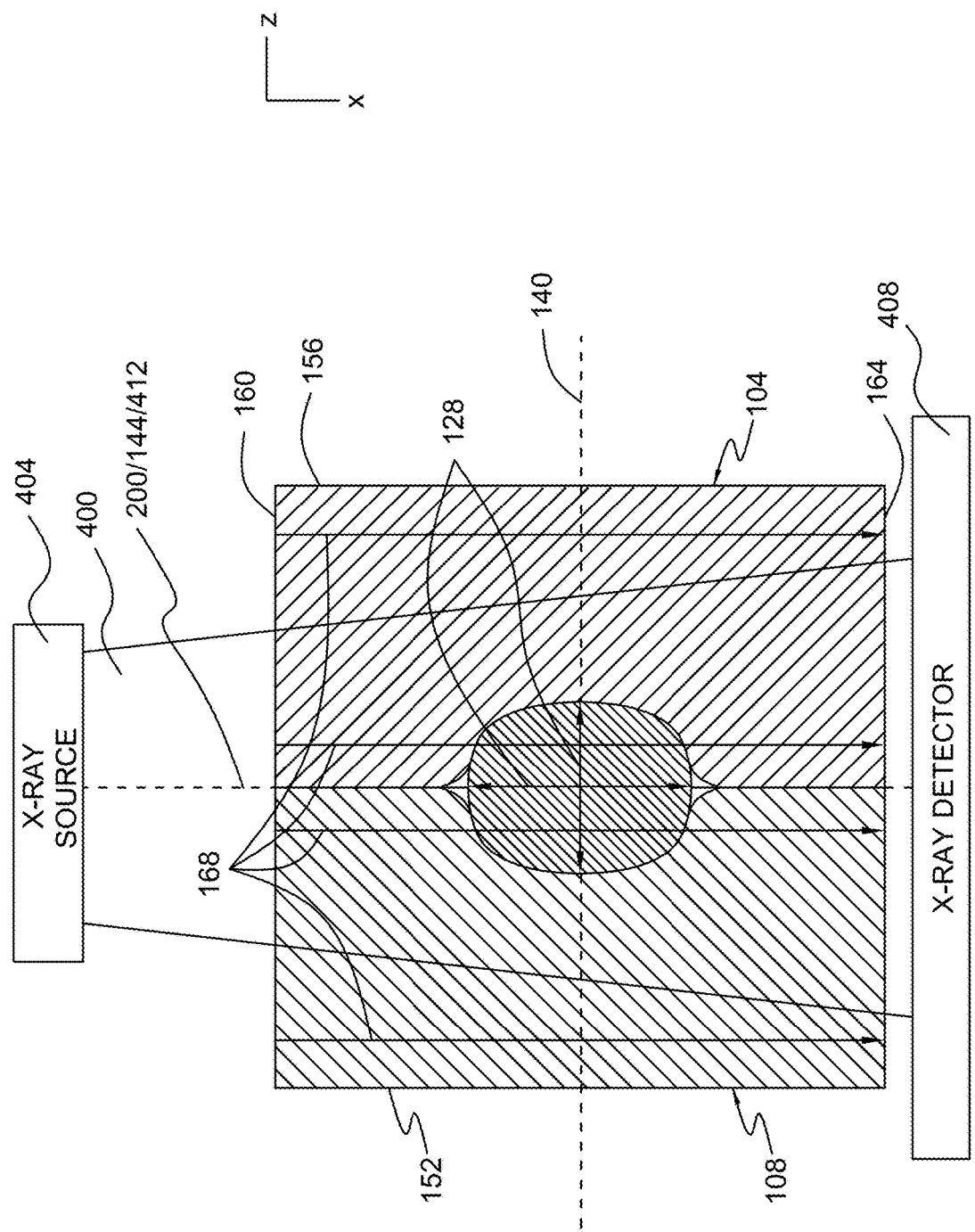
FIG. 7 is a sectional view through the apparatus and tissue specimen of FIG. 6 along the line 7-7 and illustrating an electromagnetic radiation signal being transmitted along a second axis through the apparatus and the tissue specimen to obtain a second image of the tissue specimen.
Figure 12:
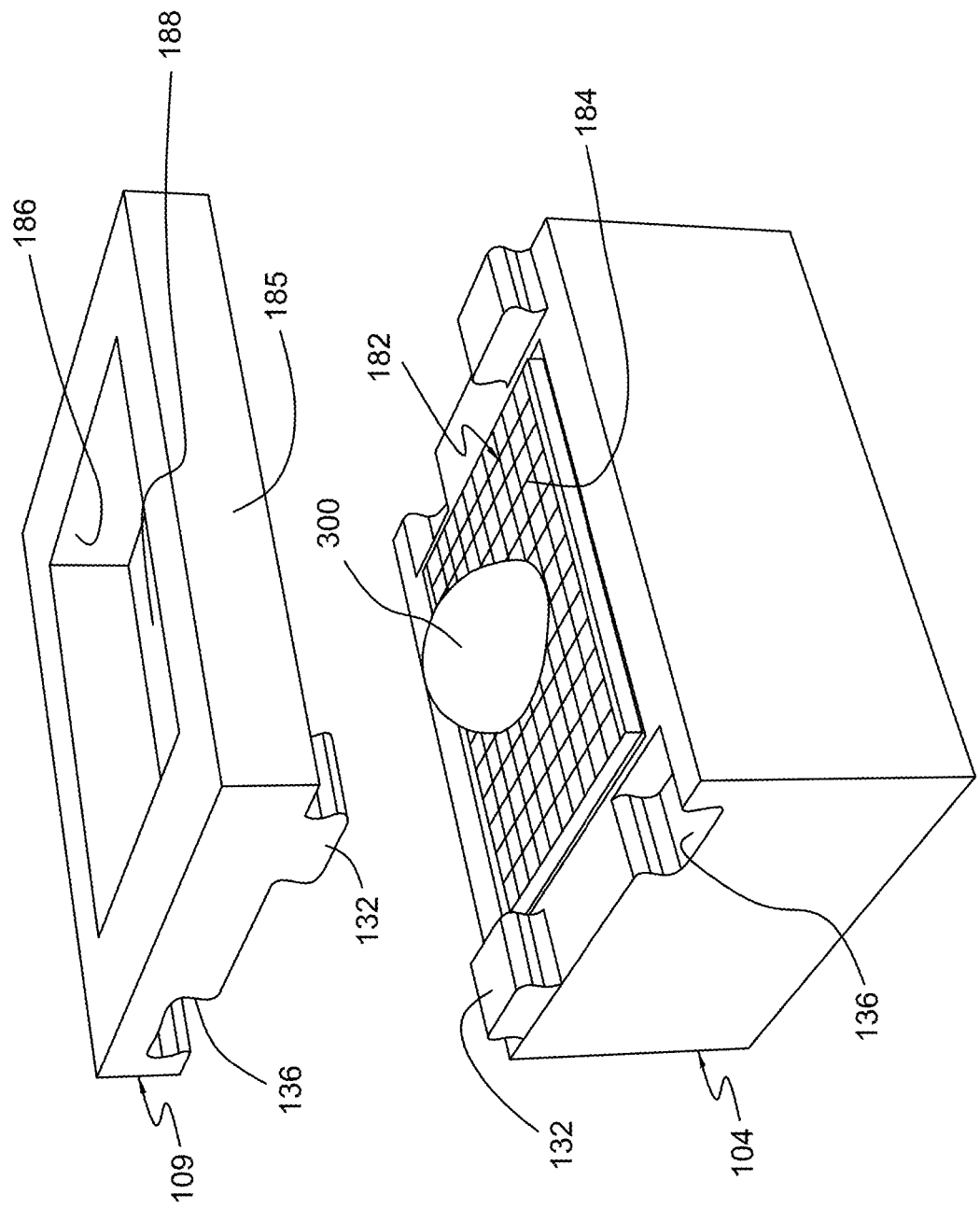
FIG. 12 is a perspective view of the lower positioning member of FIG. 11 being fixably positioned relative to an upper positioning member to retain a tissue specimen between at least partially elastically deformable portions thereof.

With reference to FIG. 6, for instance, the apparatus 100 may be rotated in an opposite direction to again place the second external side 156 of the apparatus 100 on the support surface (e.g., as in FIG. 4). After separation of the second positioning member 108 from the first positioning member 104, the specimen 300 may be removed from the elastically deformable portion 116 of the first positioning member 104, a grid member 182 (e.g., constructed of a radiolucent foam board or the like) may be placed onto the first sheet member 120 over the first opening 116, and the specimen 300 may be placed onto the grid member 182. See FIG. 12. The second positioning member 108 (not shown in FIG. 12) may then be interconnected with the first positioning member 104 (i.e., the apparatus 100 may be closed) as discussed previously to at least partially deform the elastically deformable portions 116, 124 about the grid member 182 and specimen 300, respectively, and non-movably secure the same within the apparatus 100. The apparatus 100 may then be imaged (e.g., with the second external side 156 of the apparatus 100 on the support surface and with the reference plane 200 parallel to the support surface and perpendicular to the imaging axis 412) to obtain one or more images having radiopaque grid lines 182 of the grid member 180 imparted into the images for use by the surgeon, a pathologist, etc.

In one arrangement, the second positioning member 108 may be replaced with an at least partially transparent positioning member 109 (see FIG. 12) that, like the second positioning member 108, is configured to fixably interconnect with the first positioning member 104 to retain the specimen 300 against movement relative to the apparatus 100 during imaging and transport. The positioning member 109 allows a surgeon or the like to view the specimen 300 before and during the horizontal imaging of the specimen 300. For instance, the positioning member 109 may include a frame 185 constructed of any appropriate material (e.g., solid foam like the second positioning member 108), thermoplastic, etc.) and including first and second connection members 132, 136 that are respectively configured to interface with those of the first positioning member 104.

Figure 13:
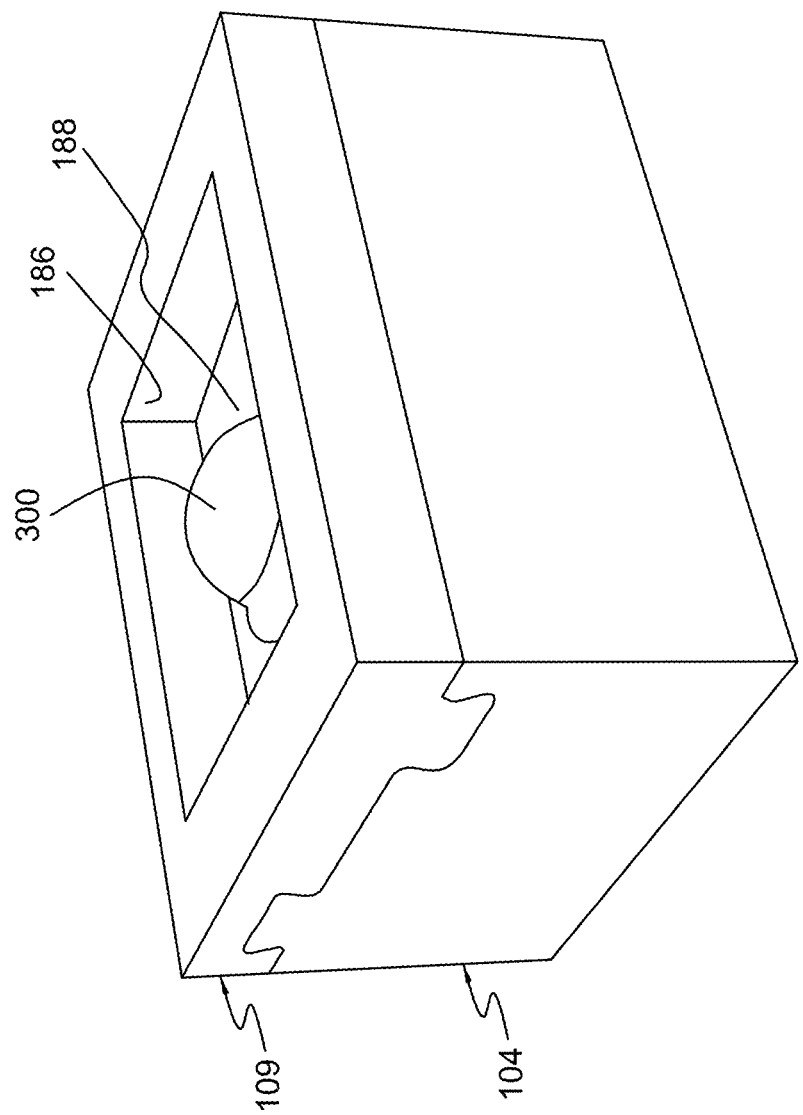
FIG. 13 is a sectional view through the apparatus and tissue specimen of FIG. 12 along the line 13-13 and illustrating an electromagnetic radiation signal being transmitted along an axis through the apparatus and the tissue specimen to obtain an image of the tissue specimen.
Figure 14:
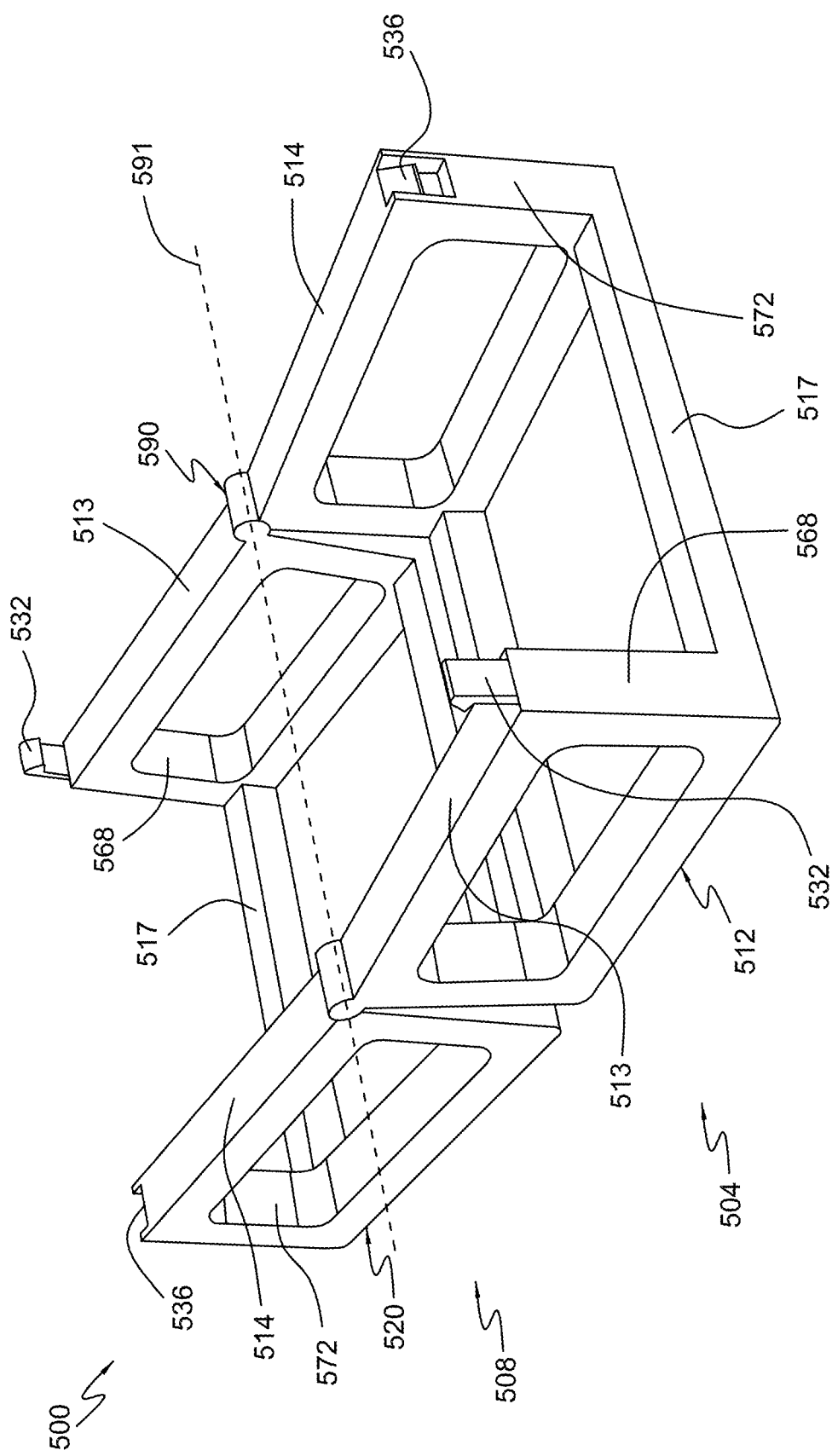
FIG. 14 is a perspective view of a specimen holding apparatus according to another embodiment, in an open orientation.
Figure 15:
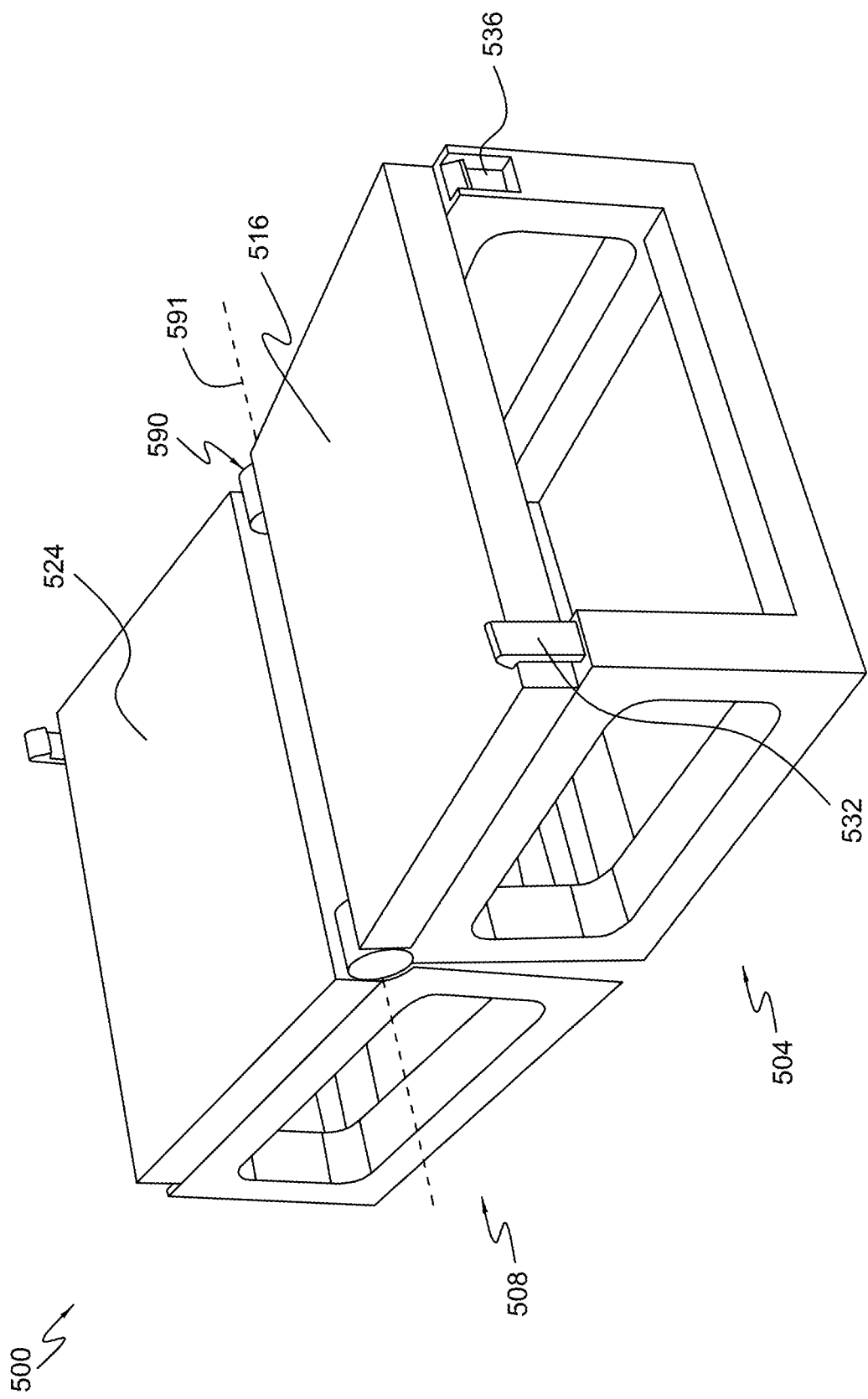
FIG. 15 is a perspective view similar to FIG. 14, but additionally illustrating at least partially elastically deformable portions of lower and upper positioning members of the apparatus.

The frame 185 may include an opening 186 therethrough that is configured to substantially overlap with the grid member 184 and/or with the elastically deformable portion 116 of the first positioning member 104. An at least partially elastically deformable transparent sheet or film 188 may be disposed across the opening 186 (e.g., attached over a bottom portion of the opening 186) that is configured to elastically deform around at least a portion of the specimen 300 when the positioning member 109 and the first positioning member 104 are interconnected. See FIG. 13. An imaging signal 400 may then be passed through the opening 186 to obtain an image of the specimen 300.

After obtaining the horizontal image of the specimen 300 at 836, the method 800 may include indicating 840 areas of interest on the specimen 300 using the grid lines present in the resulting horizontal image. For instance, the surgeon and/or radiologist may examine the resulting horizontal image and highlight and/or write down those grid line coordinates associated with areas of interest. The positioning apparatus 100 with the specimen 300 retained thereinside (e.g., in substantially the same position/orientation within the apparatus 100 as when the specimen was placed into the apparatus 100 and the indicated areas of interest (e.g., directly on the resulting horizontal image and/or the like) may then be sent 844 to a pathologist or the like for diagnosis of the specimen 300. As the specimen 300 may remain in substantially the same position/orientation relative to the grid member 182 from the time of horizontal imaging up to and including diagnosis by the pathologist (e.g., due to the first and second positioning members 104, 108 and/or first positioning member 104 and transparent positioning member 109 as discussed previously), which may include transport of the apparatus 100 from a first location to a second location, a substantially high correspondence between areas of interest identified on the resulting horizontal image and corresponding areas on the actual specimen 300 may be obtained leading to greater accuracy of cancer and/or other tissue abnormality diagnosis.

FIGS. 14-20 illustrate another embodiment of the apparatus 100 and the reference numeral 500 has been used to identify the embodiment of FIGS. 14-20 (e.g., rather than 100'" or the like) in the interest of clarity, and similar reference numerals (e.g., 104 in FIGS. 3 and 504 in FIG. 15 to indicate a first positioning member) have been used to the extent possible. Broadly, the apparatus 500 includes a first or lower positioning member 504 having a body 512 and an at least partially elastically deformable portion 516 (e.g., a "retention" portion or member), and a second or upper positioning member 508 having a body 520 and an at least partially elastically deformable portion 524 (e.g., a "retention" portion or member). Upon placement of at least one specimen 300 (see FIG. 16) over the elastically deformable portion 516 of the first positioning member 504 and then non-movable or fixed securement of the second positioning member 508 to the first positioning member 504, the elastically deformable portions 516, 524 of the first and second positioning members are respectively configured to elastically deform about opposite portions of the specimen 300 to thereby retain the specimen 300 therebetween within a specimen support volume 528 of the apparatus 500 (see FIG. 18) and suspend the specimen 300 within the bodies 512, 520 of the first and second positioning members 504, 508 (e.g., so that the specimen can "float" within a first volume 548 of the apparatus) for use in accurate imaging of the specimen, transport of the specimen and the like.

As shown, the body 512 of the first positioning member 504 may include first and second spaced opposite support ledges 513, 514 over which opposite ends of the elastically deformable portion 516 are configured to be appropriately secured (e.g., via adhesives, bonding, or the like). The body 512 may also include one or more first and second support members 568, 572 extending relative to the elastically deformable portion 516 and the first and second support ledges 513, 514 (e.g., perpendicularly) for purposes of spacing the specimen 300 and the elastically deformable portion 516 from the detector 408 (e.g., by distance 174) and reducing the quantity of material that the imaging signal 400 must pass through between the source 404 and the detector 408. The body 512 may also include one or more interconnection members 517 that rigidly interconnect respective pairs of first and second support members 568, 572. Collectively, the support ledges 513, 514, support members 568, 572, and interconnection members 517 form a frame of the first positioning member 504. Similarly, the body 520 of the second positioning member 508 includes first and second spaced opposite support ledges 513, 514, one or more first and second support members 568, 572, and one or more interconnection members 517, all of which collectively form a frame of the second positioning member 508.

The apparatus 500 includes one or more features that allow for fixable positioning of the first and second positioning members 504, 508 to allow for substantial non-movable retaining of the specimen 300 between the elastically deformable portions 516, 524 as well as suspension of the specimen 300 within the apparatus 500. In one arrangement, the apparatus 500 may include any appropriate hinge mechanism 590 that allows for pivotal movement between the first and second positioning members 504, 508 about a pivot axis 591. For instance, the first and second positioning members 504, 508 may include respective first and second hinge elements (not labeled) that are secured to or at least partially form the hinge mechanism 590. The hinge mechanism 590 may allow for relative positioning between the elastically deformable portions 516, 524 of the first and second positioning members 504, 508 between a number of positions, such as at least an open position (e.g., as in FIGS. 15-16) that allows for placement of the tissue specimen 300 between the elastically deformable portions 516, 524 and a closed position (e.g., as in FIGS. 17-20) that holds the tissue specimen 300 between the elastically deformable portions 516, 524 against movement relative to the frames of the first and second positioning members 504, 508.

Additionally or alternatively, the first and second positioning members 504, 508 may each include at least one respective connection member such as first and second connection members 532, 536 that are respectively configured to engage with the second and first connection members 536, 532 of the other of the first and second positioning members 504, 508. More particularly, each first connection member 532 of one of the first and second positioning members 504, 508 may be complimentary and removably connectable to a respective second connection member 536 of the other of the first and second positioning members 504, 508 to fixedly position the first and second positioning members 504, 508 relative to each other. In one embodiment, each of the first and second positioning members 504, 508 may include at least one first connection member 532 and at least one second connection member 536 adjacent respective first and second external sides of the apparatus 500.

For instance, each first connection member 532 may be in the form of a protrusion (e.g., tab, post, detent, etc.) and each second connection member 536 may be in the form of a complimentary-shaped and sized recess (e.g., opening, hole, detent, etc.). In one embodiment, the first connection members 532 may be snapped past and/or deformed into the second connection member 536. For instance, the first connection member 532 may be a flexible or resilient tab that is configured to snap into, snap past or otherwise engage with a corresponding second connection member 536 in the form of an opening, ledge or the like. In this regard, each first connection member 532 may be lifted or otherwise moved away from its respective second connection member 536 to allow for separation of the first and second positioning members 504, 508. Various other forms of first and second connection members 532, 536 are envisioned and encompassed herein.

As discussed in relation to other embodiments disclosed herein, each of the elastically deformable portions 516, 524 of the first and second positioning members 504, 508 is configured to at least partially transmit an imaging signal (e.g., electromagnetic radiation signal, such as an x-ray) therethrough to allow for imaging of the specimen 300 along first and second orthogonal axes 540, 544 through the apparatus 500 (e.g., including through the specimen support volume 528) to obtain respective first and second images of the specimen (e.g., for use in specimen margin verification and the like). Additionally, each of the elastically deformable portions 516, 524 is configured to at least partially elastically deform about an opposite portion of a specimen 300 to retain the specimen within the apparatus 500 when the first and second positioning members 504, 508 are non-movable secured to each other (e.g., see FIG. 18).

In one arrangement, each of the elastically deformable portions 516, 524 may be constructed of a sheet, layer, etc. of any appropriate radiolucent solid (e.g., polymeric) foam(s) (e.g., as discussed previously in relation to the apparatus 100). See apparatus 500 of FIGS. 15-20. As just one example, the thickness of one or both of the elastically deformable portions 516, 524 in the form of a solid foam may be greater than about 0.1" such as greater than about 1", or greater than about 2". In another arrangement, each of the elastically deformable portions 516, 524 may be constructed of a sheet, layer, etc. of any appropriate radiolucent film (e.g., polyurethane, etc.). See apparatus 500' of FIGS. 21-26. As just one example, the thickness of one or both of the elastically deformable portions 516, 524 in the form of a film may be greater than about 0.001 such as greater than about 0.002". For instance, the film could be bonded onto the support ledges 513, 514 during production or the frames of the first and second positioning members 504, 508 could be reusable and the film added by the customer and disposed of after each single use. As another example, some arrangement envision including a pre-applied adhesive along the front and back edges of the film to limit sliding/movement of the specimen 300 when the apparatus 500, 500' is reoriented (e.g., rotated). In some arrangements, one or both of the elastically deformable portions 516, 524 may include combinations of film and foam (e.g., parallel layers of a film and a solid foam).

As also discussed herein, the material properties (e.g., compression resistance, modulus of elasticity, etc.) and/or dimensions (e.g., thickness) of the elastically deformable portions 516, 524 of the first and second positioning members 504, 508 may be selected to retain the specimen 300 within the specimen support volume 528 of the apparatus 500 against movement relative to the apparatus 500 (e.g., relative to the frames of the first and second positioning members 504, 508). In one arrangement, the material properties and/or dimensions of the elastically deformable portions 516, 524 may be selected or configured to substantially inhibit deformation of the specimen 300 from its natural shape and dimensions while still retaining the specimen 300 against movement relative to the apparatus 500.

Figure 16:
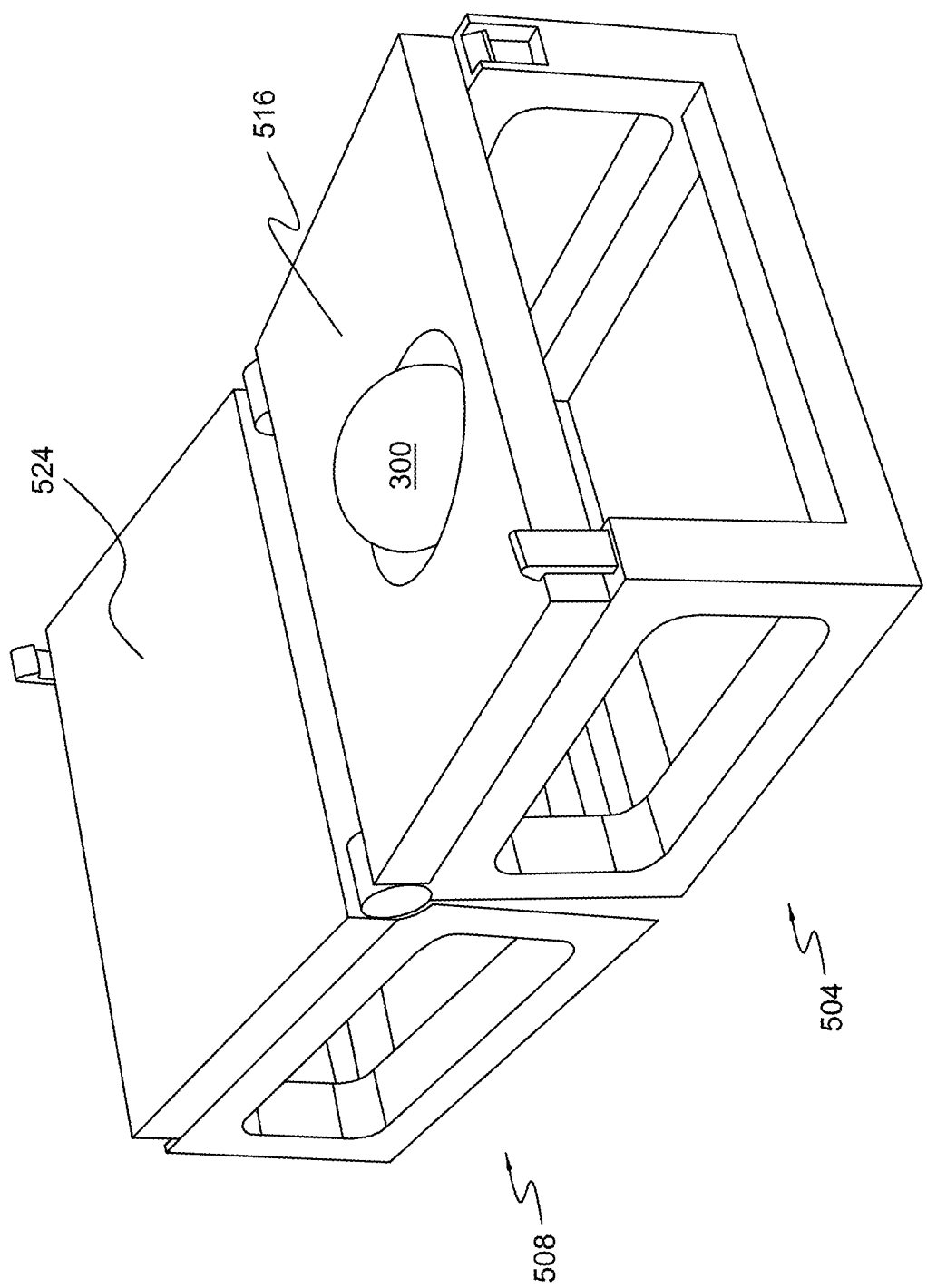
FIG. 16 is a perspective view similar to FIG. 15 but with a tissue specimen disposed over an at least partially elastically deformable portion of a lower positioning member of the apparatus.
Figure 17:
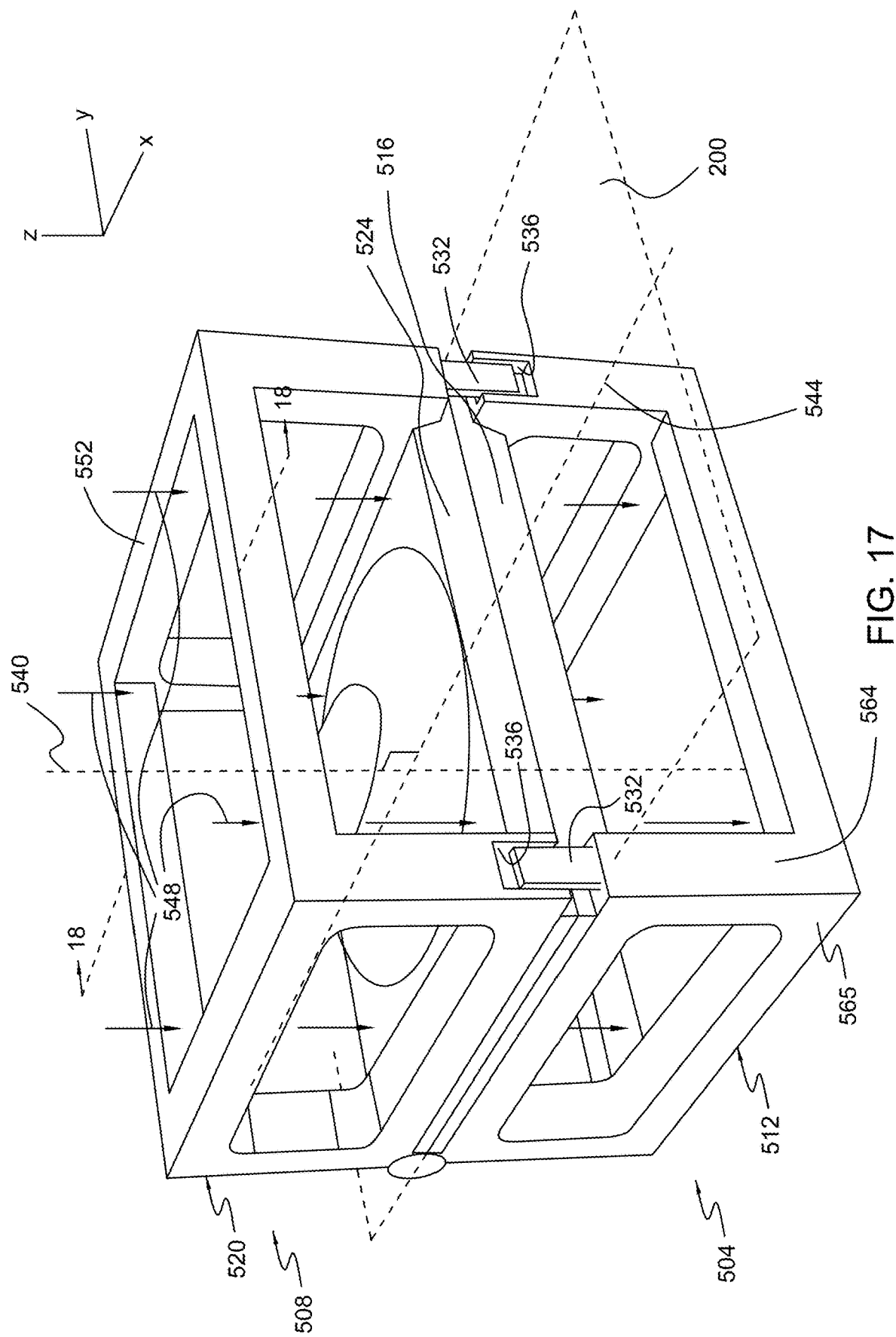
FIG. 17 is a perspective view of the apparatus of FIG. 15 in a closed position so that at least partially elastically deformable portions of upper and lower positioning members of the apparatus retain the tissue specimen therebetween, where the apparatus is in a first orientation relative to a support surface.
Figure 22:
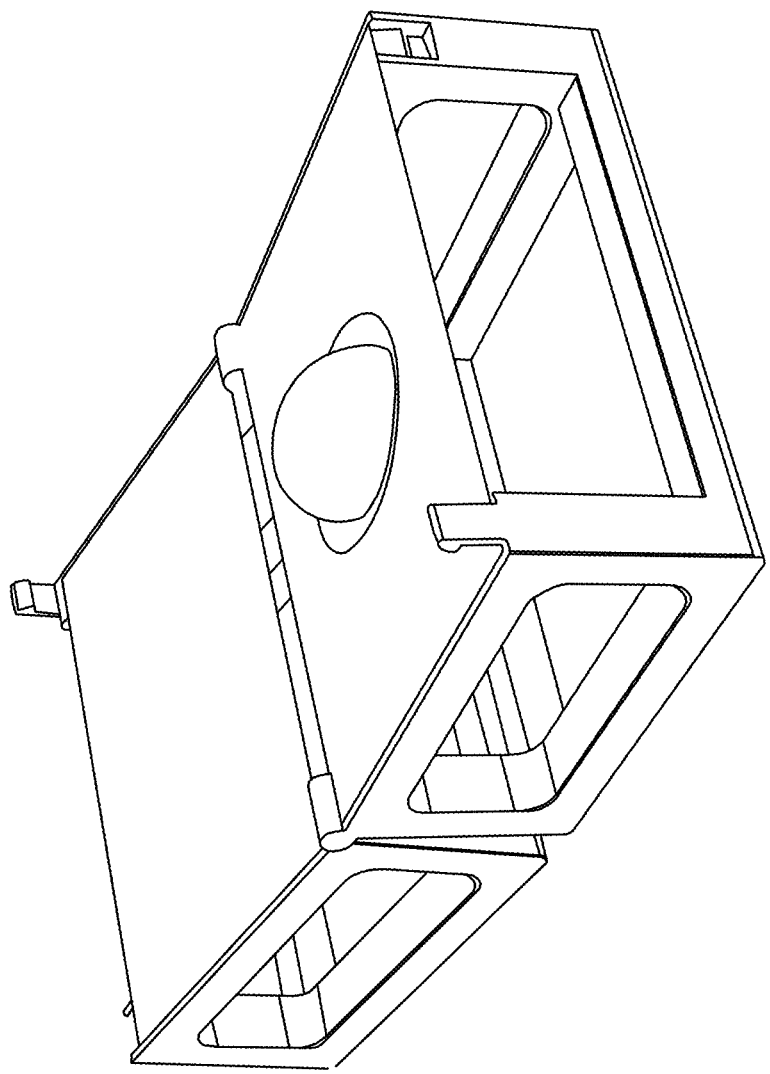
FIG. 22 is a perspective view similar to FIG. 21 but with a tissue specimen disposed over the at least partially elastically deformable portion of a lower positioning member of the apparatus.
Figure 23:
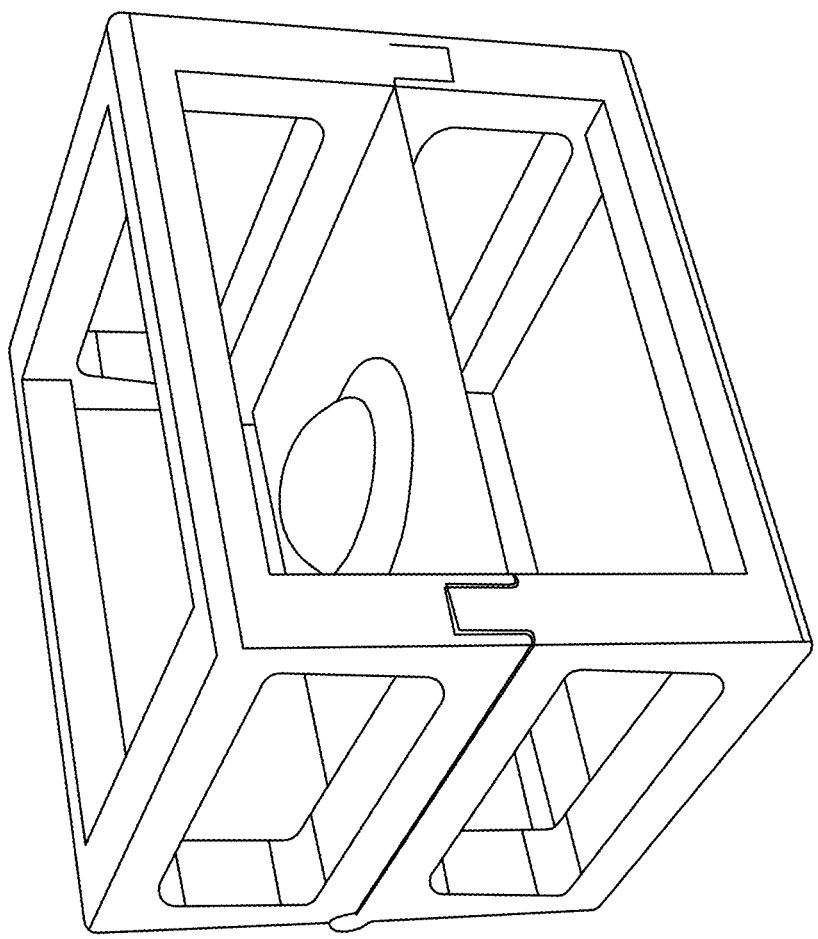
FIG. 23 is a perspective view of the apparatus of FIG. 22 in a closed position so that the at least partially elastically deformable portions of upper and lower positioning members of the apparatus retain the tissue specimen therebetween, where the apparatus is in a first orientation relative to a support surface.

Returning again to the method 800 of FIG. 35, a surgeon may excise 804 a particular tissue specimen from a patient (e.g., tissue specimen 300 shown in FIGS. 16 and 22) that is believed to at least partially include cancer and/or one or more other abnormalities. The surgeon, other medical personnel, or machine may then non-movably retain and fix 808 the excised tissue specimen 300 within the positioning apparatus 500, 500'. For instance, the surgeon may place the specimen 300 onto the elastically deformable portion 516 of the first positioning member 504 (e.g., such as generally over a central portion of the elastically deformable portion 516 as shown in FIGS. 16 and 22), align the first and second connection members 532, 536 of the second positioning member 508 with the second and first connection members 536, 532 of the first positioning member 504, elastically deform elastically deformable portions 516, 524 of the first and second positioning members 504, 508 about opposite portions of the specimen 300, and engage the respective pairs of first and second connection members 532, 536 to non-movably retain and fix 808 the excised tissue specimen within the specimen support volume of the positioning apparatus 500, 500' (see FIGS. 17-18 and 23-24).

Figure 18:
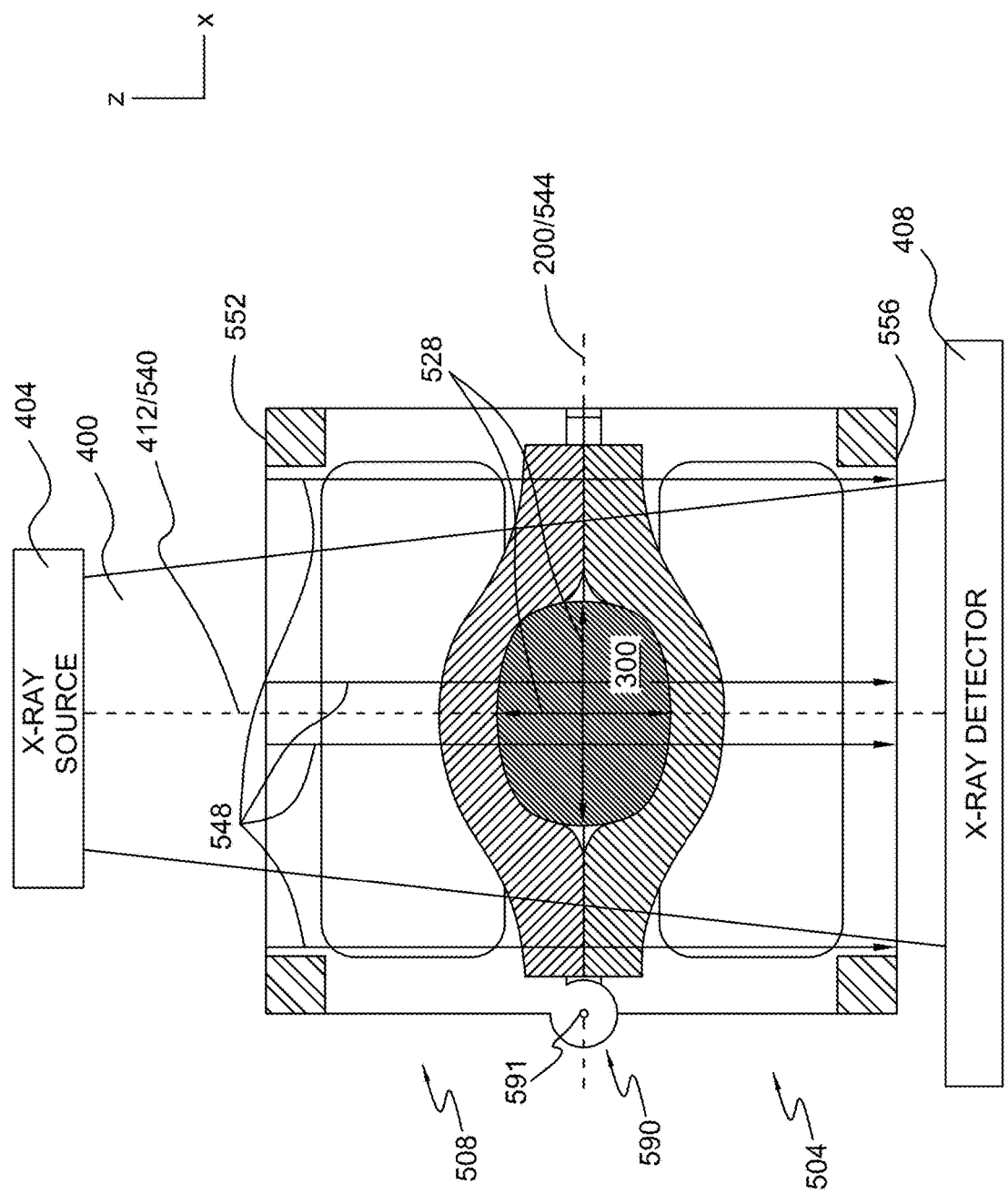
FIG. 18 is a sectional view through the apparatus and tissue specimen of FIG. 17 along the line 18-18 and illustrating an electromagnetic radiation signal being transmitted along a first axis through the apparatus and the tissue specimen to obtain a first image of the tissue specimen.
Figure 19:
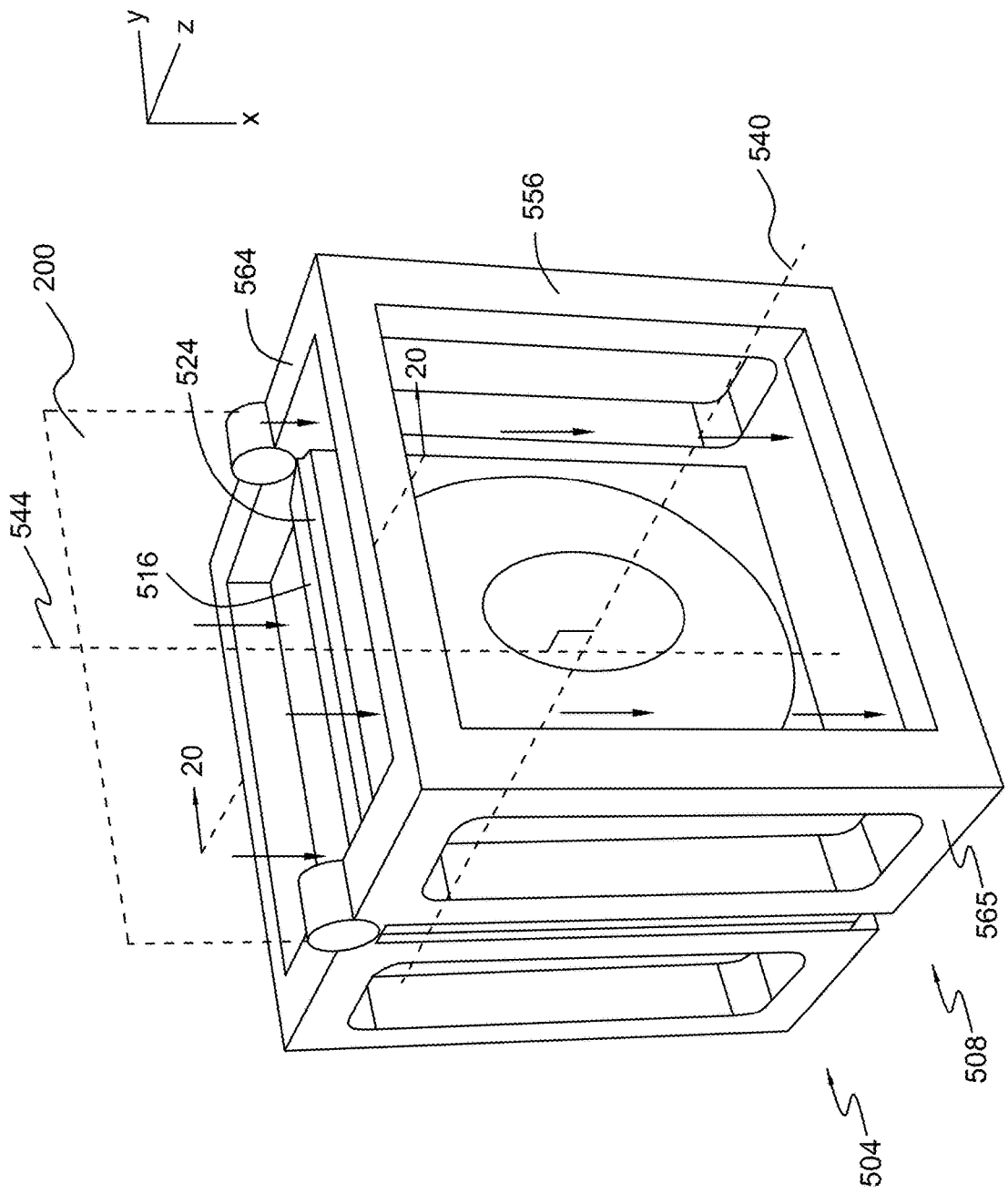
FIG. 19 is a perspective view similar to FIG. 17, but with the apparatus in a second orientation relative to the support surface that is 90° relative to the first orientation.
Figure 20:
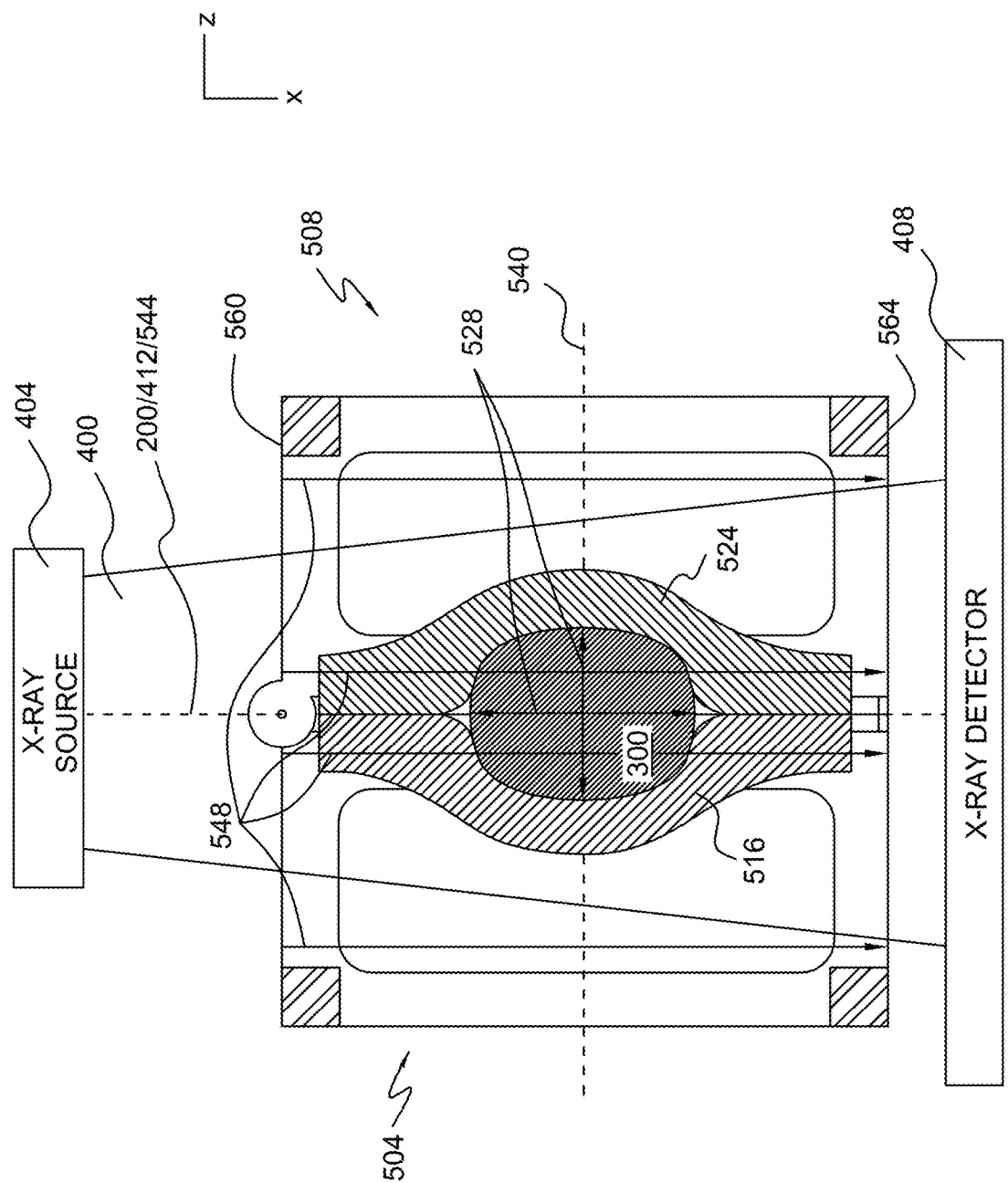
FIG. 20 is a sectional view through the apparatus and tissue specimen of FIG. 19 along the line 20-20 and illustrating an electromagnetic radiation signal being transmitted along a second axis through the apparatus and the tissue specimen to obtain a second image of the tissue specimen.
Figure 21:
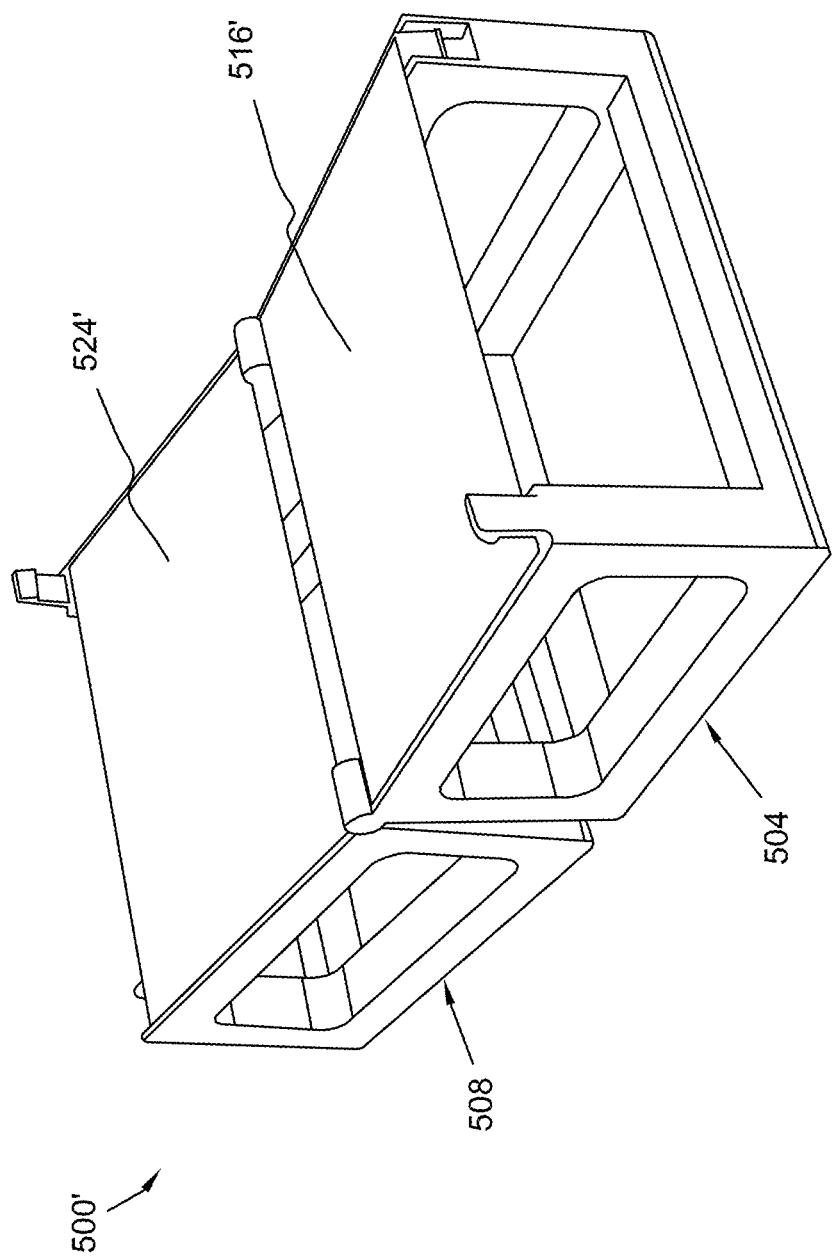
FIG. 21 is a perspective view of a specimen holding apparatus according to another embodiment, in an open orientation.
Figure 24:
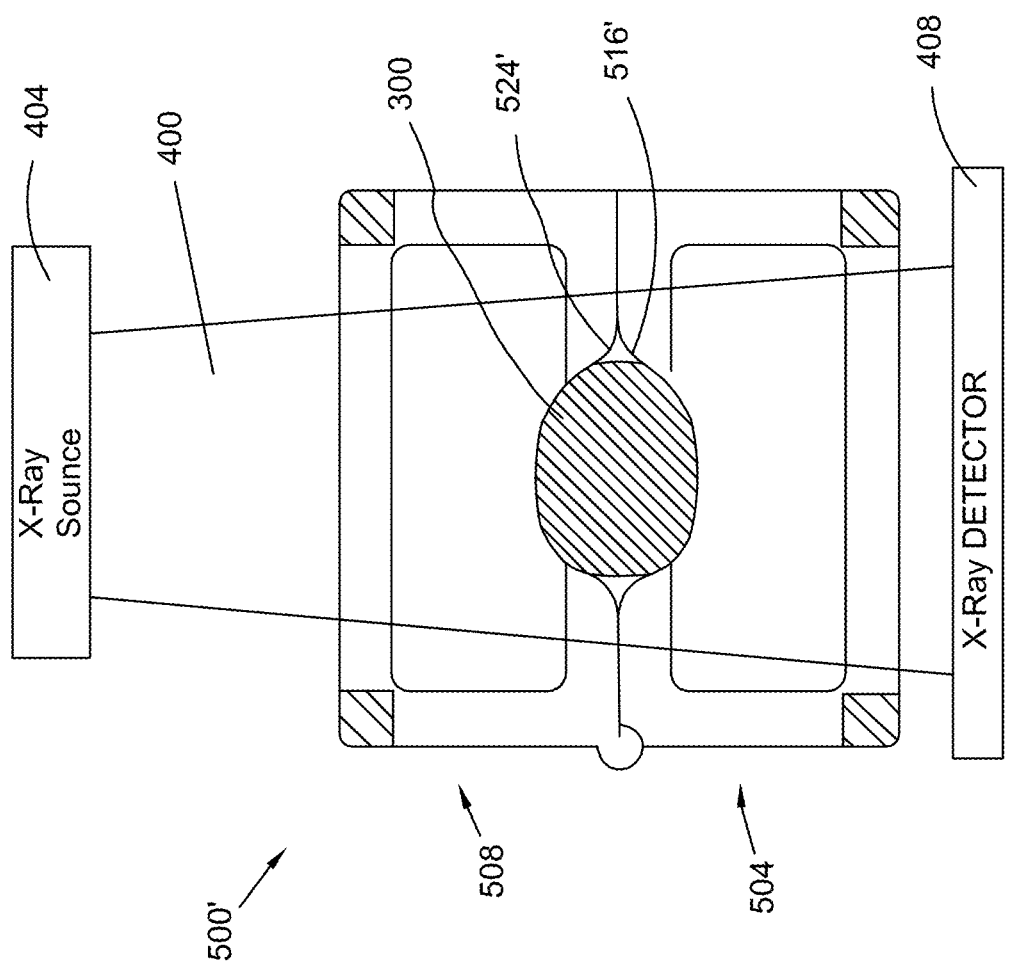
FIG. 24 is a sectional view through the apparatus and tissue specimen of FIG. 23 and illustrating an electromagnetic radiation signal being transmitted along a first axis through the apparatus and the tissue specimen to obtain a first image of the tissue specimen.
Figure 25:
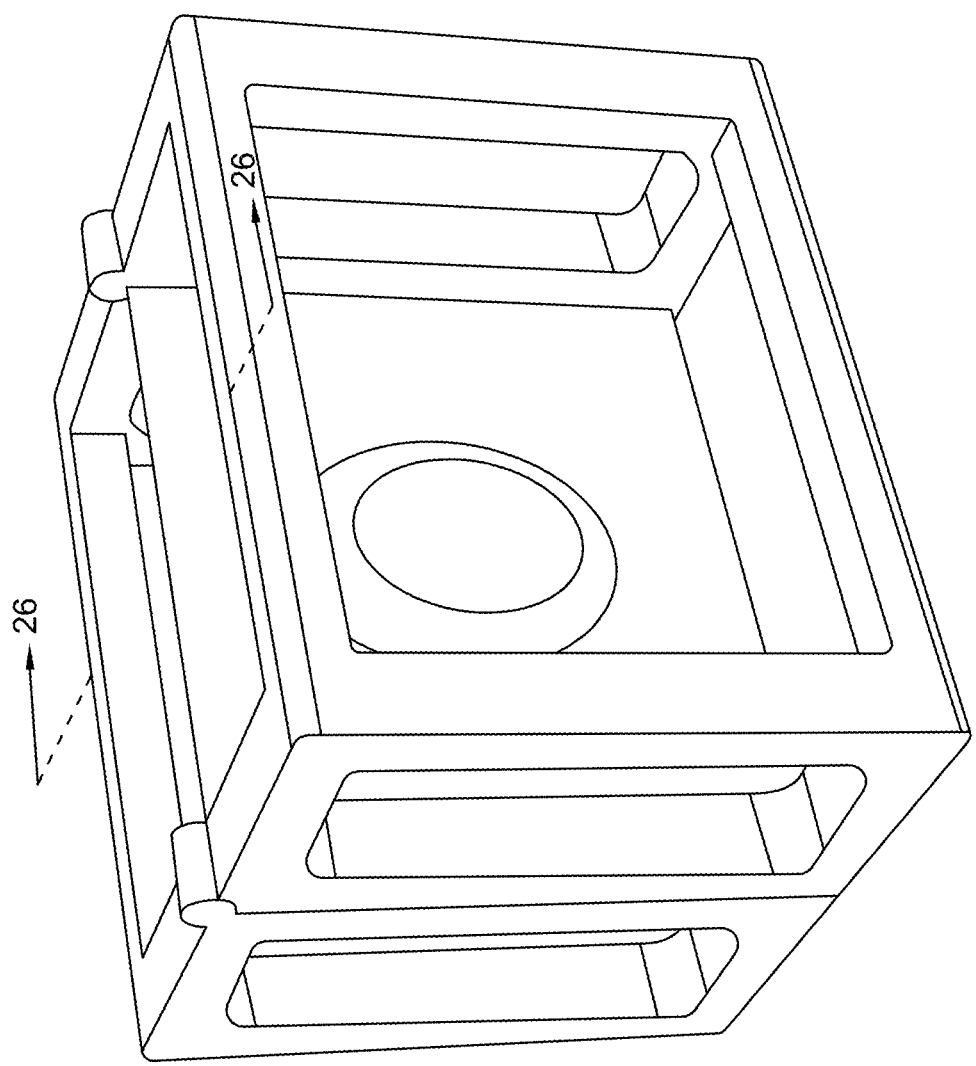
FIG. 25 is a perspective view similar to FIG. 23, but with the apparatus in a second orientation relative to the support surface that is 90° relative to the first orientation.
Figure 26:
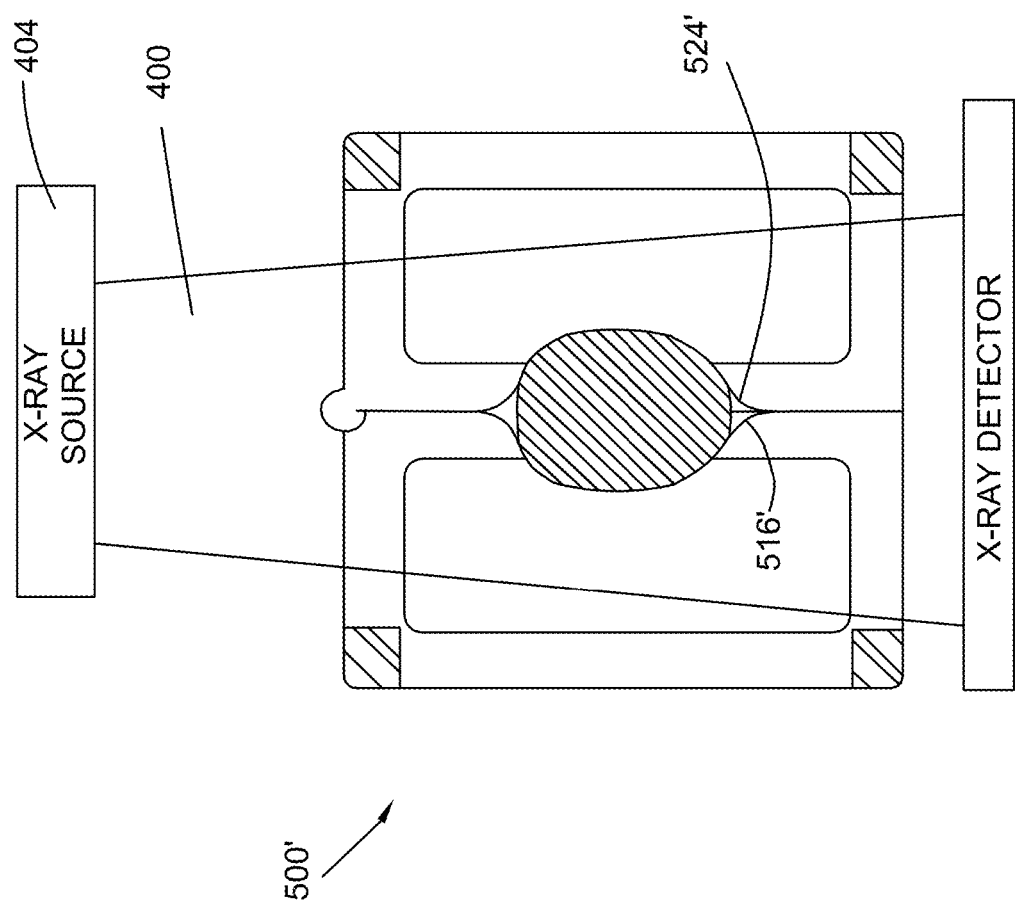
FIG. 26 is a sectional view through the apparatus and tissue specimen of FIG. 25 along the line 26-26 and illustrating an electromagnetic radiation signal being transmitted along a second axis through the apparatus and the tissue specimen to obtain a second image of the tissue specimen.

The method 800 may also include orienting 812 the positioning apparatus 500, 500' at a first orientation relative to a support surface (e.g., horizontal surface, not shown) and then imaging 816 the specimen 300 along the first axis 540 through the apparatus 500, 500' to obtain a first image of the specimen 300. With reference to FIGS. 18 and 24, the apparatus 500, 500' may be disposed along and/or about an imaging axis 412 of an imaging beam 400 between an x-ray (e.g., or other electromagnetic radiation) source 404 and an x-ray (e.g., or other electromagnetic radiation) detector 408 (e.g., sensor(s), film). For instance, the apparatus 500, 500' may be positioned so that the imaging axis 412 is coincident with and/or substantially parallel to the first axis 540 through the apparatus 500, 500', where the first axis 540 is substantially perpendicular to a reference plane 200 defined between the elastically deformable portions 516, 524 of the first and second positioning members 504, 508. See FIGS. 18 and 24. Stated differently, the apparatus 500, 500' may be positioned so that the imaging axis 412 is substantially perpendicular to the reference plane 200. In any event, the source 404 may generate and transmit an imaging signal 400 along imaging axis 412 and the first axis 540 through the apparatus 500, 500', specimen 300 and specimen support volume 528 for receipt at detector 408 to generate a first image of the specimen 300.

With reference to FIGS. 17-18 and 23-24, it is noted how the imaging signal 400 passes or propagates through a first volume 548 (represented by arrows) of the apparatus 500, 500' that extends from a first external side 552 of the apparatus 500, 500' to a second external side 556 of the apparatus 500, 500' that is opposite to the first external side 552. More specifically, the first volume 548 extends along the first axis 540 (e.g., in a z dimension) and about the first axis 540 (e.g., in the x and y dimensions) and encompasses the specimen support volume 528. Furthermore, the first volume 548 is free of any portion having a density (e.g., radiodensity) greater than either a density (e.g., radiodensity) of the elastically deformable portion 516 of first positioning member 504 or a density (e.g., radiodensity) of the elastically deformable portion 524 of the second positioning member 508.

In other words, an entire footprint of the imaging signal 400 is configured to pass through a volume (e.g., the first volume 548) of the apparatus 500, 500' that has a density no greater than the densities of the elastically deformable portions 516, 524 of the first or second positioning members 504, 508 that coincide with the first volume 548. As mentioned in other embodiments disclosed herein, markings or other features may be provided on the support surface (not shown) that may be used to automatically orient the apparatus 500, 500' so that an entirety or substantial entirety of the imaging signal 400 passes through the first volume 548.

In the embodiment of FIGS. 17-18 and 23-24, the first volume 548 extends from the first external side 552 to the opposite second external side 556 of the apparatus 500, 500' (e.g., in the z dimension) and up to (in the x and y dimensions) an inside surface (not labeled) of the frames of the first and second positioning members 504, 508 (e.g., up to the inside surfaces of the support ledges 513, 514; support members 568, 572; interconnection members 517; etc.). For instance, the first volume 548 may be devoid or free of anything (e.g., any components, objects, etc.) except for the elastically deformable portions (and air). In the situation where the bodies 512, 520 (e.g., frames) of the first and second positioning members 504, 508 are constructed of a material or materials having a radiodensity the same as or less than that of the elastically deformable portions 516, 524, the first volume 548 may extend through and towards an outer surface of the frames of the first and second positioning members 504, 508 and thus all the way to the third, fourth, fifth and sixth external sides 560, 564, 566 (sixth external side not labeled). As just one example, the first volume 548 may include at least 20% of a total volume occupied by the apparatus 500, 500', such as at least 40%, or at least 60%.

In any event, an entirety (or substantial entirety) of the specimen 300 may advantageously be imaged along and about the first axis 540 substantially free of signal attenuation that may otherwise produce artifacts in the resultant image, other reductions in quality of the resultant image, and/or the like. This arrangement is in contrast to prior or existing specimen holding/positioning apparatuses or systems whereby the imaging signal 400 would pass through relatively higher radiodensity materials disposed along the reference plane 200 and/or the imaging axis 412 during imaging of the specimen 300 (e.g., such as a plastic container within which the specimen is disposed; other objects, structures, supports, etc. within the path of the imaging signal 400, etc.) that can cause such undesired artifacts and image quality losses.

With brief reference back to FIG. 35, the method 800 may include reorienting 820 the positioning apparatus 500, 500' into a second orientation relative to the support surface (e.g., and the imaging axis 412) and then imaging 824 the specimen 300 along the second axis 544 through the apparatus 500, 500' to obtain a second image of the specimen 300. For instance, the entire apparatus 500, 500' may be pivoted or rotated by 90° (clockwise in this example about the y dimension) so that the third external side 560 of the apparatus 500, 500' rests on the support surface (e.g., which may in one embodiment include aligning the third external side 560 with any markings or the like on the support surface). Advantageously, the specimen 300 may remain substantially fixed or non-movable within the apparatus 500, 500' during the reorienting 820 (e.g., due at least in part to the first and second elastically deformable portions 516, 524) to increase the accuracy of subsequent imaging operations and analysis. In one arrangement, the specimen 300 may also be substantially non-deformably retained within the apparatus 500, 500' (e.g., retained in a manner substantially free of experiencing changes to its natural shape and dimensions) to further increase the accuracy of subsequent imaging operations and analysis.

In the second orientation, the imaging axis 412 may be coincident with and/or substantially parallel to the second axis 544, where the second axis 544 is coincident with and/or substantially parallel to the reference plane 200 defined between the elastically deformable portions 516, 524 of the first and second positioning members 504, 508. Stated differently, the apparatus 500, 500' may be positioned so that the imaging axis 412 is substantially coincident with or parallel to the reference plane 200. In any event, the source 404 may generate and transmit an imaging signal 400 along imaging axis 412, the second axis 540, and the reference plane 200 through the apparatus 500, 500' and specimen 300 for receipt at detector 408 to generate a second image of the specimen 300 that is orthogonal to the first image.

Similar to imaging of the specimen 300 along the first axis 540 through the apparatus 500, 500' and specimen 300, imaging of the specimen 300 along the second axis 544 through the apparatus 500, 500' and specimen 300 passes or propagates through a second volume 568 of the apparatus 500, 500' that extends from the third external side 560 of the apparatus 500, 500' to the fourth external side 564 (e.g. along the x dimension) of the apparatus 500, 500', where the second volume 568 is free of any portion having a density (e.g., radiodensity) greater than either a density (e.g., radiodensity) of the elastically deformable portion 516 of the first positioning member 504 or a density (e.g., radiodensity) of the elastically deformable portion 524 of the second positioning member 508. See FIGS. 19-20 and 25-26.

More specifically, the second volume 568 extends along and about the second axis 544 (e.g., in the x dimension) and encompasses the specimen support volume 528. That is, an entire footprint of the imaging signal 400 is configured to pass through a volume (e.g., the second volume 568) of the apparatus 500, 500' that has a density no greater than the densities of the elastically deformable portions 516, 524 of the first or second positioning members 504, 508 that coincide with the second volume 568. In other words, an entire footprint of the imaging signal 400 is configured to pass through a volume (e.g., the second volume 568) of the apparatus 500, 500' that has a density no greater than the densities of the elastically deformable portions 516, 524 of the first or second positioning members 504, 508 that coincide with the second volume 568. As mentioned in other embodiments disclosed herein, markings or other features may be provided on the support surface (not shown) that may be used to automatically orient the apparatus 500, 500' so that an entirety or substantial entirety of the imaging signal 400 passes through the second volume 568.

In the embodiment of FIGS. 19-20 and 25-26, the second volume 568 extends from the third external side 560 to the opposite fourth external side 564 of the apparatus 500, 500' (e.g., in the x dimension) and up to (in the z and y dimensions) an inside surface (not labeled) of the frames of the first and second positioning members 504, 508 (e.g., up to the inside surfaces of the support ledges 513, 514; support members 568, 572; interconnection members 517; etc.). For instance, the second volume 568 may be devoid or free of anything (e.g., any components, objects, etc.) except for the elastically deformable portions (and air). In the situation where the bodies 512, 520 (e.g., frames) of the first and second positioning members 504, 508 are constructed of a material or materials having a radiodensity the same as or less than that of the elastically deformable portions 516, 524, the second volume 568 may extend through and towards an outer surface of the frames of the first and second positioning members 504, 508 and thus all the way to the first, second, fifth and sixth external sides 552, 556, 566 (sixth external side not labeled). As just one example, the second volume 568 may include at least 20% of a total volume occupied by the apparatus 500, 500', such as at least 40%, or at least 60%.

The specimen 300 may thus be imaged along the reference plane 200 (e.g., where the imaging axis 412 is substantially coincident with or parallel to the second axis 544 and reference plane 200) substantially free of signal attenuation caused by components/supports/etc. having a radiodensity greater than that of the elastically deformable portions 516, 524 of the first and second positioning members 504, 508 that may otherwise be present along the imaging axis 412. The apparatus 500, 500' advantageously allows a surgeon, other personnel, and/or the like to rapidly and easily place an excised specimen 300 onto a horizontally disposed surface (e.g., elastically deformable portion 516 of FIGS. 16 and 22), retain and image the specimen 300 within the apparatus 500, 500' along one axis (e.g., the first axis 140) to obtain a first image of the specimen 300 (see FIGS. 17-18 and 23-24), rotate the entire apparatus 100 by 90° (see FIGS. 19-20 and 25-26), and then image the specimen 300 within the apparatus 500, 500' along an orthogonal axis (e.g., the second axis 544) to obtain a second image of the specimen 300.

If appropriate tissue margins have not been detected in the specimen 300 at step 828 of the method 800 in FIG. 35, the method 800 may flow back to 804 to excise another tissue specimen, retain and fix 808 the specimen within a positioning apparatus (e.g., apparatus 500), and the like. While the method 800 has been discussed in the context of first imaging along the first axis 140 and then imaging along the second axis 144, it is also envisioned that the specimen 300 could first be imaged along the second axis 144 and then imaged along the first axis 140. If appropriate tissue margins have been identified at 828, the method 800 may include horizontally (e.g., so that the reference plane 200 is substantially parallel to a support surface) imaging 836 the specimen 300 through any appropriate grid member (grid member 182 of FIG. 12) including any appropriate radiopaque lines, indicia, or the like so that the grid lines/indicia appear in the resulting image. The surgeon may then appropriately indicate 840 the areas of interest on the tissue specimen using the grid lines to inform the pathologist the location(s) of the most suspicious areas in the resulting image (e.g., by providing coordinates, marking directly on the image, etc.). The resulting image and excised tissue specimen may then be sent 844 to the pathologist for performing a diagnostic procedure and providing a diagnostic opinion.

Turning now to FIGS. 27-34, another embodiment of the apparatus 100 is disclosed and identified by the reference numeral 700 in the interest of clarity (e.g., rather than 100'''' or the like) and similar reference numerals (e.g., 104 in FIGS. 3 and 704 in FIG. 28 to indicate a first positioning member) have been used to the extent possible. Also shown in the figures is an imaging system 600 for imaging a specimen retained in the apparatus 700. While the system 600 will primarily be discussed in the context of a specimen 300 retained within the apparatus 700 (e.g., via interconnecting the apparatus 700 with connection members on opposite sidewalls of a chamber of the system 600 as discussed below), the system 600 may also be used with the other apparatuses disclosed herein (e.g., via placing the apparatus directly over an imaging detector of the system 600).

Figure 27:
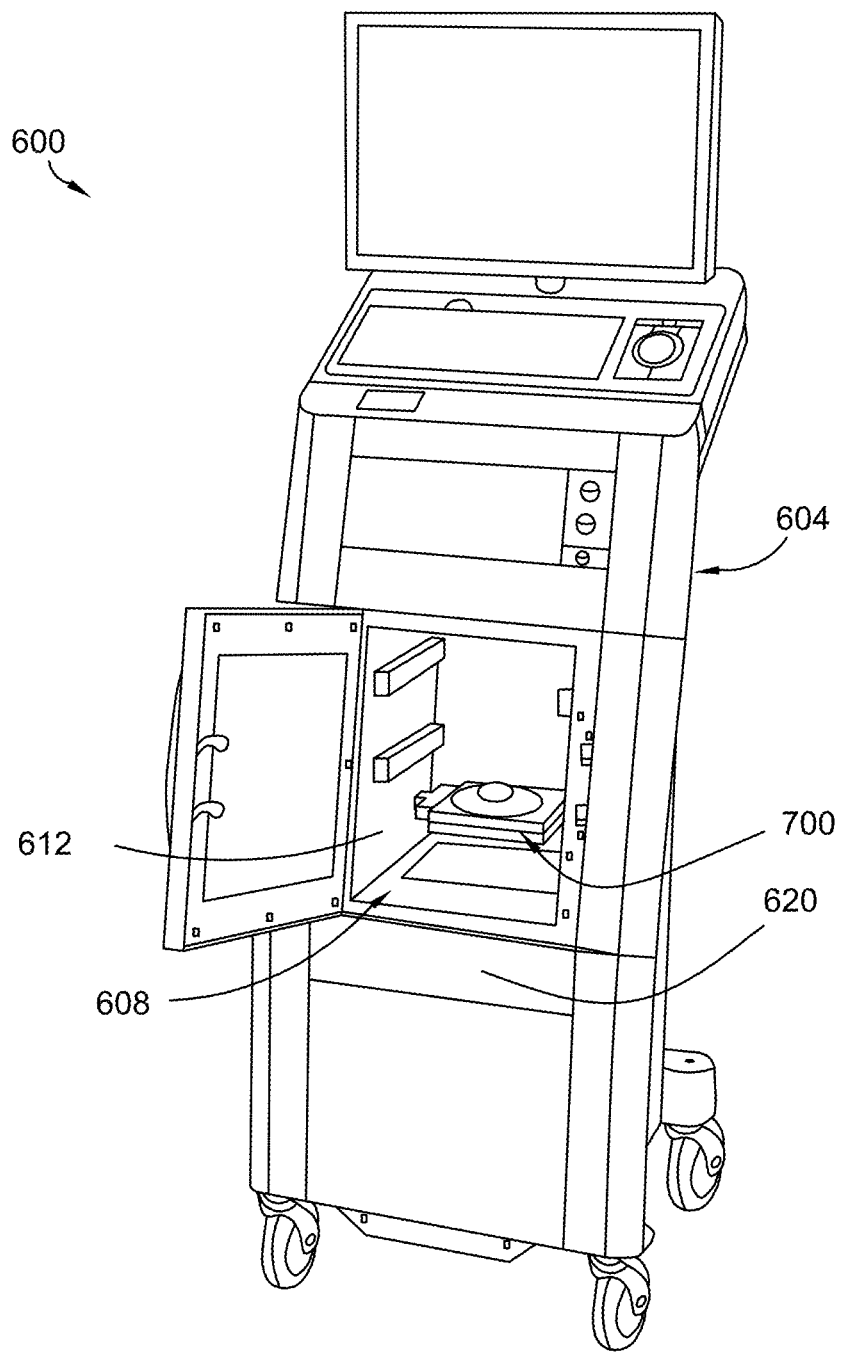
FIG. 27 is a perspective view of a specimen imaging apparatus including a specimen holding apparatus according to another embodiment being positioned within an imaging chamber of the specimen imaging apparatus.

As shown in FIG. 27, the system 600 may broadly include a housing 604; a chamber 608 within the housing 604, wherein the chamber 608 is defined by at least first and second spaced or opposite sidewalls 612, 616 or support surfaces, a source (not labeled) of electromagnetic radiation disposed adjacent one end of the chamber 608 (e.g., adjacent a top of the chamber 608); and an imaging detector 620 disposed adjacent an opposite end of the chamber 608 (e.g., adjacent a bottom of the chamber 608); where the source is configured to emit an electromagnetic radiation signal 624 along an imaging axis 628 through the chamber 608 towards the imaging detector 620. Numerous other details of the system 600 (e.g., monitor, controls, etc.) have been omitted from this discussion in the interest of clarity.

Figure 28:
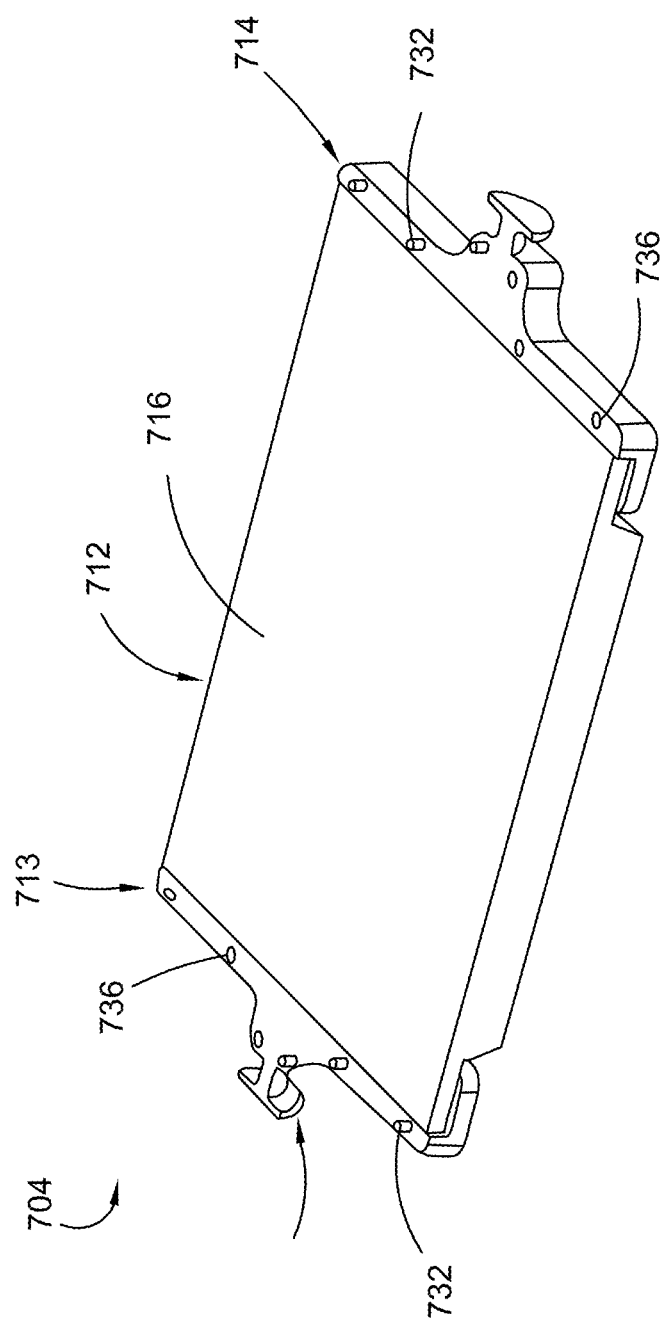
FIG. 28 is a perspective view of a first positioning member of the specimen holding apparatus of FIG. 27.
Figure 29:
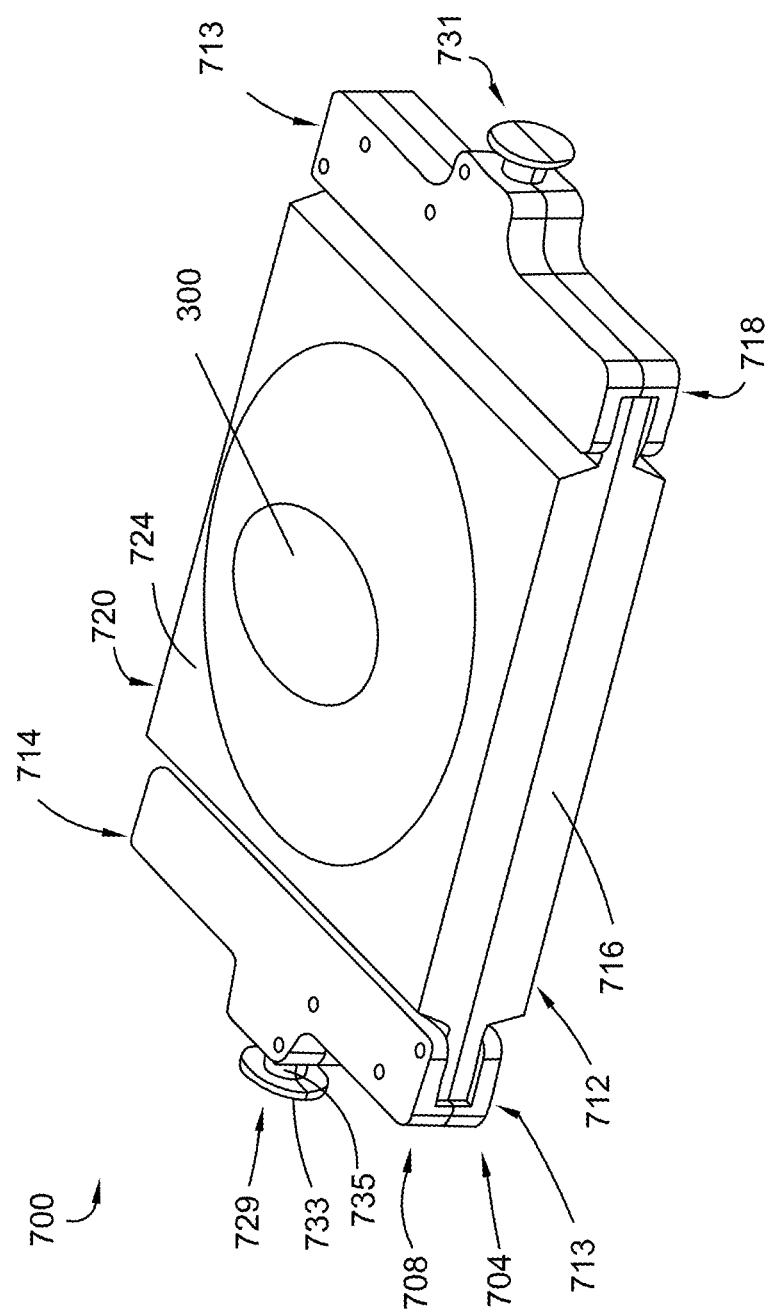
FIG. 29 is a perspective view of the specimen holding apparatus of FIG. 27.

With brief reference now to FIGS. 28-29, the apparatus 700 includes a first or lower positioning member 704 having a body 712 and an at least partially elastically deformable portion 716 (e.g., a "retention" portion or member), and a second or upper positioning member 708 having a body 720 and an at least partially elastically deformable portion 724 (e.g., a "retention" portion or member). Upon placement of at least one specimen 300 over the elastically deformable portion 716 of the first positioning member 704 and then non-movable or fixed securement of the second positioning member 708 to the first positioning member 704, the elastically deformable portions 716, 724 of the first and second positioning members are respectively configured to elastically deform about opposite portions of the specimen 300 to thereby retain the specimen 300 therebetween within a specimen support volume 728 of the apparatus 700 (see FIG. 18) for use in accurate imaging of the specimen, transport of the specimen and the like.

As shown, the body 712 of the first positioning member 704 may include first and second spaced opposite support members or ledges 713, 714 over which opposite ends of the elastically deformable portion 716 are configured to be appropriately secured (e.g., via adhesives, bonding, or the like). Similarly, the body 720 of the second positioning member 708 includes first and second spaced opposite support ledges 713, 714 over which opposite ends of the elastically deformable portion 724 are configured to be appropriately secured (e.g., via adhesives, bonding, or the like). The support members/ledges 713, 714 may extend laterally away from the opposite ends of the elastically deformable members 716, 724. Furthermore, the apparatus 700 includes one or more features that allow for fixable positioning of the first and second positioning members 704, 708 to allow for substantial non-movable retaining of the specimen 300 between the elastically deformable portions 716, 724 as well as suspension of the specimen 300 within the apparatus 700.

For instance, the first and second positioning members 704, 708 may each include at least one respective connection member such as first and second connection members 732, 736 that are respectively configured to engage with the second and first connection members 736, 732 of the other of the first and second positioning members 704, 708. Like in the other embodiments disclosed herein, each first connection member 732 of one of the first and second positioning members 704, 708 may be complimentary and removably connectable to a respective second connection member 736 of the other of the first and second positioning members 704, 708 to fixedly position the first and second positioning members 704, 708 relative to each other. In one embodiment, each of the first and second positioning members 704, 708 (e.g., the first and second support members or ledges 713, 714) may include at least one first connection member 732 and at least one second connection member 736 adjacent respective first and second external sides of the apparatus 700. For instance, each first connection member 732 may be in the form of a protrusion (e.g., tab, post, detent, etc.) and each second connection member 736 may be in the form of a complimentary-shaped and sized recess (e.g., opening, hole, detent, etc.). In one embodiment, the first connection members 732 may be press-fit into the second connection member 736. Various other forms of first and second connection members 732, 736 are envisioned and encompassed herein.

As discussed in relation to other embodiments disclosed herein, each of the elastically deformable portions 716, 724 of the first and second positioning members 704, 708 is configured to at least partially transmit an imaging signal (e.g., electromagnetic radiation signal, such as an x-ray) therethrough to allow for imaging of the specimen 300 along first and second orthogonal axes 740, 744 through the apparatus 700 (e.g., including through the specimen support volume 728) to obtain respective first and second images of the specimen (e.g., for use in specimen margin verification and the like). Additionally, each of the elastically deformable portions 716, 724 is configured to at least partially elastically deform about an opposite portion of a specimen 300 to retain the specimen within the apparatus 700 when the first and second positioning members 704, 708 are non-movable secured to each other (e.g., see FIG. 18).

In one arrangement, each of the elastically deformable portions 716, 724 may be constructed of a sheet, layer, etc. of any appropriate radiolucent solid (e.g., polymeric) foam(s) (e.g., as discussed previously in relation to the apparatuses 100, 500). See apparatus 700 of FIGS. 28-31. In another arrangement, each of the elastically deformable portions 716, 724 may be constructed of a sheet, layer, etc. of any appropriate radiolucent film (e.g., polyurethane, etc.). See apparatus 700' of FIGS. 32-34. For instance, the film could be bonded onto the support ledges 713, 714 during production or the frames of the first and second positioning members 704',708' could be reusable and the film added by the customer and disposed of after each single use. As another example, some arrangement envision including a pre-applied adhesive along the front and back edges of the film to limit sliding/movement of the specimen 300 when the apparatus 700, 700' is reoriented (e.g., rotated). In some arrangements, one or both of the elastically deformable portions 716, 724 may include combinations of film and foam (e.g., parallel layers of a film and a solid foam).

Like with the other embodiments disclosed herein, the material properties (e.g., compression resistance, modulus of elasticity, etc.) and/or dimensions (e.g., thickness) of the elastically deformable portions 716, 724 of the first and second positioning members 704, 708 may be selected to retain the specimen 300 within the specimen support volume 728 of the apparatus 700 against movement relative to the apparatus 700 (e.g., relative to the frames of the first and second positioning members 704, 708). In one arrangement, the material properties and/or dimensions of the elastically deformable portions 716, 724 may be selected or configured to substantially inhibit deformation of the specimen 300 from its natural shape and dimensions while still retaining the specimen 300 against movement relative to the apparatus 700.

As disclosed herein, orthogonal imaging of a specimen 300 to obtain first and second orthogonal images may be important in relation to analyzing and confirming tissue margins as part of a diagnosis of the specimen 300. In this regard, and after a specimen 300 has been placed between the elastically deformable portions 716, 724 and the first and second positioning members 704, 708 have been fixably positioned (e.g., via aligning and interconnecting the pairs of first and second connection members 732, 736) so as to elastically deform the elastically deformable portions 716, 724 about opposite portions of the specimen 300 (e.g., as in FIG. 29), the apparatus 700 may be placed into chamber 608 so that a first axis 740 disposed through the specimen support volume 728 (and that is substantially perpendicular to a reference plane 200 disposed between the elastically deformable portions 716, 724) is substantially coincident with or parallel to the imaging axis 628. See FIG. 30. In one arrangement, a second of first and second external sides 752, 756 of the apparatus 700 may be placed directly on the imaging detector 620.

In another arrangement, opposite ends of the apparatus 700 may be respectively interconnected (e.g., removably interconnected) to the first and second sidewalls 612, 616 of the chamber 608 to at least partially space the apparatus 700 from the image source and detector and thereby facilitate orthogonal reorientation of the apparatus 700. As an example, the apparatus 700 may include opposite first and second connection components 729, 731 that are respectively configured to engage with complimentary first and second connection components 629, 631 on the first and second sidewalls 612, 616 of the chamber 608. For instance, the first and second connection components 729, 731 may be in the form of fasteners having a shaft 733 (e.g., that defines a pivot axis 734 of the apparatus 700 as discussed below) and a head 735 attached to the shaft 733. In one embodiment, each of the first and second positioning members 704, 708 may include a portion (e.g., a half) of each of the first and second connection components 729, 731 (e.g., see FIGS. 28-29), whereby a complete or full first and second connection component 729, 731 is automatically formed upon interconnection of the first and second positioning members 704, 708 (e.g., via interconnection of the respective pairs of first and second connection members 732, 736).

In any case, the first and second connection components 629, 631 may, in one embodiment, be in the form of openings, recesses or hubs that are configured to respectively receive the first and second connection components 729, 731. For instance, each of the first and second connection components 629, 631 may include a slot 633 for slidable and rotatable receipt of the shaft 733 and a channel 735 for slideable and rotatable receipt of the head 735. In this regard, the first and second connection components 729, 731 may be respectively engaged with (e.g., inserted or clipped into) the first and second connection components 629, 631 on the first and second sidewalls 612, 616 of the chamber 608 so that the first axis 740 disposed through the specimen support volume 728 (and that is substantially perpendicular to a reference plane 200 disposed between the elastically deformable portions 716, 724) is substantially coincident with or parallel to the imaging axis 628. See FIG. 30. The source may generate and transmit an imaging signal 624 along imaging axis 628 and the first axis 740 through the apparatus 700, specimen 300 and specimen support volume 728 for receipt at detector 620 to generate a first image of the specimen 300.

While not discussed in more detail, the apparatus 700 may include, like other apparatuses and embodiments disclosed herein, a first volume extending from a first external side 752 of the apparatus 700 to an opposite second external side 756 of the apparatus 700 that is free of any portion having a density (e.g., radiodensity) greater than either a density (e.g., radiodensity) of the elastically deformable portion 716 of the first positioning member 704 or a density (e.g., radiodensity) of the elastically deformable portion 724 of the second positioning member 708. For instance, the chamber 608 may be devoid of any structure or components between the source and detector 620 other than the elastically deformable portions 716, 724. The first volume extends along and about the first axis 740 and encompasses the specimen support volume 728. For instance, the first volume may extend up to inner surfaces of the first and second support ledges 713, 714.

Figure 30:
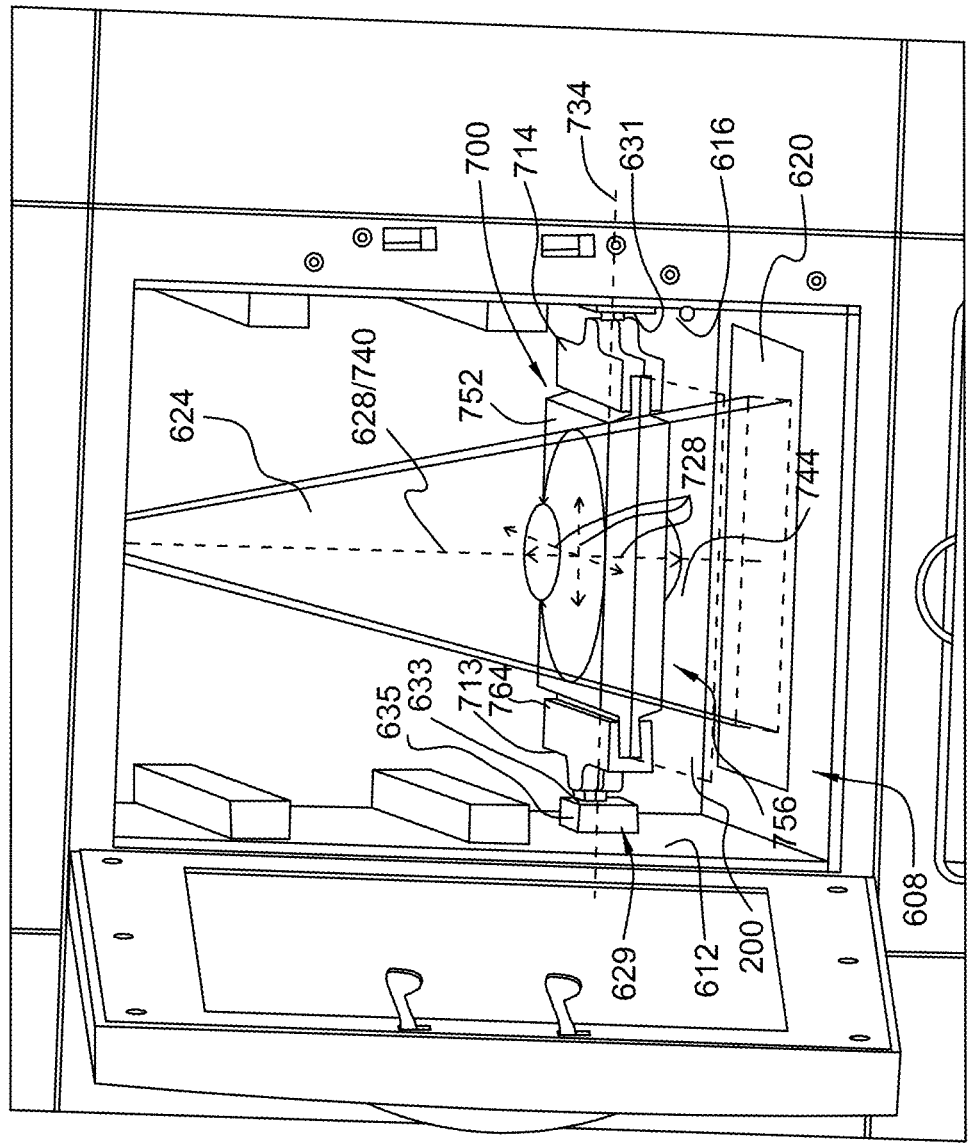
FIG. 30 is a close-up perspective view of FIG. 27 and illustrating the specimen holding apparatus being positioned in a first orientation within the imaging chamber.
Figure 31:
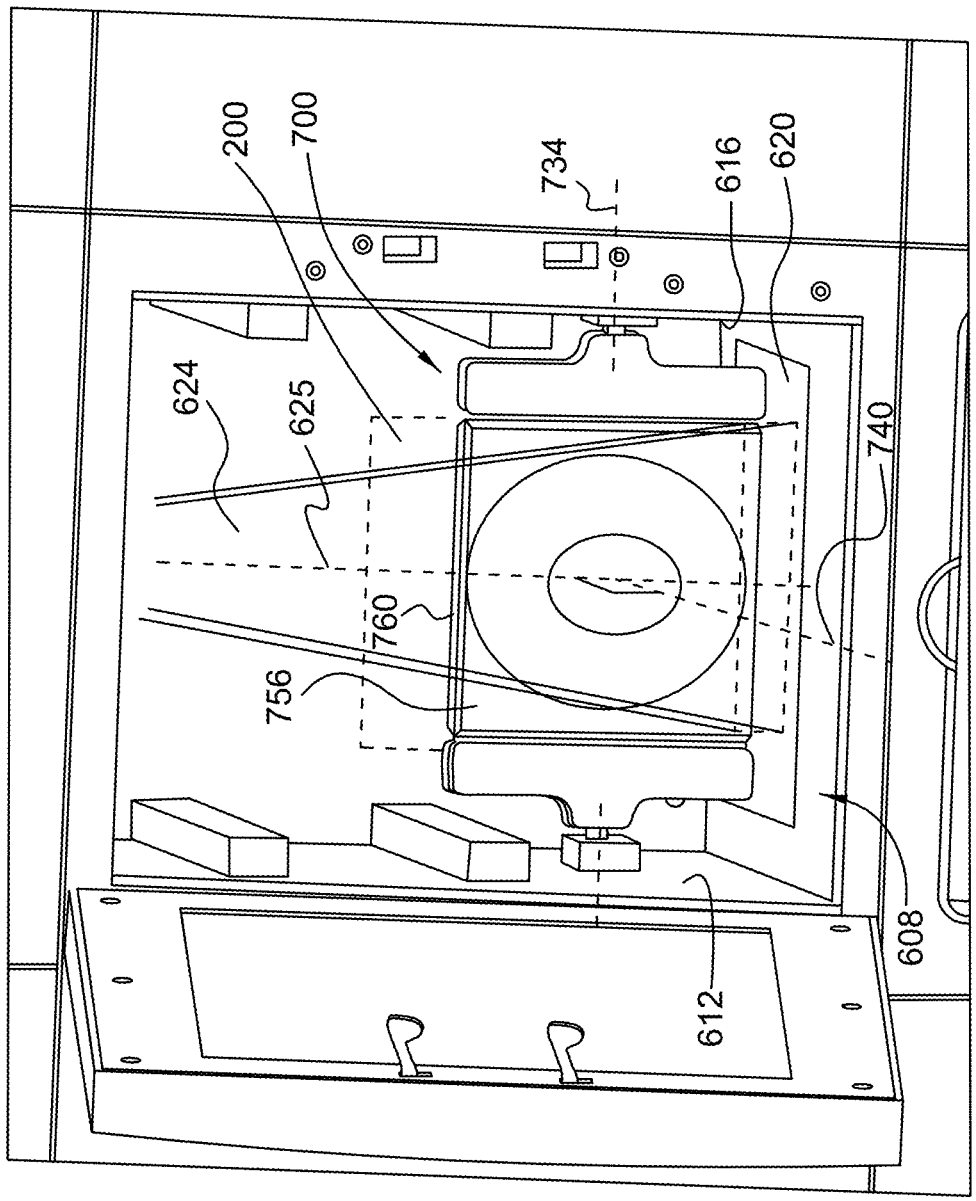
FIG. 31 is a close-up perspective view of FIG. 30 and illustrating the specimen holding apparatus being positioned in a second orientation within the imaging chamber that is 90° relative to the first orientation.
Figure 32:
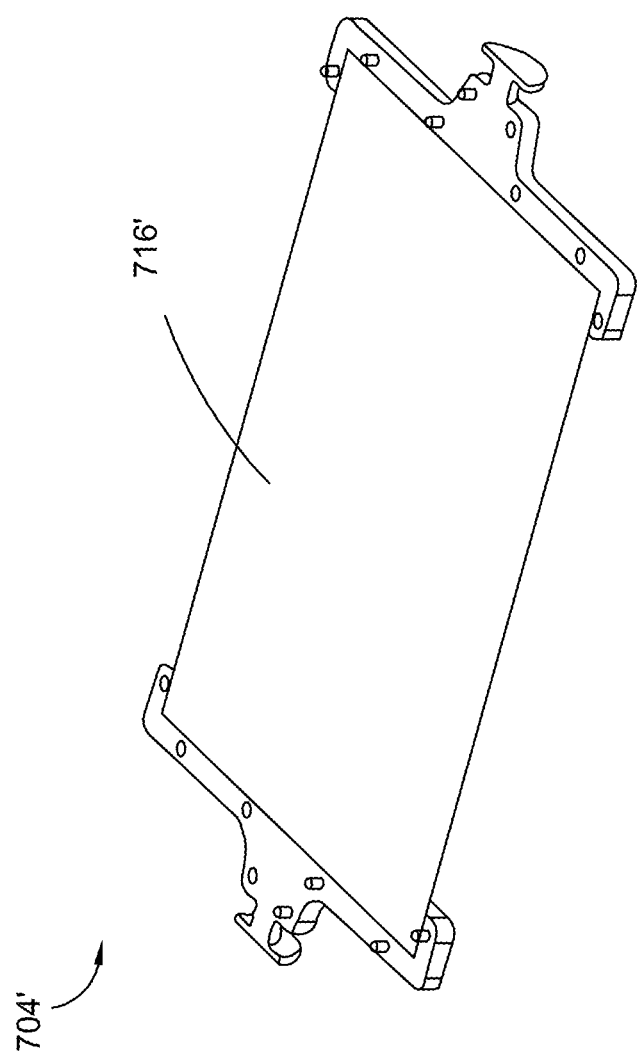
FIG. 32 is a perspective view of a lower positioning member of a specimen holding apparatus according to another embodiment.
Figure 33:
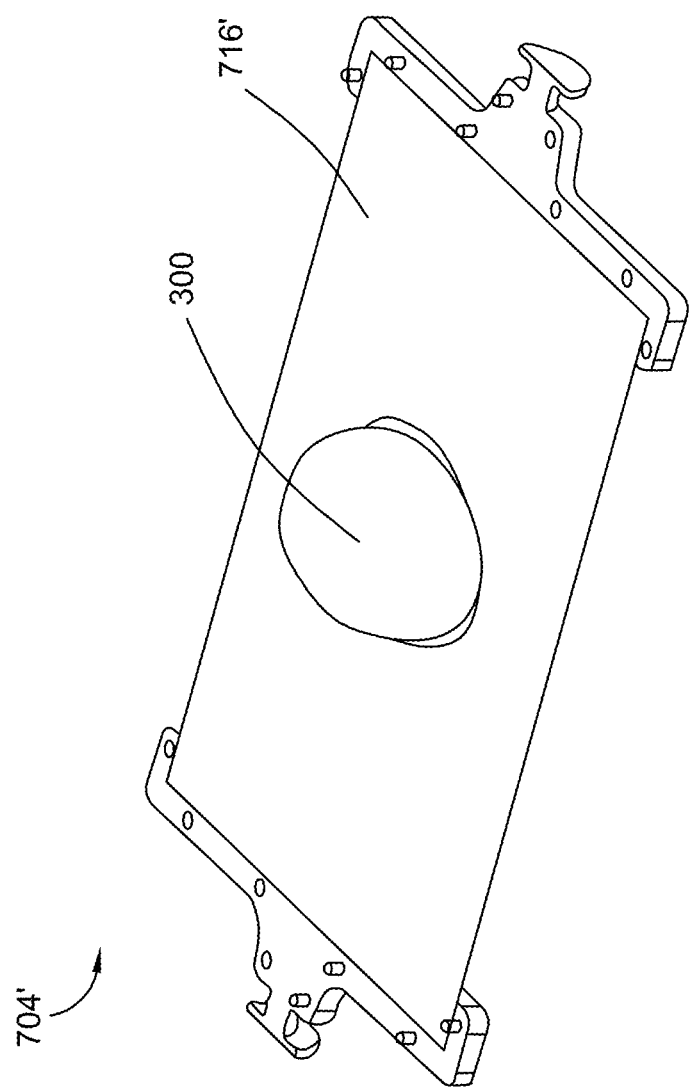
FIG. 33 is a perspective view similar to FIG. 32 but with a tissue specimen disposed over an at least partially elastically deformable portion of the lower positioning member.
Figure 34:
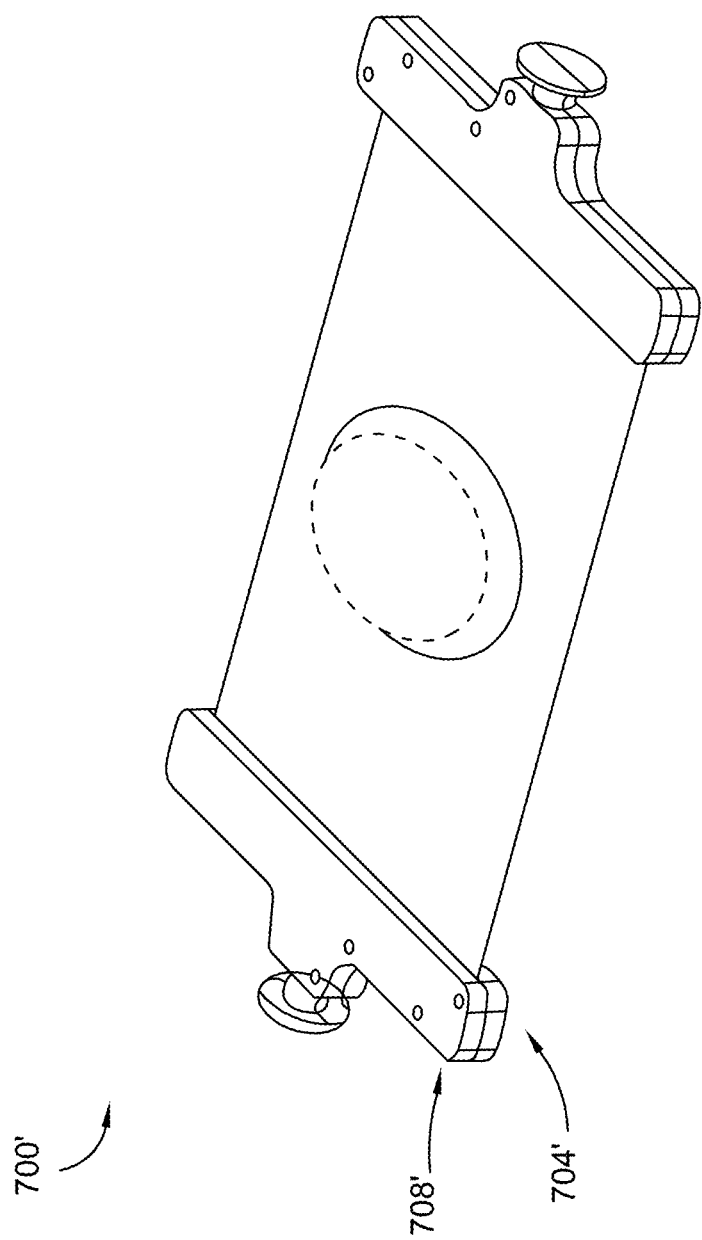
FIG. 34 is a perspective view similar to FIG. 33 but showing an upper positioning member being fixably retained relative to the lower positioning member so that at least partially elastically deformable portions of the upper and lower positioning members retain the tissue specimen therebetween.

After the first image has been obtained in the position of FIG. 30, the apparatus may be reoriented so as to align the second axis 744 and the reference plane 200 with the imaging axis 628 (e.g., so that the imaging axis 628 is substantially coincident with or parallel to the second axis 744 and the reference plane 200). For instance, the apparatus 700 may be rotated about rotation axis 734 by 90° (e.g., where the rotation axis 734 is substantially perpendicular to the imaging axis 628). See FIG. 31. The specimen may then be imaged to obtain a second image of the specimen and the first and second images analyzed to verify tissue margins. While also not discussed in more detail, the apparatus 700 may include, like other apparatuses and embodiments disclosed herein, a second volume extending from a third external side 760 of the apparatus 700 to an opposite fourth external side 764 (labeled in FIG. 30) of the apparatus 700 that is free of any portion having a density (e.g., radiodensity) greater than either a density (e.g., radiodensity) of the elastically deformable portion 716 of the first positioning member 704 or a density (e.g., radiodensity) of the elastically deformable portion 724 of the second positioning member 708. The second volume extends along and about the second axis 744 and encompasses the specimen support volume 728. For instance, the second volume may extend up to inner surfaces of the first and second support ledges 713, 714. In one arrangement, the first image may be obtained along the second axis 744 and the second image obtained along the first axis 740.

Figure 36:
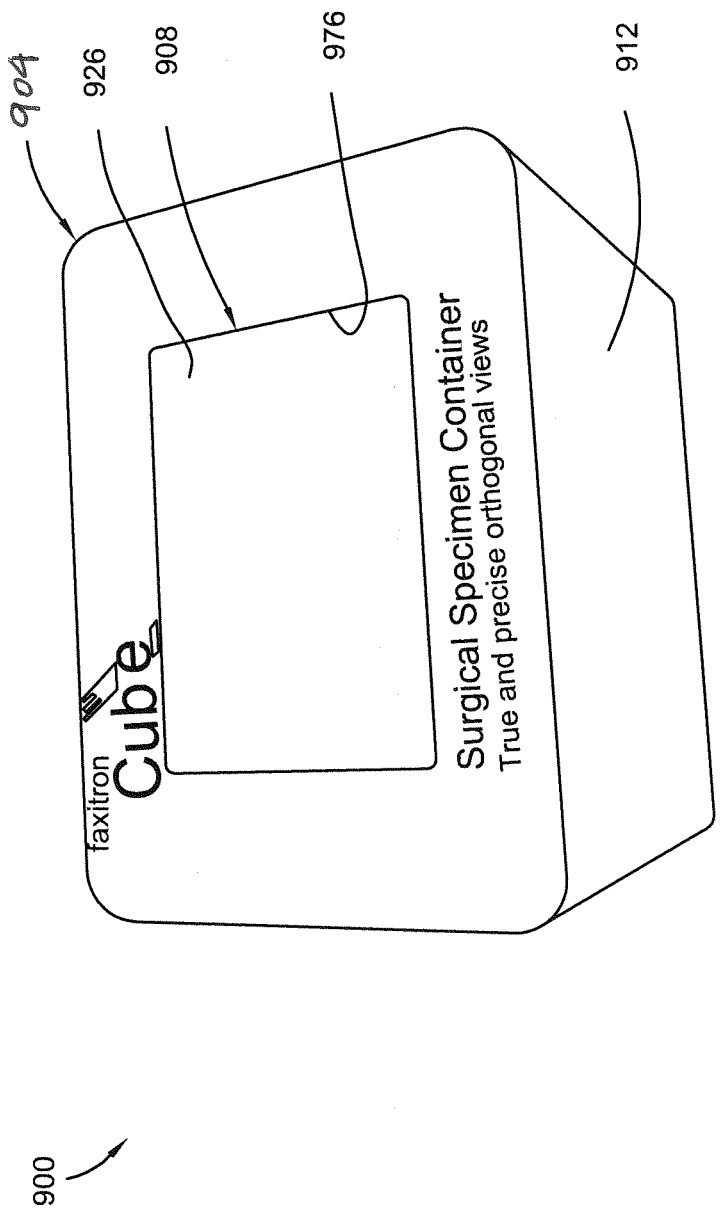
FIG. 36 is a perspective view of a specimen holding apparatus according to another embodiment.

Turning now to FIG. 36, another embodiment of the apparatus 100 is disclosed and identified by the reference numeral 900 in the interest of clarity (e.g., rather than 100"'") or the like) and similar reference numerals (e.g., 104 in FIGS. 3 and 804 in FIG. 36 to indicate a first positioning member) have been used to the extent possible. Broadly, the apparatus 900 includes a first or lower positioning member 904 having a body 912 and an at least partially elastically deformable portion 916 (e.g., a "retention" portion or member), and a second or upper positioning member 908 having a body 920 and an at least partially elastically deformable portion 924 (e.g., a "retention" portion or member).

Figure 37:
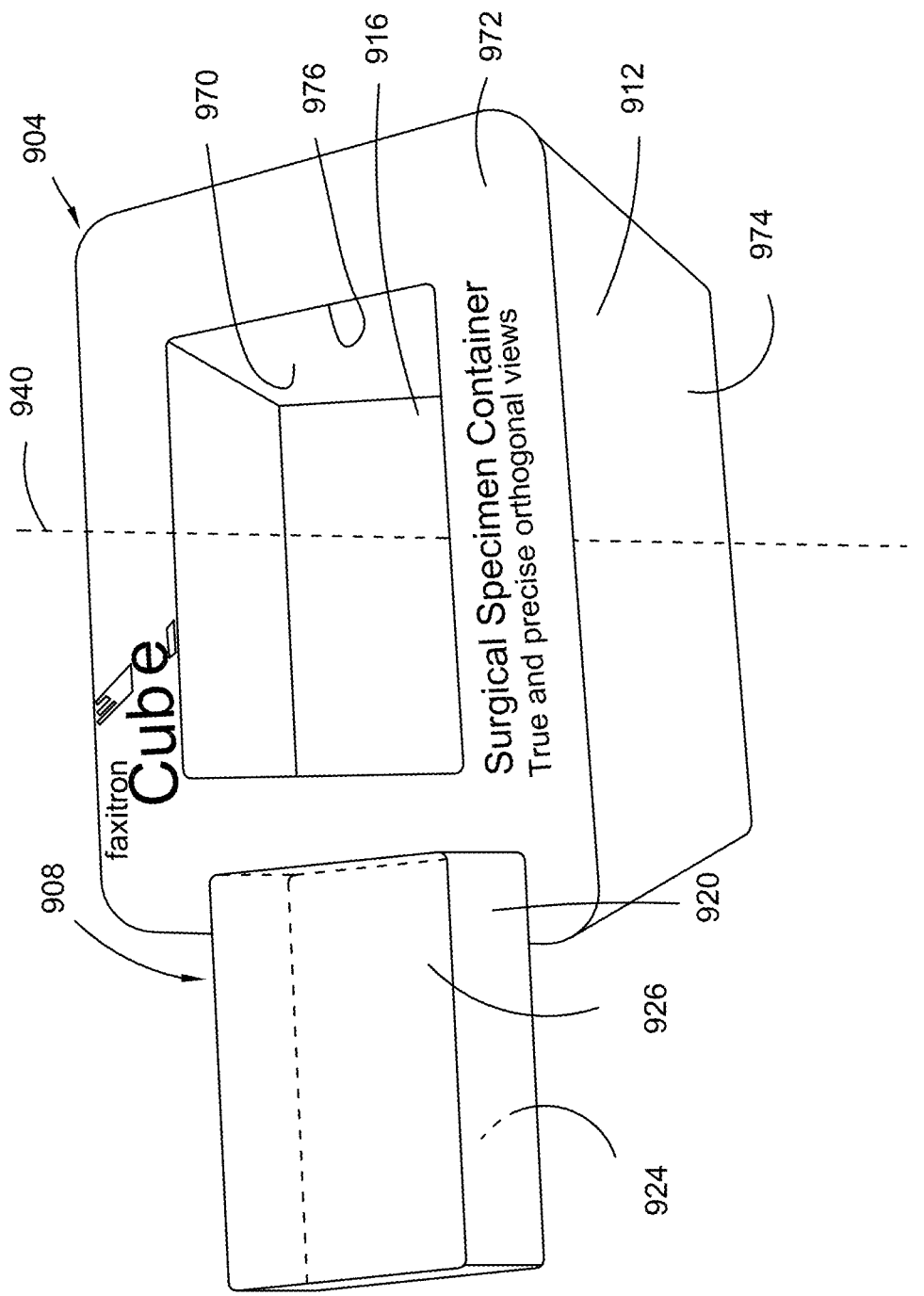
FIG. 37 is an exploded perspective view of the specimen holding apparatus of FIG. 36.
Figure 38:
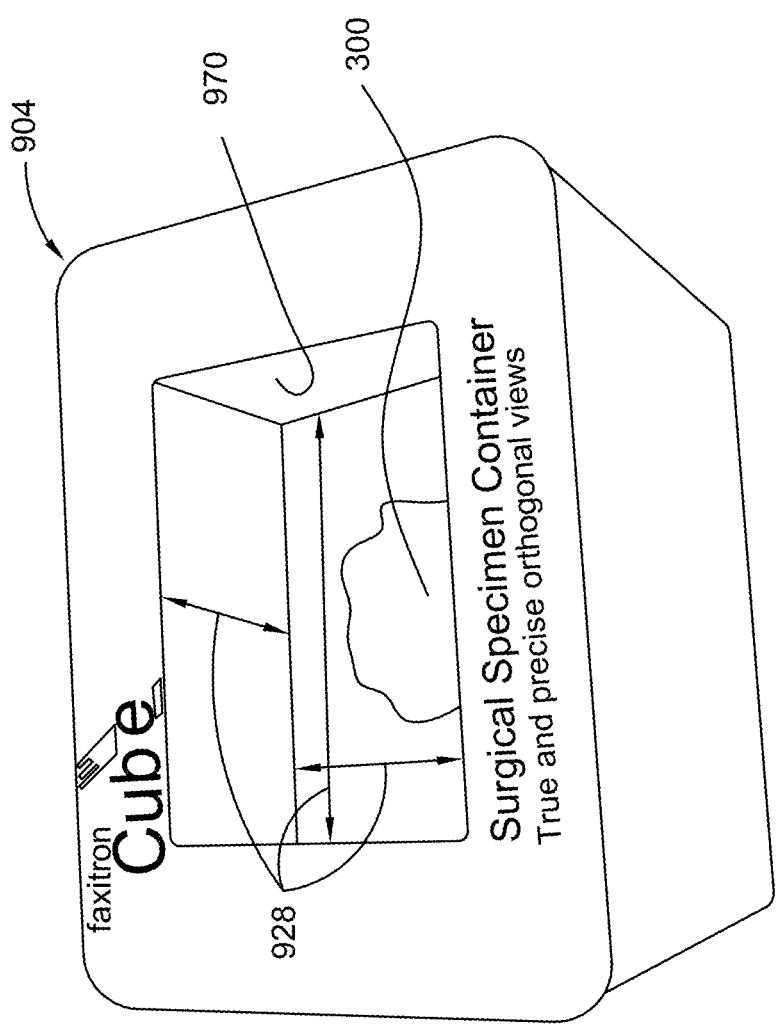
FIG. 38 is a perspective view of the specimen holding apparatus of FIG. 36 with a specimen received in an opening of a first positioning member of the apparatus.

As shown in FIG. 37, the first positioning member 904 includes an opening 970 (e.g., depression) extending partially through the body 912 from an upper portion 972 towards an opposite lower portion 974 of the body 912, where the elastically deformable portion 916 of the first positioning member 904 is a lower surface or wall of the opening 970 and the elastically deformable portion 924 of the second positioning member 908 is a bottom or lower wall of the body 920 of the second positioning member 908. The opening 970 includes a specimen support volume 928 that is configured to receive a tissue specimen 300 disposed (e.g., placed) onto the elastically deformable portion 916. See FIG. 38.

The first and second positioning members 904, 908 are configured to be fixably positioned relative to each other to non-movably retain the specimen 300 between the first and second elastically deformable portions 916, 924 within the specimen support volume 928 of the apparatus 900. In this regard, the apparatus 900 may be in the form of a container that is configured to secure the specimen 300 within the specimen support volume 928 of the apparatus 900. In one arrangement, the second positioning member 908 may be configured to be press fit (e.g., friction fit, pushed) at least partially into the opening 970 towards the elastically deformable portion 916 of the first positioning member 904 to fixably position the first and second positioning members 904, 908 relative to each other and thereby non-movably retain the specimen 300. Compare FIGS. 37, 38, 40 and 36. That is, once the second positioning member 908 has been press fit into the opening 970 at a particular depth (e.g., such that the elastically deformable portion 924 of the second positioning member 908 at least partially contacts and at least partially deforms about a portion of a specimen 300), the second positioning member 808 (e.g., and specimen 300) may remain within the opening 970 at the particular depth (e.g., even if the apparatus 900 is rotated upside down) until the second positioning member 908 is manually removed from the opening via an external force (e.g., via grasping and forcibly removing the second positioning member 908 from the opening 970).

In another arrangement, the first positioning member 904 may include at least one restraint member 976 (e.g., protrusion, clip, latch, rib, etc.) extending partially into the opening 970 and that is configured to restrain the second positioning member 908 within the opening 970 of the first positioning member 904 against movement out of the opening 970 (e.g., in a direction away from the elastically deformable portion 916 of the first positioning member 904). For instance, the restraint member 976 may be positioned adjacent an entrance to the opening 970 (e.g., adjacent the upper portion 972 of the body 912). In one arrangement, the restraint member 976 may be in the form of a protrusion or ledge that protrudes into the opening 970 about a periphery of the entrance to the opening 970. As just one example, the upper portion 972 of the body 912 may include a rigid board 978 or the like (e.g., constructed of any appropriate low attenuating or radiolucent material) having an opening therethrough that is aligned with the opening 970, where an inner cross-dimension (e.g., inner diameter) of the opening of the board 978 is less than that of the opening 970 to create the restraint member 976. In this regard, the second positioning member 908 may be inserted into the opening 970 such that an upper portion 926 of the second positioning member 908 is urged (e.g., snaps) past the restraint member 976; at this point, the restraint member 976 may restrain or limit removal of the second positioning member 808 from the opening 870 (e.g., in the absence of an external force).

Various other forms of restraint members are envisioned and encompassed herein. In one arrangement, the restraint member 976 may be an integral portion of the body 912 of the first positioning member 904 that protrudes into the opening 970. As another example, the second positioning member 908 may include one or more grooves (e.g., a series of grooves) about an outer periphery of the body 920 that are each configured to receive the restraint member 976. For instance, a user could insert the second positioning member 908 into the opening 970 towards a specimen 300 until the specimen provides at least some resistance to movement. The user may then release the second positioning member 908 so that the restraint member 976 enters a closest groove at which point the first and second positioning members 904, 908 may be fixably positioned relative to each other and the specimen may be non-movably retained in the apparatus 900. In this regard, the restraint member 976 may be configured to ratchet into and past each respective groove until seating in a particular groove. Of course, the restraint member 976 could also be positioned on the second positioning member 908 and one or more grooves or openings could be disposed on the first positioning member 904 (e.g., on an inside surface of the opening 970). While the opening 970 of the first positioning member and the body 920 of the second positioning member 908 have been illustrated as being generally rectangular in shape, various other shapes are also envisioned (e.g., circular, etc.).

In use, a surgeon or other medical personnel may place an excised tissue specimen 300 onto the elastically deformable portion 916 of the first positioning member 904 within the opening 970. See FIG. 38. The positioning apparatus 800 may then be oriented at a first orientation relative to a support surface (e.g., horizontal surface, not shown) and the specimen 300 may be imaged along a first axis 940 through the apparatus 900 and specimen support volume 928 to obtain a first image of the specimen 300 (imaging source and detector not shown). See FIG. 39. For instance, the apparatus 900 may be positioned so that the imaging axis 412 of an imaging signal 400 (e.g., electromagnetic radiation signal, such as an x-ray) is coincident with and/or substantially parallel to the first axis 940 through the apparatus, where the first axis 140 is substantially perpendicular to the elastically deformable portions 916, 924 of the first and second positioning members 904, 908.

Figure 39:
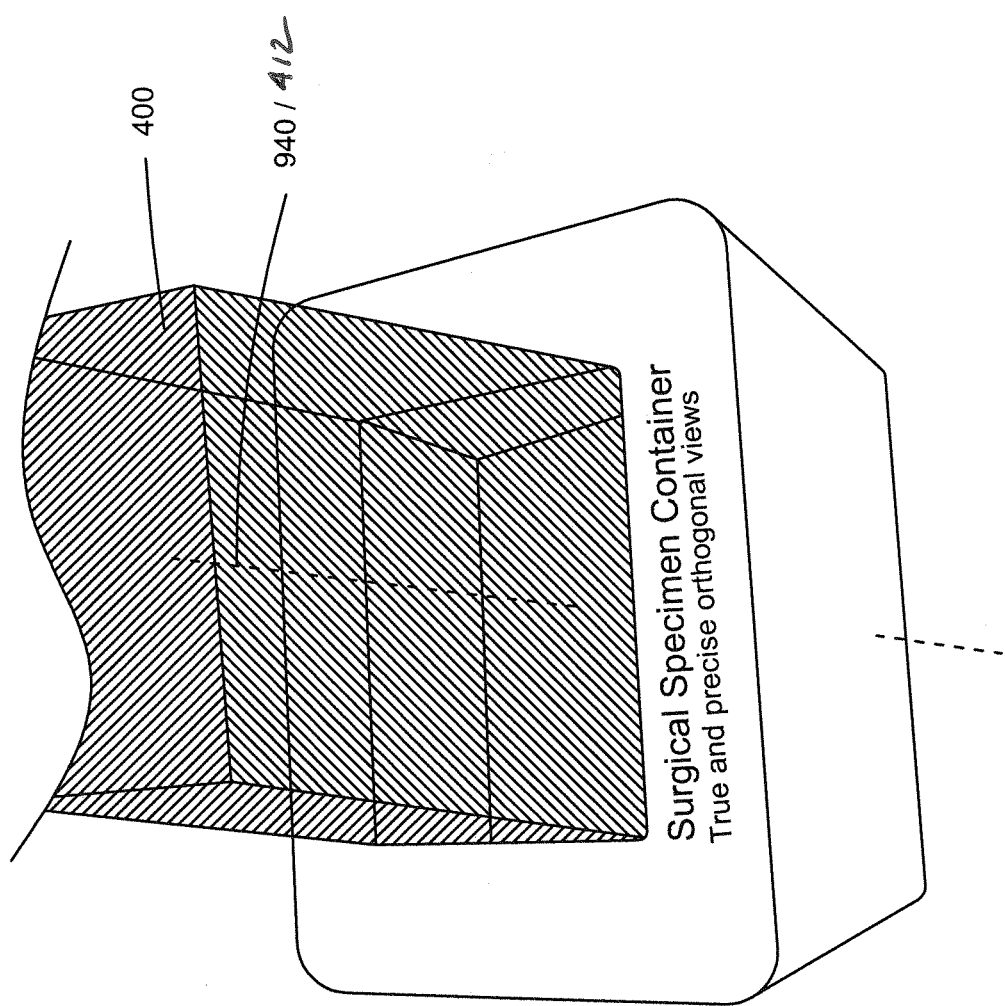
FIG. 39 is a perspective view similar to FIG. 38 and showing an imaging signal passing through the specimen along a first axis through the apparatus.
Figure 40:
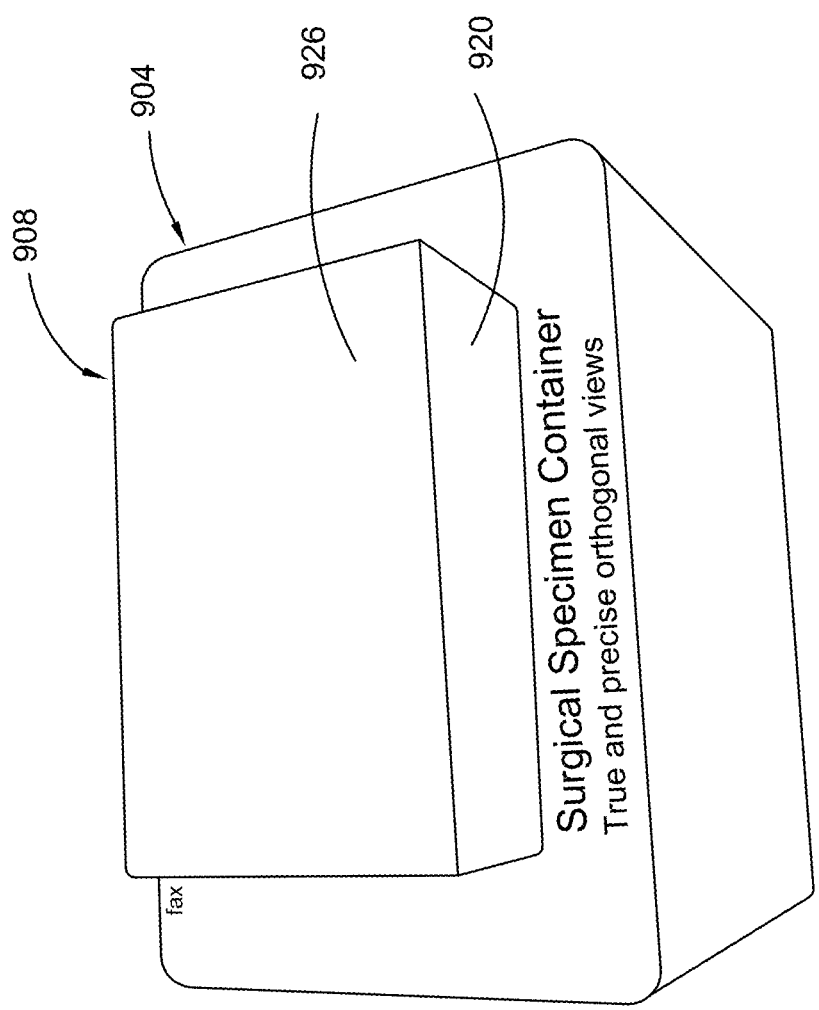
FIG. 40 is a perspective view of the specimen holding apparatus of FIG. 39 and showing a second positioning member being inserted into the opening of the first positioning member.
Figure 41:
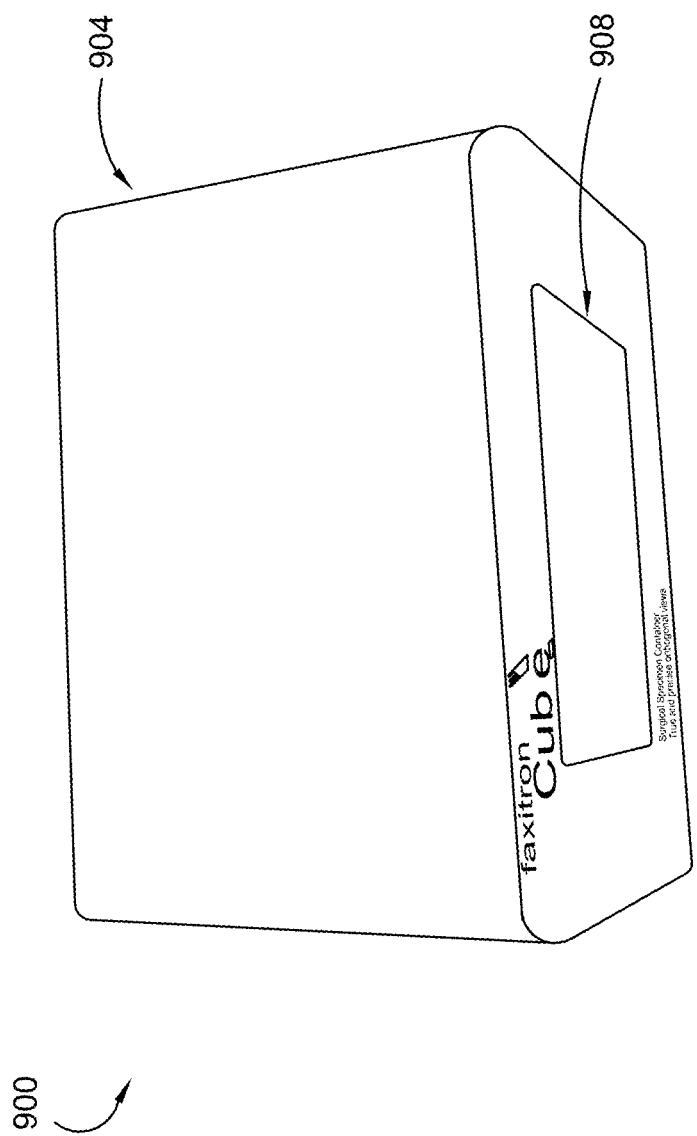
FIG. 41 is a perspective view of the specimen holding apparatus of FIG. 40 but in a second orientation.
Figure 42:
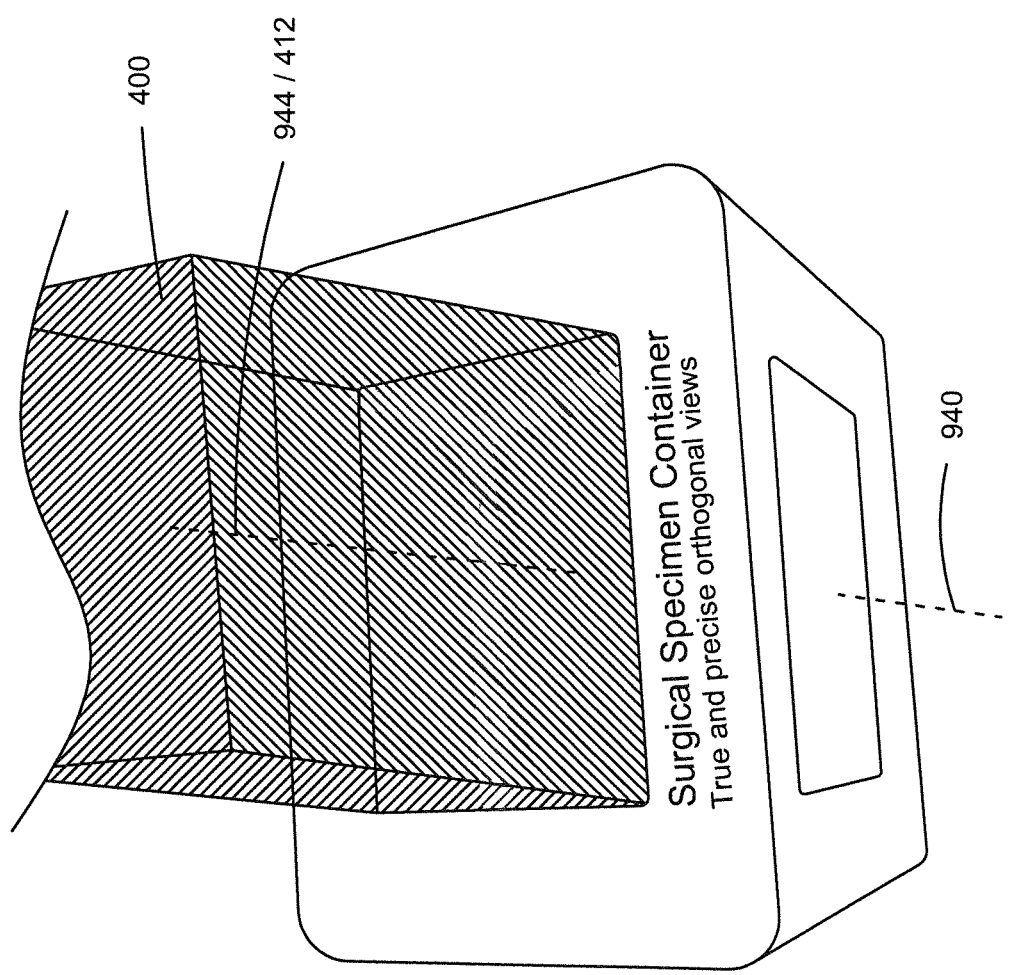
FIG. 42 is a perspective view similar to FIG. 41 and showing an imaging signal passing through the apparatus along a second axis.

In one arrangement, the specimen 300 may be imaged along the first axis 940 without the second positioning member 908 being positioned within the opening 970 of the first positioning member 904 as shown in FIG. 39 (e.g., to reduce any signal attenuation along the first axis 940 during the imaging). In another arrangement, the specimen 300 may be imaged along the first axis 940 with the second positioning member 908 being positioned within the opening 970 of the first positioning member 904 (e.g., as in FIG. 36). For instance, the second positioning member 908 may be inserted into the opening 970 so that the elastically deformable portions 916, 924 of the first and second positioning members 904, 908 at least partially elastically deform about opposite first and second portions of the specimen 300 (e.g., similar to FIG. 5) and so that the first and second positioning members 904, 908 are fixably positioned relative to each other as discussed above. While not shown, a reference plane (e.g., reference plane 200 of FIGS. 4-7) may be defined between the elastically deformable portions 916, 924 of the first and second positioning members 904, 908. In this case, the imaging signal 400 would travel along the imaging axis 412 and first axis 940 through the second positioning member 908, the specimen 300, and then the first positioning member 904 before being received at a detector (not shown), where the imaging signal 400 is perpendicular to the reference plane. In any case, and after the specimen has been imaged along the first axis 940 and the second positioning member 908 has been inserted into the opening 970 to fixably retain the specimen 300 against movement between the elastically deformable portions 916, 924 of the first and second positioning members 904, 908, the positioning apparatus 900 may be reoriented into a second orientation relative to the support surface (e.g., such as 90° relative to the first orientation, see FIG. 41) and then the specimen 300 may be imaged along a second axis 944 (orthogonal to first axis 940 and along or coincident with the reference plane between the elastically deformable portions 916, 924 of the first and second positioning members 904, 908) through the apparatus 900 to obtain a second image of the specimen 300 (see FIG. 42, specimen not shown because it is disposed within apparatus 900, but similar to FIG. 7). Advantageously, the specimen 300 may remain substantially fixed or non-movable within the specimen support volume 928 of the apparatus 900 as the apparatus 900 is being reoriented (e.g., due at least in part to the first and second elastically deformable portions 916, 924).

The bodies 912, 920 of each of the first and second positioning members 904, 908 (e.g., and thus the elastically deformable portions 916, 924) may be substantially or fully constructed of any appropriate radiolucent solid material (e.g., polymeric foam(s), such as respective blocks of solid foam) to allow the imaging signal 400 to be transmitted therethrough along the first and second orthogonal axes 940, 944 through the apparatus 900 (e.g., including through the specimen support volume 928) to obtain the respective first and second images of the specimen (e.g., for use in specimen margin verification and the like). As mentioned previously, the low density and substantially uniform, homogeneous material properties of solid foams substantially eliminates or at least reduces attenuation of the imaging signal 400 passing through the apparatus 900 and thus substantially eliminates or at least reduces the likelihood of the apparatus appearing in the images of the specimen 300 while correspondingly increasing the quality (e.g., contrast, resolution, etc.) of the images (e.g., for use in verifying tissue margins, identifying suspicious locations or areas in the excised tissue specimen to be subsequently analyzed by a pathologist, and/or the like).

Turning now to FIGS. 43-49c, another embodiment of the apparatus 900' is disclosed and broadly includes a first or lower positioning member 904' having a body 912' and an at least partially elastically deformable portion 916' (e.g., a "retention" portion or member) formed by an inner bottom surface 971' of the body 912' that partially delimits an opening 970' of the body 912', and a second or upper positioning member 908' having a body 920' and an at least partially elastically deformable portion 924' (e.g., a "retention" portion or member). One difference between the apparatus 900' and the apparatus 900' is that the apparatus 900' includes at least a first orientation marker 1000 positioned on or embedded within the body 912' of the first positioning member 904' (see FIGS. 45-47c) that is configured to facilitate generation of a corresponding object in a resultant image that provides a point of reference for the tissue specimen in the resultant image to assist technicians in interpreting the image as described below.

Figure 51:
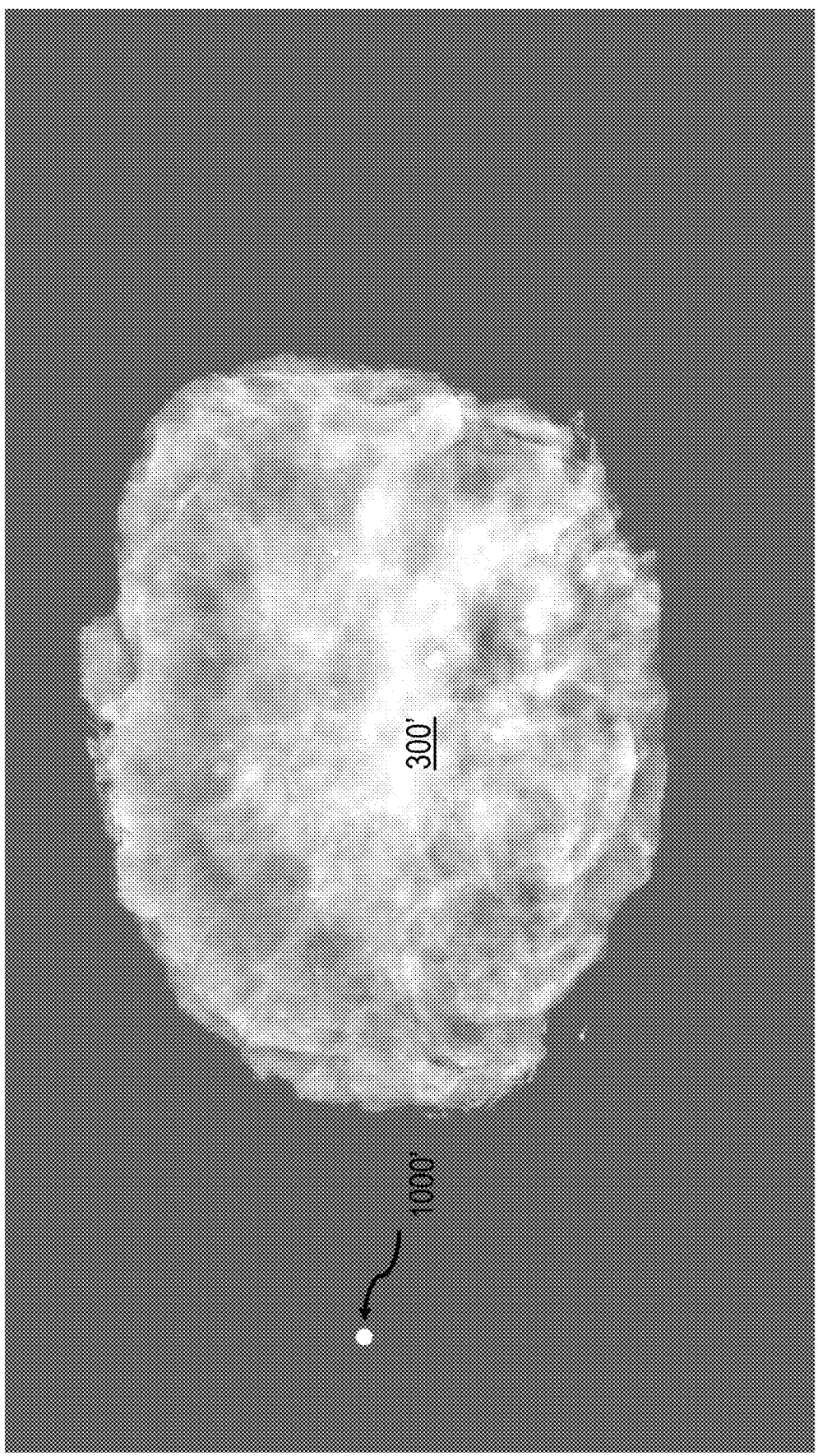
FIG. 51 is an anterior-posterior image of the tissue specimen of FIG. 50 with the second positioning member being received in the opening of the first positioning member and the apparatus being oriented at a first orientation relative to a support surface, where the orientation marker object of the first positioning member is displayed to the left of the tissue specimen to indicate to a technician that the tissue specimen in the image is from a right breast.

The first orientation marker 1000 may be made of any appropriate material(s) denser than and/or less radiolucent than is the body 912' of the first positioning member 904' (e.g., one or more metals such as lead, steel, stainless steel, brass, bronze, aluminum titanium, tungsten carbide, and/or the like to at least partially inhibit transmission of an imaging signal (e.g., imaging signal 400 of FIGS. 39 and 42) therethrough (i.e., through the first orientation marker 1000) so that a corresponding first object 1000' (e.g., a lighter area, such as a lighter circular area in the case of a spherical orientation marker, see FIG. 51) appears in the resultant image and is spaced from (i.e., non-coincidental with) the tissue specimen in the resultant image. In one arrangement, the first orientation marker 1000 may have a density of at least about 1000 kg/m3 (e.g., that of $H_2O$). For instance, the first orientation marker 1000 may include one or more metals such as lead, steel, stainless steel, brass, bronze, aluminum titanium, tungsten carbide, and/or the like. As another example, the first orientation marker 1000 may be in the form of a drop of any appropriate radio-opaque ink. For instance, the radiopaque ink drop may be injected into an appropriate location within or on the first positioning member 904'

Figure 52:
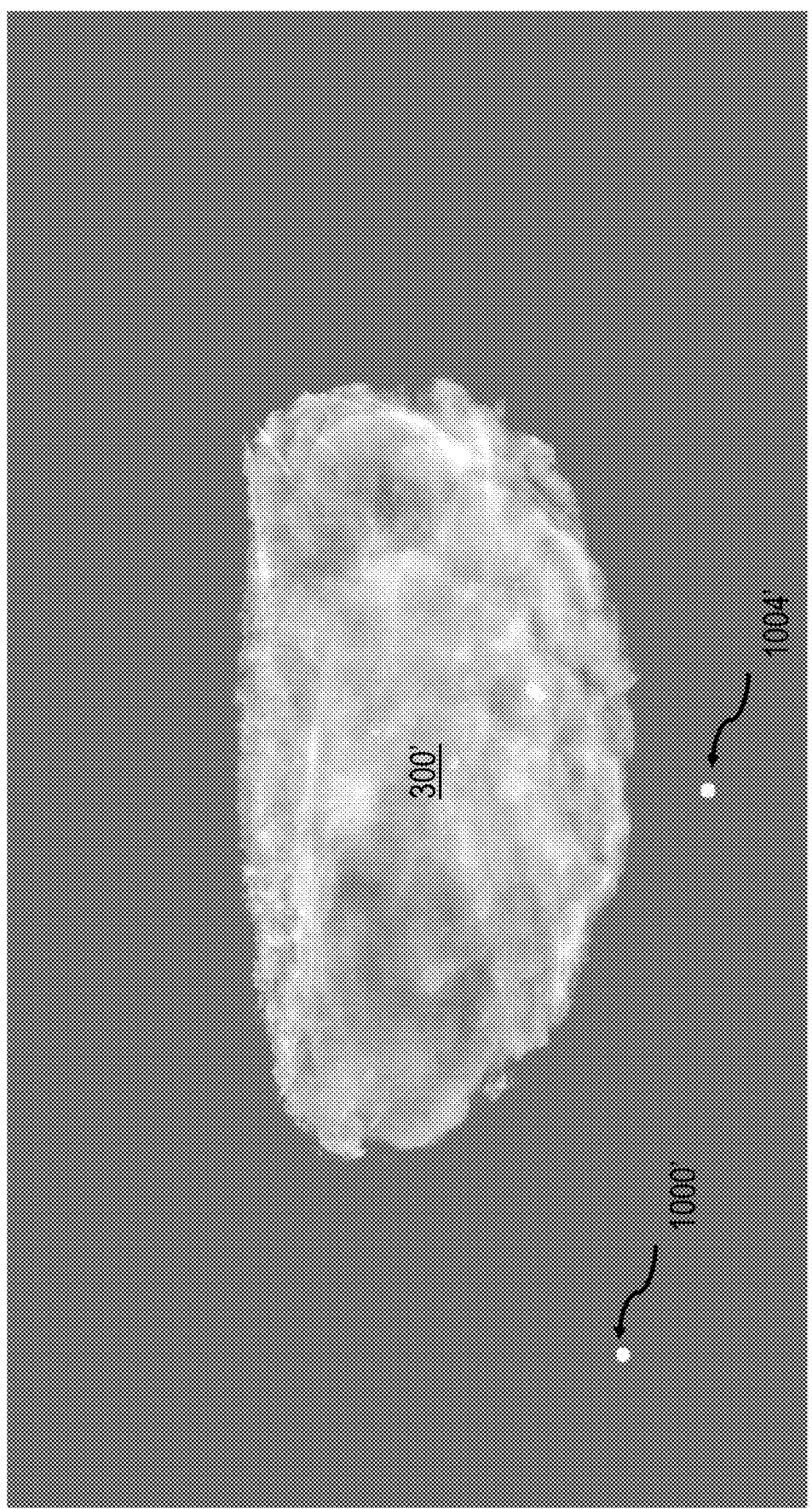
FIG. 52 is an cranial-caudal image of the tissue specimen of FIG. 50 with the second positioning member being received in the opening of the first positioning member and the apparatus being oriented at a second orientation relative to a support surface that is 90° different than the first orientation, where the orientation marker object of the second positioning member is displayed below the tissue specimen to indicate an approximate location of the patient's nipple and the orientation marker object of the first positioning member is displayed to the left of the tissue specimen to indicate to a technician that the tissue specimen in the image is from a right breast.

The first orientation marker 1000 may also be of any appropriate shape (e.g., spherical, rectangular strip, etc.) and size. As just one example, the first orientation marker 1000 may, in one embodiment, be in the form of a spherical ball of metal (e.g., lead shot) having a diameter of at least about 0.5 mm, such as at least about 1 mm. As another example, the first orientation marker 1000 may be in the form of a spherical ball of metal having a diameter not greater than about 5 mm, such as not greater than about 4 mm. In the case of the tissue specimen 300 being from a patient's right breast, for instance, the first object 1000' in the resultant image may be spaced from the tissue specimen 300' and positioned to the left of the tissue specimen 300' (e.g., in the case of an anterior posterior image as in FIG. 51 or a cranial caudal image as in FIG. 52) to represent the left breast and thereby provide a visual confirmation to a technician or doctor that the specimen in the image is in fact from the patient's right breast. Even though the imaging signal 400 of FIGS. 39 and 42 appears to only be traveling through a portion of the apparatus, it is to be understood that the imaging signal 400 may actually extend across an entirety of the footprint of the apparatus and thus through an entirety of the apparatus.

The first orientation marker 1000 may be at least partially embedded or formed in any appropriate manner within or on a sidewall 975' of the body 912' of the first positioning member 904' that generally surrounds the opening 970' of the first positioning member 904'. In one arrangement, the first orientation marker 1000 may be disposed within or at least one the sidewall 975' at a location that is between opposite inner and outer surfaces 976',978' of the body 912' (where the inner surface 976' generally surrounds and delimits a side portion of the opening 970') to create a gap or space between a tissue specimen 300 received in opening 970' and the first orientation marker 1000 and thus between the tissue specimen and the first object 1000' in a resultant image thereof (e.g., in the case of an anterior posterior image as in FIG. 51 or a cranial caudal image as in FIG. 52). In another embodiment, the first orientation marker 1000 may be fully embedded within the sidewall 975' so that is it disposed between opposite upper and lower surfaces 972',974' of the body 912', between the opposite inner and outer surfaces 976',978' of the body 912', and between front and rear surfaces 980',982' of the body 912' (as indicated by the arrows in FIG. 46). The first orientation marker 1000 may be embedded within and/or otherwise attached to the sidewall 975' as part of the initial manufacturing of the body 912' (e.g., such as by appropriate positioning the first orientation marker 1000 within a mold into which a polymeric material or the like is to be injected) or after the body 912' is manufactured (e.g., such as by using any appropriate tool to apply the marker to the sidewall 975' or insert the marker into the sidewall 975'.

In one arrangement, the apparatus 900' may additionally include a second orientation marker 1004 positioned on or embedded within the body 920' of the second positioning member 908' (see FIGS. 45 and 48-49c) that is configured to facilitate generation of a corresponding object in the resultant image that provides a second point of reference for the tissue specimen in the resultant image to assist technicians in interpreting the image. Like the first orientation marker 100, the second orientation marker 1004 may be made of any appropriate material(s) denser than and/or less radiolucent than is the body 920' of the second positioning member 908' to at least partially inhibit (e.g., absorb) transmission of an imaging signal therethrough (i.e., through the second orientation marker 1004) so that a corresponding second object 1004' (e.g., a lighter area, such as a lighter circular area in the case of a spherical orientation marker, see FIG. 51) appears in the resultant image and is configured to be spaced from (i.e., non-coincidental with) or encompassed within (e.g., coincidental with) the tissue specimen in the resultant image depending on orientation of the apparatus 900' (e.g., of a reference plane between the deformable portions of the first and second positioning members 904', 908 when the first and second positioning members are fixably positioned relative to each other) relative to the imaging axis (e.g., imaging axis 412 of FIGS. 39 and 42).

In one arrangement, the second orientation marker 1004 may be made of the same material(s) as the first orientation marker 1000, constructed in the same manner as the first orientation marker 1000, and incorporated into the apparatus 900' in the same manner as the first orientation marker 1000. In another arrangement, the first and second orientation markers 1000, 1004 may be made of different materials, constructed differently, and/or incorporated into the apparatus 900' differently.

In one arrangement, the second orientation marker 1004 may be positioned or fixed on or over the upper surface 926' of the body 920' of the second positioning member 908 in any appropriate manner. In another arrangement, the second orientation marker 1000 may be fully embedded within the body 920' in any appropriate manner so that it is disposed between the upper and lower surfaces 926',924' of the body 920', between the opposite left and right outer surfaces 984',986' of the body 920', and between front and rear surfaces 988',990' of the body 920' (as indicated by the arrows in FIG. 48).

Figure 43:
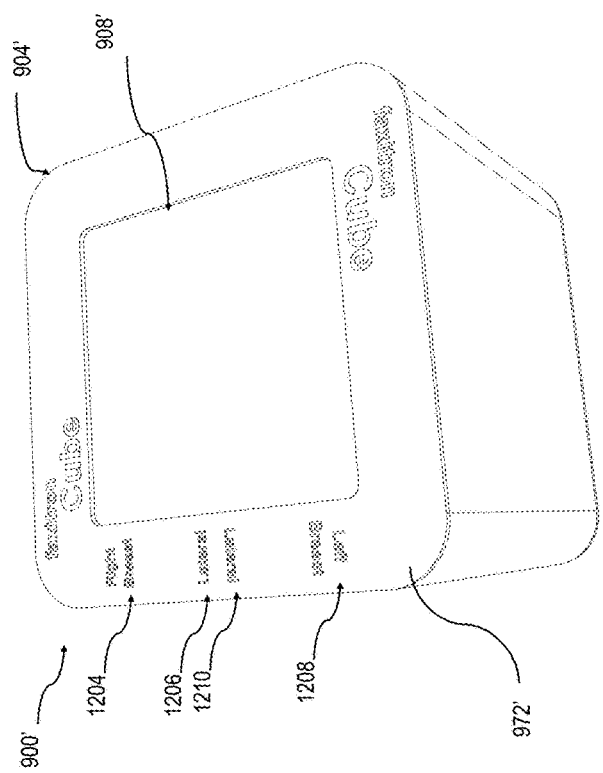
FIG. 43 is a perspective view of a specimen holding apparatus according to another embodiment.
Figure 44:
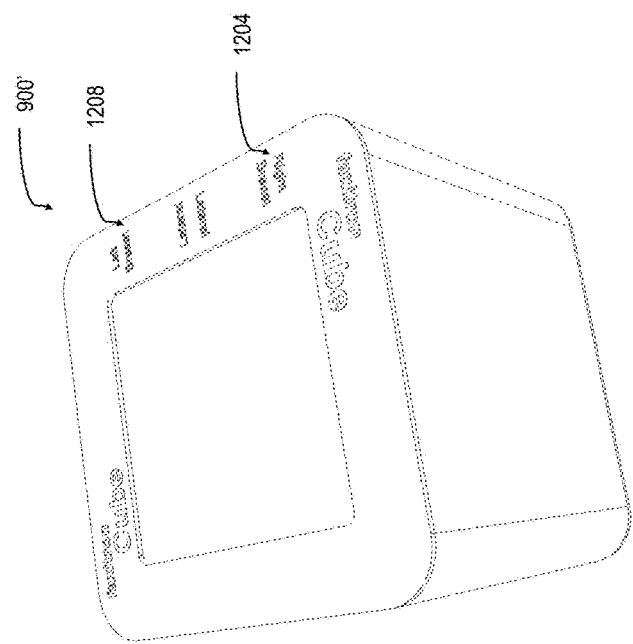
FIG. 44 is an opposite perspective view of the specimen holding apparatus of FIG. 43.
Figure 45:
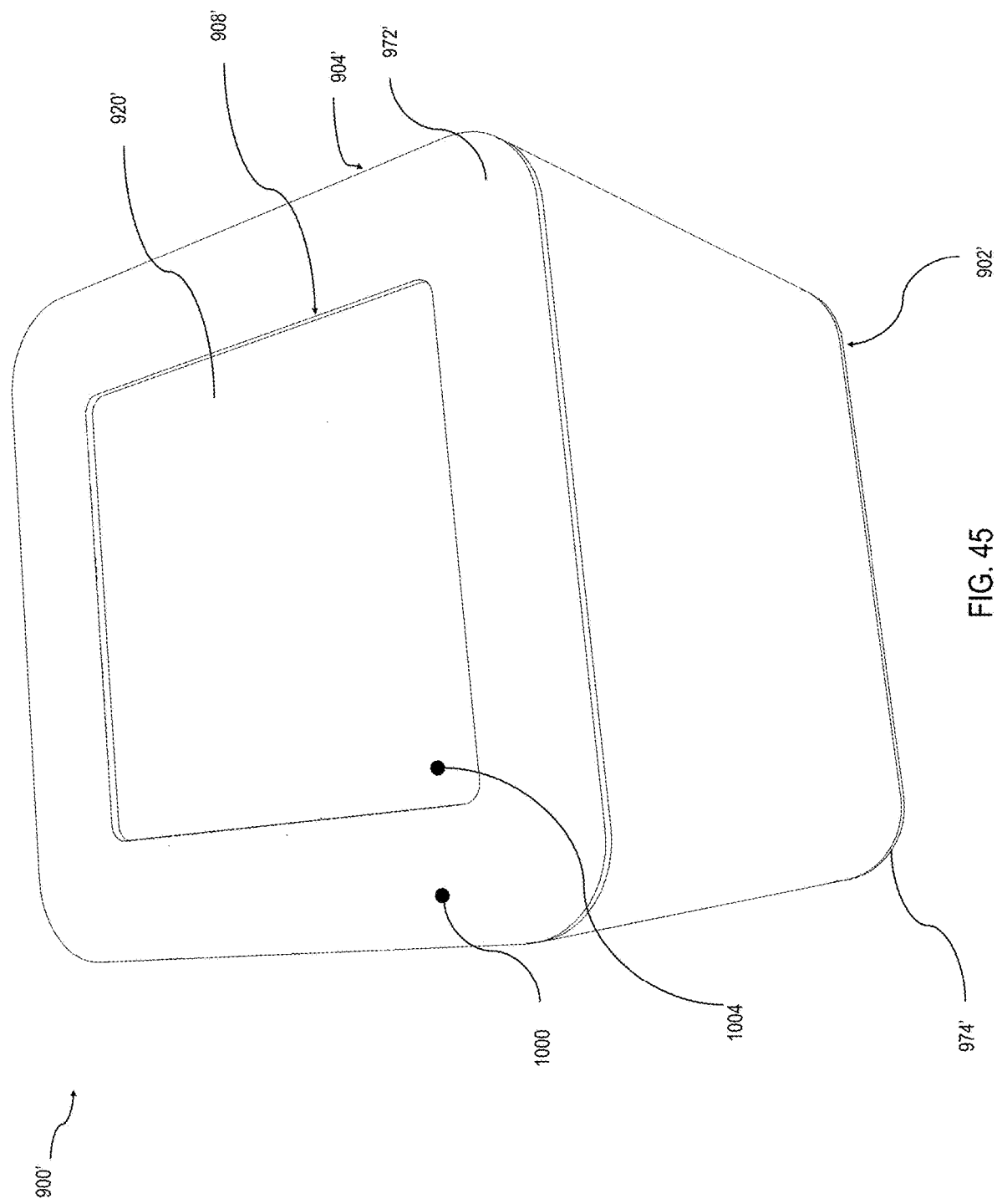
FIG. 45 is another perspective view of the specimen holding apparatus of FIG. 43 and illustrating orientation markers embedded within first and second positioning members of the apparatus.
Figure 46:
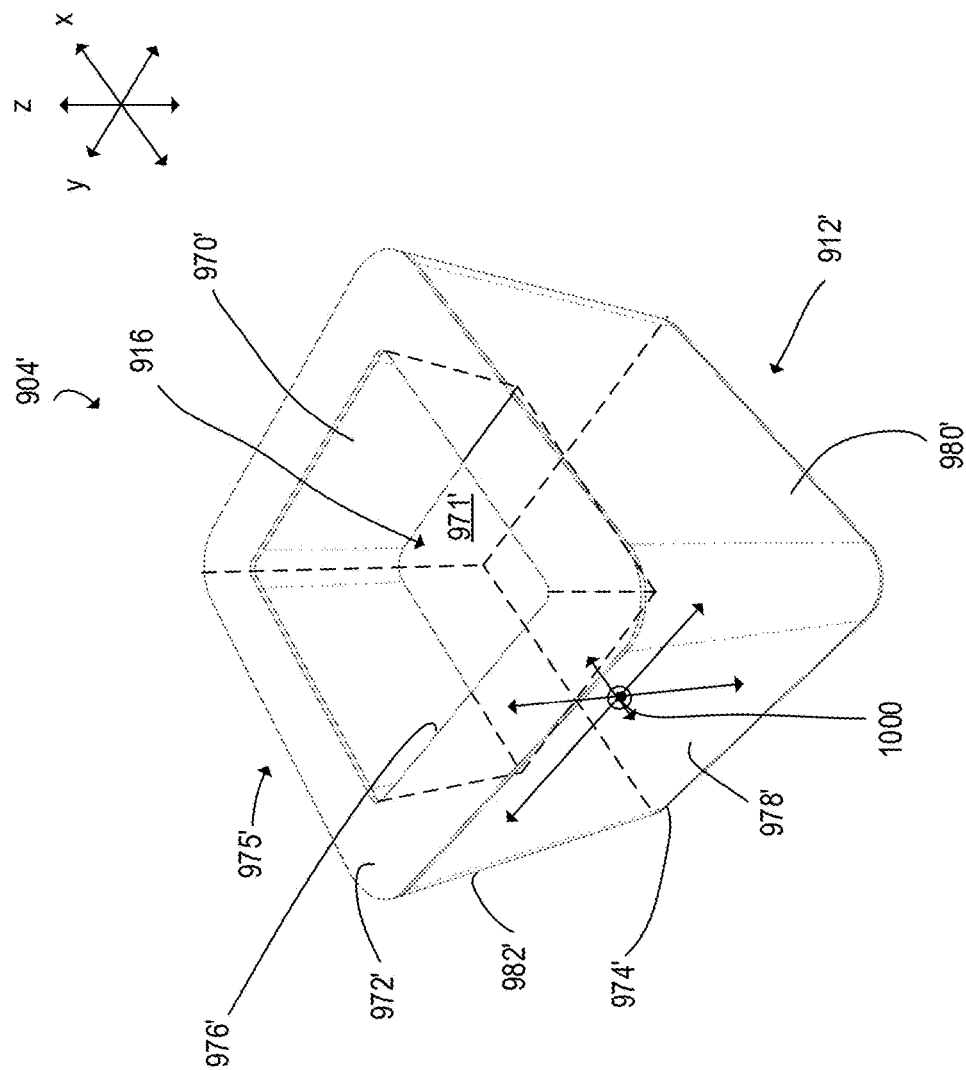
FIG. 46 is a perspective view of the first positioning member of the apparatus of FIG. 45 and showing an orientation marker embedded therein.
Figure 48:
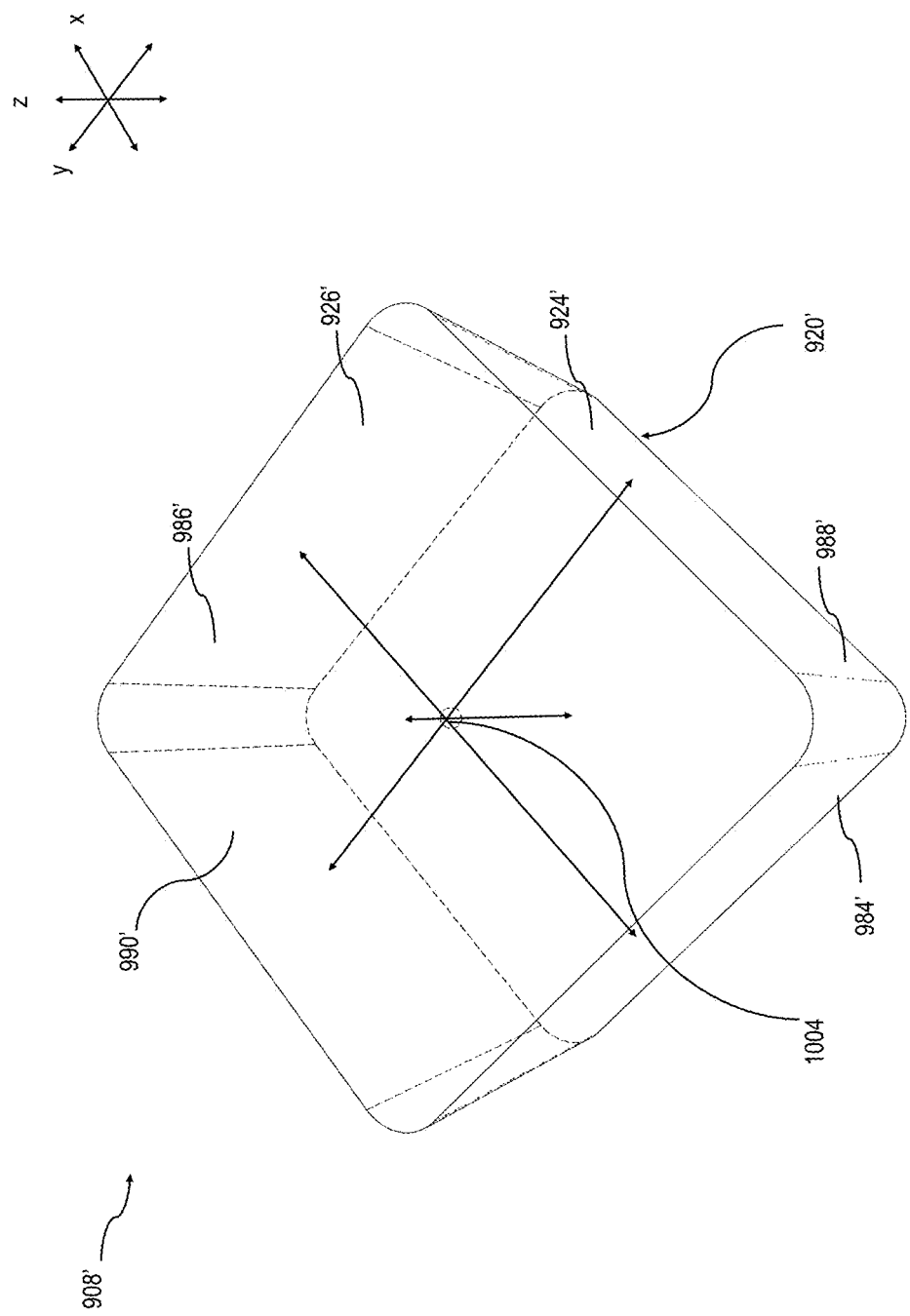
FIG. 48 is a perspective view of the second positioning member of the apparatus of FIG. 45 and showing an orientation marker embedded therein.
Figure 49:
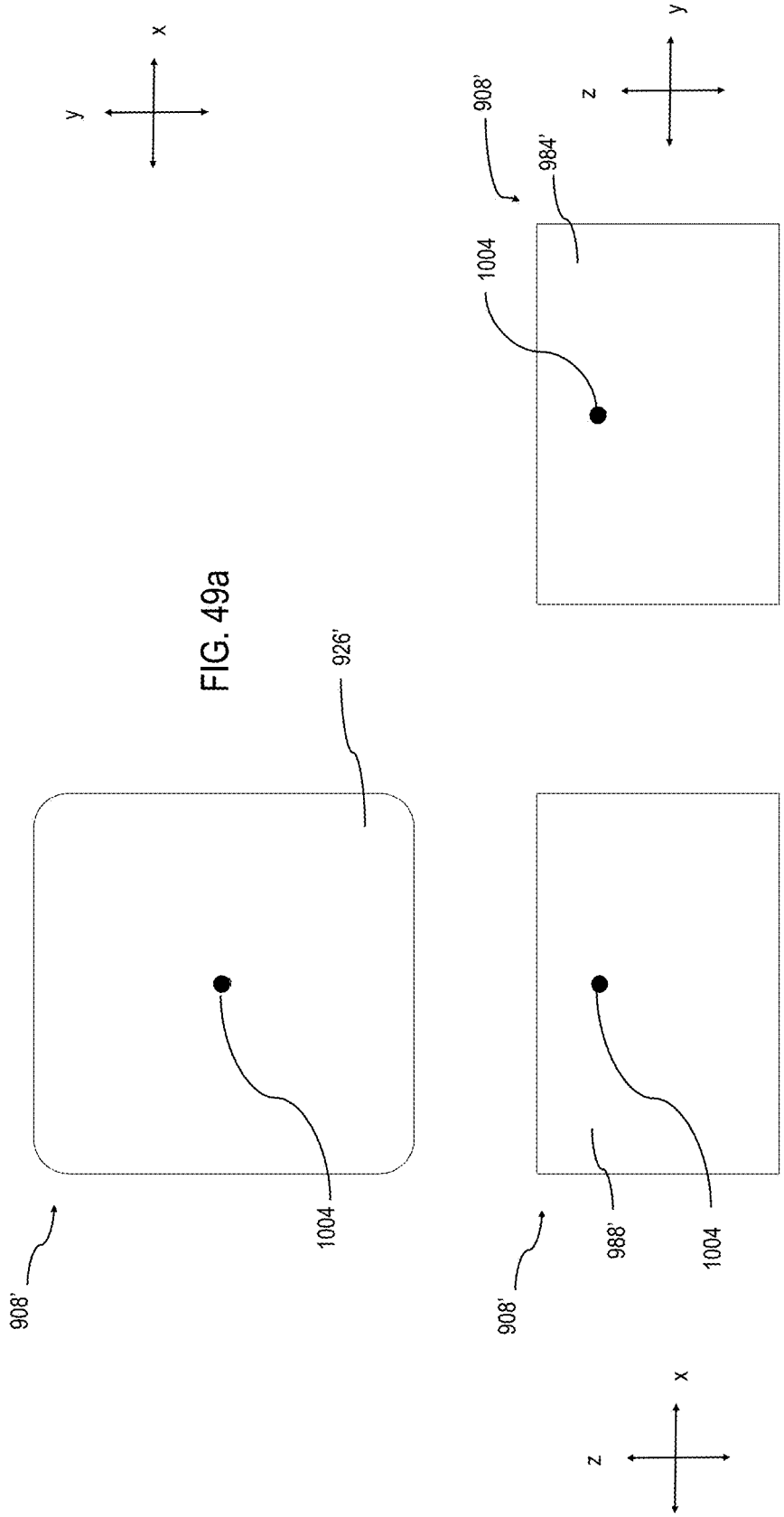
FIGS. 49a-49c are top, front and side view of the second positioning member of FIG. 46.

In one embodiment, a portion of the body 912' of the first positioning member 904' (e.g., the upper surface 972') may include one or more indicators 1200 (e.g., words, graphics, logos, designs, textures, colors, etc.) that broadly facilitate use of the apparatus 900' by a technician, surgeon and/or other personnel. For instance, one indictor 1204 may convey that the tissue specimen to be received in the opening 970' of the first positioning member for subsequent imaging is to be from the right breast, such as when the indictor 1204 is readable in an upright manner as shown in FIG. 43. In conjunction with the indicator 1204, another indictor 1206 may be included that is generally positioned over the portion of the sidewall 975' in which the first orientation marker 1000 is located and that is readable in an upright manner when the indictor 1204 is readable in an upright manner. The indicator 1206 conveys to the technician or surgeon the general location of the first orientation marker 1000 and thus a left breast relative to the specimen of the right breast received in the opening 970' of the first positioning member 904'. The body 912' may also include corresponding indicators 1208, 1210 that are rotated 180° relative to the indicators 1204, 1206 and that convey to the surgeon or technician that a specimen of a left breast is to be received in the opening 970' of the first positioning member 904' and the general location of the first orientation marker 1000 and thus a right breast relative to the specimen of the left breast when read in an upright manner as in FIG. 44. Other manners of conveying to the surgeon or technician proper use of the apparatus 900' are also envisioned and included herein.

Figure 50:
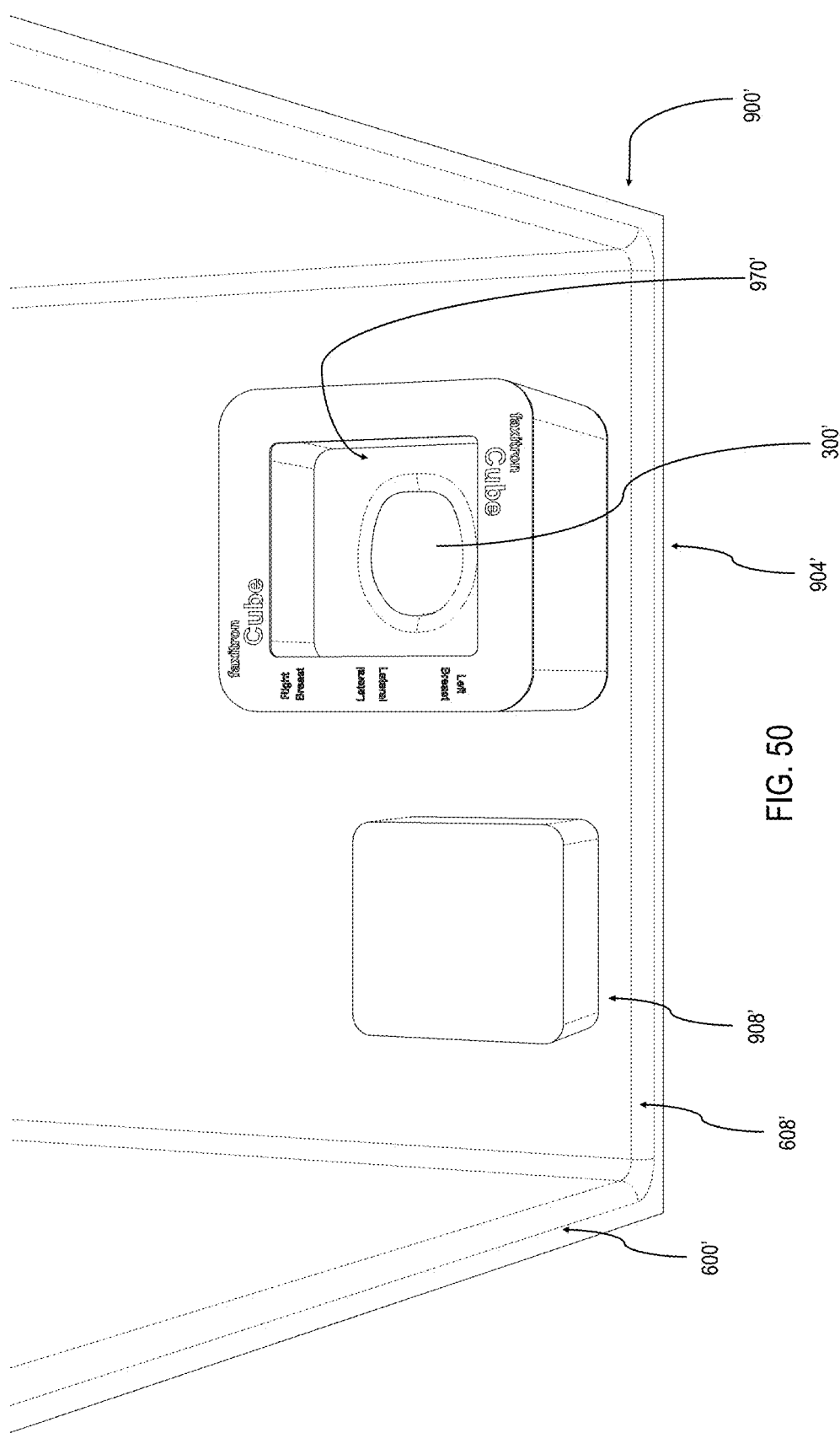
FIG. 50 is a perspective view of the apparatus of FIG. 43 with the second positioning member being removed from the first positioning member and a tissue specimen of a right breast being received in an opening of the first positioning member.

In use, a surgeon or other medical personnel may determine whether an excised tissue specimen 300 is from a patient's right or left breast, and then place the specimen 300 onto the elastically deformable portion 916 of the first positioning member 904 within the opening 970' with the first orientation marker 1000 in an appropriate position, such as to the left of the specimen in the case of a right breast or vice versa. See FIGS. 46 and 50. As discussed above, the indicators 1200 may facilitate this process. The apparatus 900' may be oriented at a first orientation or position relative to a support surface (e.g., horizontal surface of chamber 608' of imaging system 600' of FIG. 50) and an imaging signal may be transmitted through the first positioning member 904' and the specimen 300 for generation of a corresponding image.

In the first orientation or position, for instance, the bottom surface 974' of the first body 912' of the first positioning member may be placed against the horizontal surface, an imaging signal may be transmitted through the apparatus 900' such that the imaging signal is perpendicular to the reference plane between the first and second positioning members 904',908', and a first image may be subsequently generated. See anterior posterior image of FIG. 51. As shown, the first object 1000' (corresponding to the first orientation marker 1000) may be spaced from the specimen 300' on the left side of the specimen 300' to indicate to a surgeon or technician that the specimen 300' is from a patient's right breast. In one arrangement, the second positioning member 908 may be inserted into the opening 970' to fixably retain the specimen 300 against movement between the elastically deformable portions 916, 924 of the first and second positioning members 904',908' before transmission of the imaging signal and generation of the first image. In this regard, the imaging signal may be transmitted through the first and second positioning members 904',908' and the specimen 300 and the first image may additionally include a second object (not shown in FIG. 51) corresponding to the second orientation marker 1004 that is fully subsumed or encompassed within the specimen 300' to provide an additional indication that the image is an anterior posterior image.

In any case, the apparatus 900' or reference plane may then be reoriented from the first orientation to a second orientation relative to the imaging axis or support surface (e.g., such as by 90° or the like). If not already done so, the second positioning member 908 may be inserted into the opening 970' to fixably retain the specimen 300 against movement between the elastically deformable portions 916, 924 of the first and second positioning members 904',908' before reorienting the apparatus 900' to the second orientation. For instance, the apparatus may be rotated by 90° so that the front or rear surface 980',982' of the first positioning member 904' is flat on the support surface and the reference plane is parallel to the imaging axis (where the position of the imaging axis through the apparatus 900' in the second orientation is 90° different than that in the first orientation). An imaging signal may then be transmitted through the apparatus 900' along the imaging axis and a second image may be generated. See cranial caudal image of FIG. 52. As shown, the first object 1000' (corresponding to the first orientation marker 1000) may be spaced from the specimen 300' on the left side of the specimen 300' to indicate to a surgeon or technician that the specimen 300' is from a patient's right breast. Furthermore, the second object 1004' may be spaced from the specimen 300' to provide an approximate location of the front or nipple of the breast.

The apparatus 900' or reference plane may then be reoriented from the second orientation to a third orientation relative to the imaging axis or support surface (e.g., such as by 90° or the like). For instance, the apparatus may be rotated by another 90° so that the outer surface 978' of the first positioning member 904' is flat on the support surface and the reference plane is parallel to the imaging axis (where the position of the imaging axis through the apparatus 900' in the third orientation is 90° different than that in each of the first and second orientations). An imaging signal may then be transmitted through the apparatus 900' along the imaging axis and a third image may be generated. See medial lateral image of FIG. 53. As shown, the second object 1004' may be spaced from the specimen 300' to provide an approximate location of the front or nipple of the breast. Furthermore, the first object 1000' may be spaced from the specimen 300' and positioned between the second object 1004' and the specimen 300'.

Figure 53:
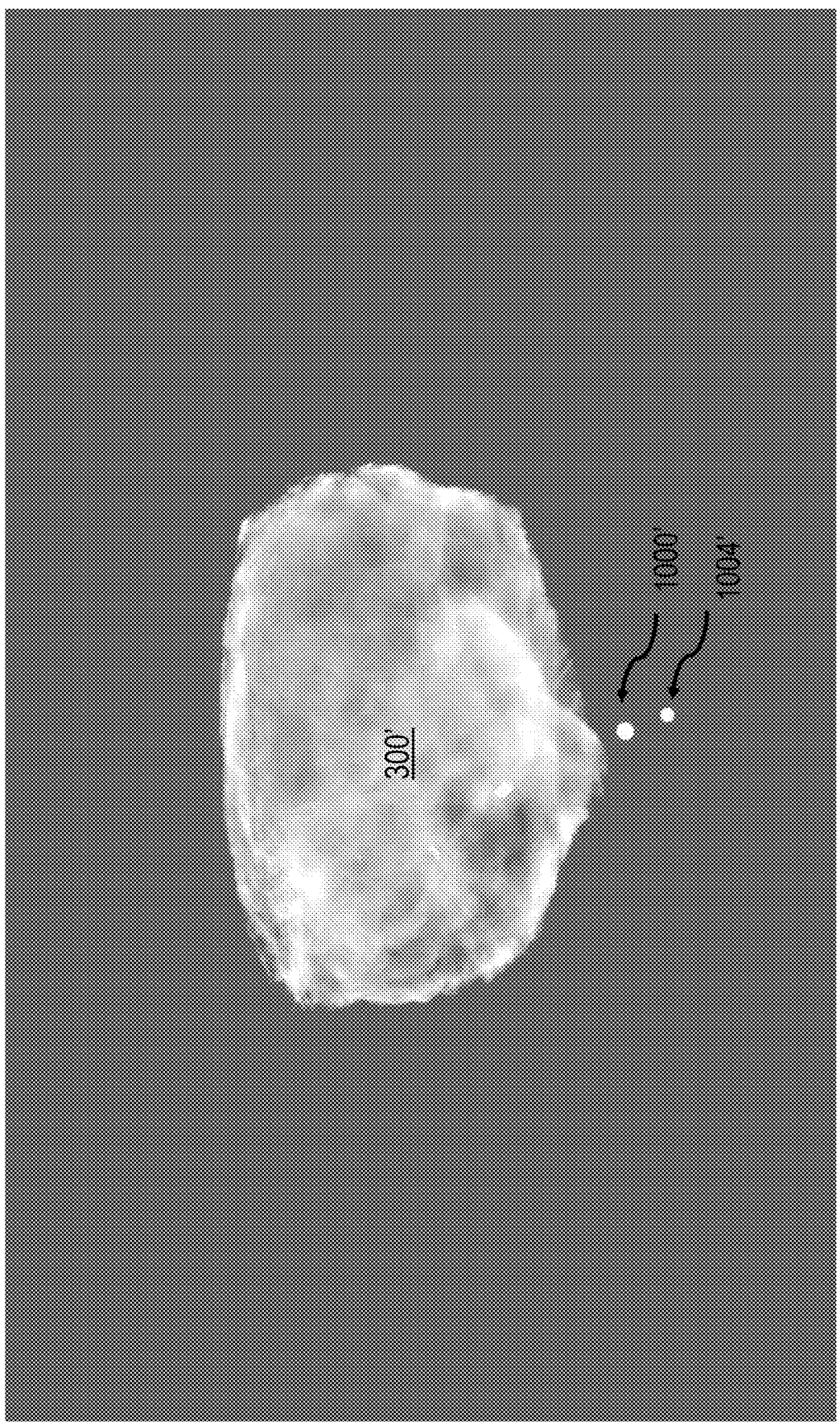
FIG. 53 is an medial-lateral image of the tissue specimen of FIG. 50 with the second positioning member being received in the opening of the first positioning member and the apparatus being oriented at a third orientation relative to a support surface that is 90° different than the first and second orientations, where the orientation marker object of the second positioning member is displayed below the tissue specimen to indicate an approximate location of the patient's nipple.
Figure 54:
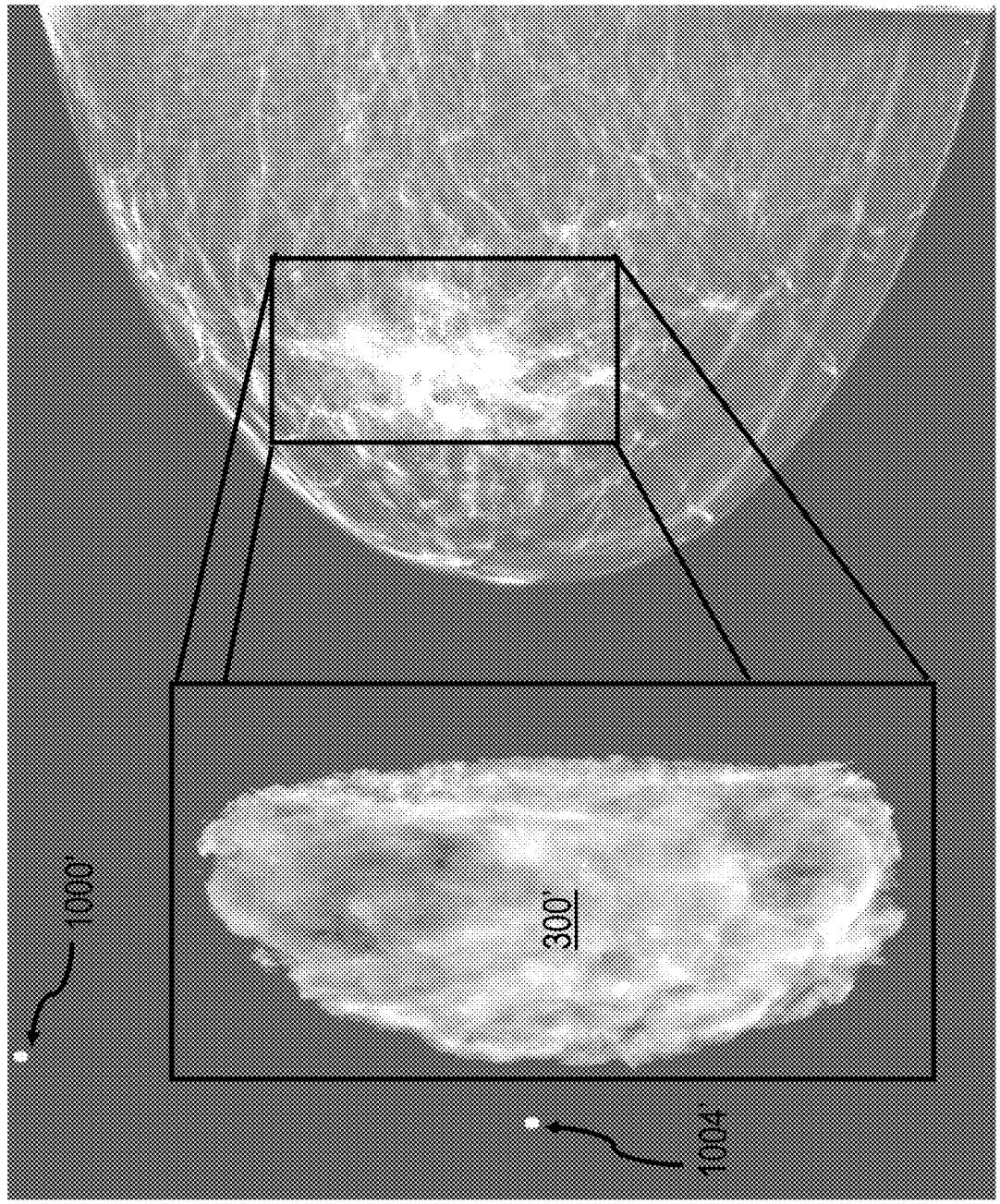
FIG. 54 is another view of the cranial-caudal image of FIG. 52 being displayed next to an original cranial-caudal mammogram of the right breast to allow a radiologist to determine if the tissue margins are sufficient.
Figure 55:
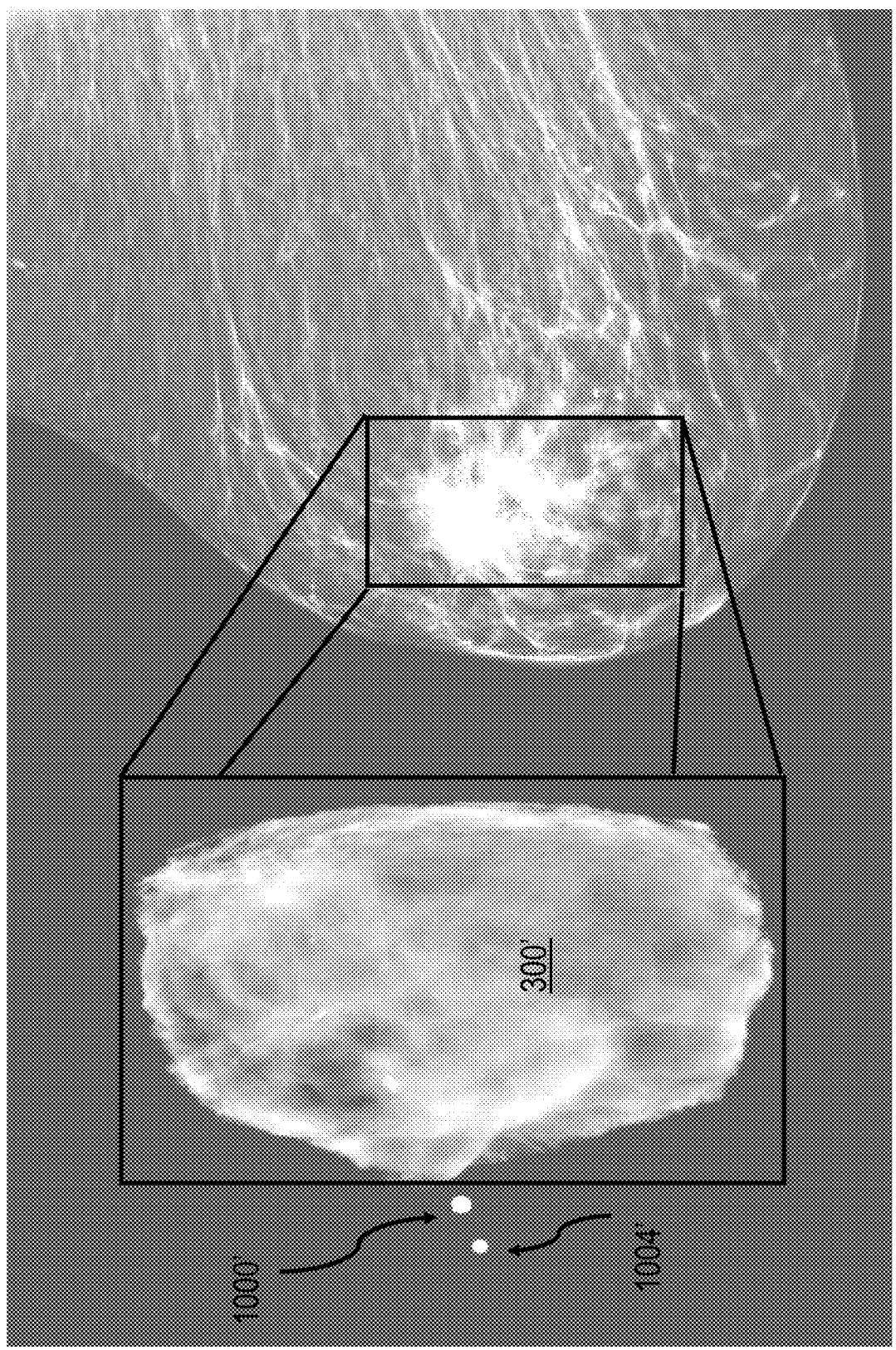
FIG. 55 is another view of the medial-lateral image of FIG. 53 being displayed next to an original medial-lateral mammogram of the right breast to allow a radiologist to determine if the tissue margins are sufficient.

In one arrangement, such as in the case where the first orientation marker 1000 is embedded within the sidewall 975' of the body 912' of the first positioning member 904' at a position below where a top of the specimen 300 is located within the opening 970', the first object 1000' may be encompassed within, overlap or otherwise be coincident with the specimen 300' in the third image of FIG. 53. In other words, it is not always necessary that the first orientation marker 1000 is embedded within the sidewall 975' of the body 912' of the first positioning member 904' at a position above where a top of the specimen 300 is located within the opening 970' (as is the case resulting in the third image of FIG. 53). The first, second and/or third images may be used to verify tissue margins as discussed herein. FIGS. 54-55 illustrate how the first and/or second objects 1000', 1004' may be used to orient the second and third images of FIGS. 52-53 relative to corresponding original cranial caudal and medial lateral mammograms of the patient's breast to determine sufficiency of the tissue margins of the specimen 300.

While first and second orientation markers 1000, 1004 have been disclosed herein, it is envisioned that additional orientation markers may be appropriately affixed to or embedded within the first and/or second bodies 912',920' to provide additional points of reference in resulting images. Furthermore, the apparatus 900' (and other apparatuses disclosed herein) is not limited to use with breast tissue and may be used with other types of tissue in which reference to other anatomical structures in resulting images is desired.

Figure 56:
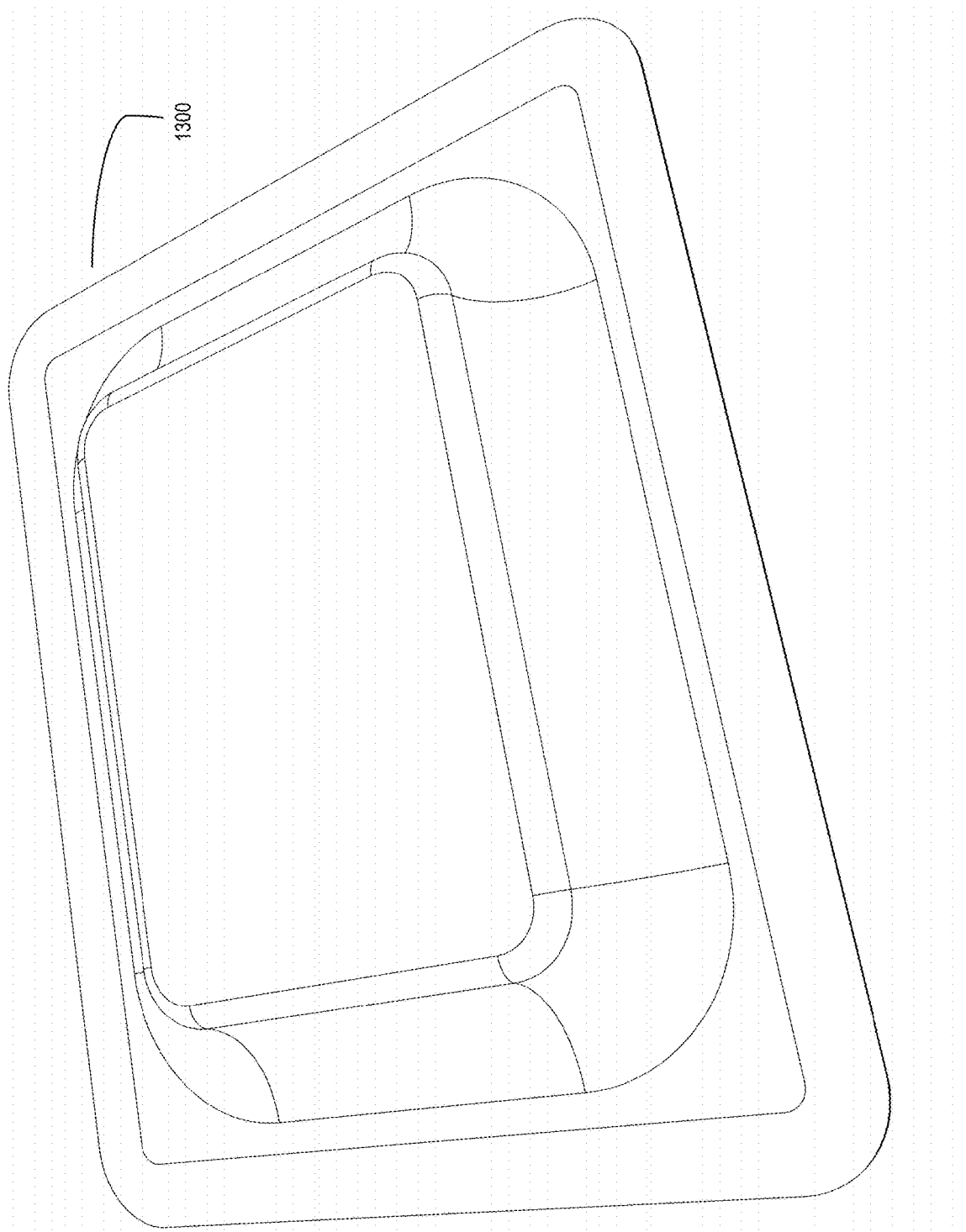
FIG. 56 is a perspective view of a packaging for a specimen holding apparatus according to one embodiment.

FIG. 56 presents a perspective view of a packaging 1300 that may be used ship and/or store one or more of the apparatuses disclosed herein (e.g., apparatus 100, apparatus 900, etc.). For instance, the packaging 1300 may be in the form of a gas-impermeable pouch or envelope (e.g., medical grade foil, metalized plastics, etc.) within which an apparatus disclosed herein is configured to be sealed. In the case where the apparatus is constructed substantially entirely of a polymeric foam or the like, evacuation of the interior of the packaging 1300 before sealing of packaging 1300 may cause the volume occupied by the apparatus to decrease, thus reducing the volume occupied by the packaged apparatus.

It is noted that in relation to at least some embodiments disclosed herein (e.g., the apparatuses 500, 500'), the frames/bodies of the first and second positioning members need not necessarily be constructed of a radiolucent or other low attenuating material due to the first and second volumes disclosed herein. It is also noted that most or all of the respective sets of first and second positioning members of the apparatuses disclosed herein may be identical to facilitate manufacturing and assembly of the apparatuses.

The description herein has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. For instance, various combinations and/or modifications of the embodiments disclosed herein are envisioned (e.g., as just one example, utilizing the first and second portions $116_1$, $116_2$ of FIG. 8 in the embodiment of FIGS. 9-11). In one arrangement, the apparatuses may be disposed into a complimentary shaped transport container (e.g., tub) transport to the pathologist or the like. Furthermore, while the disclosed apparatuses have been primarily discussed in the context of x-ray imaging, it is envisioned that the apparatuses could also be used to non-movably hold and retain a specimen for other types of imaging operations (e.g., ultrasound imaging).

In one arrangement, the elastically deformable members 116/124, 516/524, etc. may be configured so that the reference plane 200 is other than parallel or perpendicular to the imaging axis during both of the first and second imaging steps. As just one example, the elastically deformable portion 116 of the first positioning member 104 of the apparatus 100 of FIGS. 1-7 may be angled or tapered (e.g., at a 45°) relative to the bottom surface of the first positioning member 104 (e.g., relative to second external side 156) while the elastically deformable portion 124 of the second positioning member 108 of the apparatus 100 of FIGS. 1-7 may be angled or tapered (e.g., at a 45°) relative to the top surface of the second positioning member 108 (e.g., relative to first external side 152). As neither of the first and second imaging steps would thus include the imaging axis being substantially coincident with or parallel to the reference plane 200, increases in quality of the first and second images may be achieved by limiting the degree to which the imaging signal 400 may propagate past sharp or corners or other surface transitions of the first and second positioning members.

Furthermore, while the apparatuses have primarily been disclosed for use with tissue specimens 300, it is envisioned that the apparatuses could also be used with other types of specimens (e.g., non-living specimens). Still further, the use of "first," "second," "third," etc. herein (e.g., "first external side," "second external side," etc.) and the like does not necessarily connote any specific number of features or components in the disclosed apparatuses. Rather, such labels have merely been used to differentiate among a number of common features (e.g., to differentiate among a number of recesses of the apparatuses) for purposes of facilitating understanding of the various aspects of the apparatuses.

While this disclosure contains many specifics, these should not be construed as limitations on the scope of the disclosure or of what may be claimed, but rather as descriptions of features specific to particular embodiments of the disclosure. Certain features that are described in this specification in the context of separate embodiments and/or arrangements can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

What is claimed is:

1. An apparatus for positionably retaining a tissue specimen for imaging, comprising:
    a first positioning member comprising a portion thereof that is at least partially elastically deformable, wherein the first positioning member includes a body and an opening defined by an outer surface of the body and extending partially into the body for receipt of the tissue specimen, wherein the elastically deformable portion of the first positioning member includes an inner surface of the body that delimits a bottom of the opening, wherein the first positioning member includes a first orientation marker embedded within the body of the first positioning member, and wherein the first orientation marker is less radiolucent than is the body of the first positioning member;
    a second positioning member comprising a portion thereof that is at least partially elastically deformable, wherein the second positioning member includes a body, wherein the elastically deformable portion of the second positioning member is a bottom surface of the body, wherein the second positioning member and the elastically deformable portion of the second positioning member are receivable in the opening defined by the outer surface of the first positioning member, wherein the first and second positioning members are fixably positionable to allow the portions of the first and second positioning members to retain a tissue specimen therebetween within a specimen support volume of the apparatus, wherein first and second orthogonal axes of the apparatus extend through the specimen support volume, and wherein a reference plane extends between the portions of the first and second positioning members when the first and second positioning members are fixably positioned relative to each other;
    a first volume extending about and along the first axis from a first external side of the apparatus to a second external side of the apparatus and encompassing the specimen support volume; and
    a second volume extending about and along the second axis from a third external side of the apparatus to a fourth external side of the apparatus and encompassing the specimen support volume, wherein the first and second volumes are free of any portion having a density greater than either a density of the portion of the first positioning member or a density of the portion of the second positioning member, and wherein the first orientation marker and the tissue specimen appear as respective spaced objects in an image generated by transmitting a beam of electromagnetic radiation through the apparatus.

2. The apparatus of claim 1, wherein the body of the first positioning member includes a sidewall that surrounds the opening, wherein the first orientation marker is embedded within the sidewall, and wherein the sidewall is configured to space the first orientation marker from a specimen received in the opening.

3. The apparatus of claim 2, wherein the sidewall includes an upper surface that includes a first indicator thereon that identifies a location of the first orientation marker.

4. The apparatus of claim 1, wherein the second positioning member includes a second orientation marker embedded within the body of the second positioning member, wherein the second orientation marker is less radiolucent than is the body of the second positioning member, and wherein the first and second orientation markers appear as respective spaced objects in an image generated by transmitting a beam of electromagnetic radiation through the apparatus.

5. A method of imaging a specimen, comprising:
    receiving a second retention member of a positioning apparatus within an opening defined by an outer surface of a first retention member of the positioning apparatus, the receiving including elastically deforming the first and second retention members to surround opposite portions of a specimen;
    securing the first and second retention members against movement relative to each other to retain the specimen therebetween, wherein a reference plane extends between the first and second retention members when the specimen is retained therebetween;
    generating, at a source of electromagnetic radiation, a beam of electromagnetic radiation;
    transmitting, while the specimen is retained between the first and second retention members, the beam along an imaging axis through the specimen and the first and second retention members;
    inhibiting transmission of a portion of the beam through a portion of the first retention member;
    receiving the beam at an imaging detector; and
    generating an image from the beam received at the imaging detector, wherein the generated image includes the tissue specimen and a first object representing the portion of the first retention member, and wherein the specimen is spaced from the first object in the generated image.

6. The method of claim 5, wherein the imaging axis is perpendicular to the reference plane.

7. The method of claim 5, wherein the imaging axis is coincident with the reference plane.

8. The method of claim 5, wherein the inhibiting includes inhibiting transmission of another portion of the beam through a portion of the second retention member, wherein the generated image includes a second object representing the portion of the second retention member, and wherein the first object is spaced from the second object in the generated image.

9. The method of claim 8, wherein the second object is encompassed within the specimen in the generated image.

10. The method of claim 8, wherein the second object is spaced from the specimen in the generated image.

11. The method of claim 5, further comprising:
reorienting the reference plane from a first position to a second position relative to the imaging axis;
second generating a beam of electromagnetic radiation;
second transmitting the beam along the imaging axis through the specimen and the first and second retention members;
second inhibiting transmission of a portion of the beam through the portion of the first retention member;
second receiving the beam at the imaging sensor; and
second generating a second image from the beam received at the imaging detector, wherein the second generated image includes the tissue specimen and a first object representing the portion of the first retention member, and wherein the specimen is spaced from the first object in the second generated image.

12. The method of claim 11, wherein the imaging axis is perpendicular to the reference plane during the transmitting, and wherein the imaging axis is substantially parallel to the reference plane during the second transmitting.

13. The method of claim 11, wherein the reorienting the reference plane from the first position to the second position includes reorienting the positioning apparatus by 90 degrees.

14. The method of claim 11, wherein the reorienting the reference plane from the first position to the second position includes rotating the positioning apparatus.

15. The method of claim 11, further comprising:
using the first and second generated images to verify tissue margins of the specimen.

16. The method of claim 11, wherein the second inhibiting includes second inhibiting transmission of the other portion of the beam through the portion of the second retention member, wherein the second generated image includes a second object representing the portion of the second retention member, wherein the first object is spaced from the second object in the second generated image, and wherein the second object is spaced from the tissue specimen in the second generated image.

17. A method of imaging a specimen, comprising:
elastically deforming first and second retention members to surround opposing portions of a specimen of one of a left or right breast;
inserting the second retention member into an opening defined by an outer surface of the first retention member;
securing the first and second retention members against movement relative to each other to retain the specimen of the one of the left or right breast therebetween within a specimen support volume of the apparatus, wherein a reference plane extends between the first and second retention members when the specimen of the one of the left or right breast is retained therebetween; and
first transmitting an imaging signal through the positioning apparatus and the specimen of the one of the left or right breast along a first axis that is substantially perpendicular to the reference plane to obtain a first image, wherein the first image includes the specimen of the one of the left or right breast and a first object that represents the other of the left or right breast, wherein the specimen and the first object are spaced in the first image, wherein the first image includes a second object that represents the one of the left or right breast, and wherein the second object is encompassed within the specimen in the first image.

18. The method of claim 17, further including:
reorienting the apparatus; and
breast, wherein the specimen and the first object are spaced in the second image.

19. The method of claim 18, further including:
reorienting the apparatus; and
third transmitting an imaging signal through the positioning apparatus and the specimen of the one of the left or right breast along a third axis that is perpendicular to the first and second axes to obtain a third image, wherein the third image includes the specimen of the one of the left or right breast and the first object that represents the other of the left or right breast, wherein the specimen and the first object are spaced in the third image.

20. The apparatus of claim 4, wherein the second orientation marker appears as an object that is encompassed within the tissue specimen in the image.

* * * * *